(12) United States Patent
Springsteen et al.

(10) Patent No.: US 11,505,519 B2
(45) Date of Patent: Nov. 22, 2022

(54) SYNTHESIS OF ORGANIC ACIDS FROM α-KETO ACIDS

(71) Applicant: Furman University, Greenville, SC (US)

(72) Inventors: Gregory Gardner Springsteen, Greenville, SC (US); Robert Trent Stubbs, Roswell, GA (US)

(73) Assignee: Furman University, Greenville, SC (US)

( * ) Notice: Subject to any disclaimer, the term of this patent is extended or adjusted under 35 U.S.C. 154(b) by 63 days.

(21) Appl. No.: 16/746,124

(22) Filed: Jan. 17, 2020

(65) Prior Publication Data

US 2020/0231527 A1 Jul. 23, 2020

Related U.S. Application Data

(60) Provisional application No. 62/825,084, filed on Mar. 28, 2019, provisional application No. 62/793,529, filed on Jan. 17, 2019.

(51) Int. Cl.
| | |
|---|---|
| *C07C 51/373* | (2006.01) |
| *C07C 51/285* | (2006.01) |
| *C07C 51/377* | (2006.01) |
| *C07C 51/36* | (2006.01) |
| *C07C 51/367* | (2006.01) |
| *C07C 51/347* | (2006.01) |
| *C07C 55/10* | (2006.01) |
| *C07C 55/22* | (2006.01) |
| *C07C 57/13* | (2006.01) |
| *C07C 57/15* | (2006.01) |

(Continued)

(52) U.S. Cl.
CPC .......... *C07C 51/373* (2013.01); *C07C 51/285* (2013.01); *C07C 51/347* (2013.01); *C07C 51/36* (2013.01); *C07C 51/367* (2013.01); *C07C 51/377* (2013.01); *C07C 55/10* (2013.01); *C07C 55/22* (2013.01); *C07C 57/13* (2013.01); *C07C 57/15* (2013.01); *C07C 59/245* (2013.01); *C07C 59/347* (2013.01); *C07C 59/76* (2013.01)

(58) Field of Classification Search
None
See application file for complete search history.

(56) References Cited

U.S. PATENT DOCUMENTS

| | | | |
|---|---|---|---|
| 2013/0006099 A1 | 1/2013 | Millward et al. | |
| 2016/0016890 A1* | 1/2016 | Bradley | A23K 20/142 562/562 |
| 2017/0044551 A1* | 2/2017 | Chokhawala | C12Y 402/01079 |

FOREIGN PATENT DOCUMENTS

WO 2014/150909 A1 9/2014

OTHER PUBLICATIONS

Butch ("Production of Tartrates by Cyanide-Mediated Dimerization of Glyoxylate: A Potential Abiotic Pathway to the Citric Acid Cycle" J. Am. Chem. Soc. 2013, 135, p. 13440-13445). (Year: 2013).*

(Continued)

*Primary Examiner* — Amy C Bonaparte
(74) *Attorney, Agent, or Firm* — McDermott Will & Emery LLP

(57) ABSTRACT

Methods for syntheses of organic acids from α-keto acids, including methods for syntheses of isotopically enriched organic acids from α-keto acids are disclosed. The isotopically enriched organic acids are useful, for example, in metabolic flux analyses.

25 Claims, 2 Drawing Sheets

(51) Int. Cl.
      *C07C 59/245*   (2006.01)
      *C07C 59/347*   (2006.01)
      *C07C 59/76*    (2006.01)

(56) References Cited

OTHER PUBLICATIONS

Liu ("Facile Pd-catalyzed chemoselective transfer hydrogenation of olefins using formic acid in water" Tetrahedron Letters, 2016, 57, p. 4845-4849) (Year: 2016).*

Springsteen ("Linked cycles of oxidative decarboxylation of glyoxylate as protometabolic analogs of the citric acid cycle" Nature Communications, 2018, 9:91) (Year: 2018).*

Muchowska ("Synthesis and breakdown of universal metabolic precursors promoted by iron" Nature, 569, May 2, 2019, p. 104) (Year: 2019).*

International Search Report dated May 18, 2020 in International Application No. PCT/US2020/014023.

Written Opinion dated May 18, 2020 in International Application No. PCT/US2020/014023.

Brown et al., "The microwave spectrum and structure of tricarbon monoxide", Journal of the American Chemical Society, vol. 107, pp. 4112-4115, XP002470566, Jan. 1, 1985.

Davidson, David, et al. "The Preparation of Aromatic Alcohols by the Crossed Cannizzaro Reaction with Formaldehyde", Journal of the American Chemical Society, vol. 57, No. 5, pp. 905-905, May 1935.

Stubbs, R. Trent, et al. "A Plausible Metal-Free Ancestral Analogue of the Krebs Cycle Composed Entirely of α-Ketoacids", Nat Chem., vol. 12, No. 11, pp. 1016-1022, Nov. 2020.

* cited by examiner

# SYNTHESIS OF ORGANIC ACIDS FROM α-KETO ACIDS

CROSS REFERENCE TO RELATED APPLICATIONS

This application claims priority to U.S. Provisonal Application No. 62/793,529, filed on Jan. 17, 2019, and U.S. Provisional Application No. 62/825,084, filed on Mar. 28, 2019, which are incorporated herein by reference in their entireties.

FIELD

The present disclosure is generally directed to methods of synthesis of organic acids, for example, organic acids that are biological intermediates in metabolic pathways.

BACKGROUND

Described herein are methods for syntheses of organic acids from α-keto acids, including methods for syntheses of isotopically enriched organic acids from α-keto acids. The isotopically enriched organic acids are useful, for example, in metabolic flux analyses.

Metabolic flux analysis is used to detect metabolic irregularities caused by altered cell expression or pathogenic activity resulting from conditions such as cancer, malaria or bacterial infection. The method works by tracing stable non-natural isotopes of biological intermediates as they are processed in vivo and in vitro. Tissue or fluid samples are analyzed by mass spectrometry and/or nuclear magnetic resonance spectroscopy to determine the number and/or location of isotopically labeled atoms (typically $^{13}C$). This pattern helps to determine the relative activities of biological pathways, especially of the tricarboxylic acid (TCA) cycle and glycolysis where atypical metabolisms are often indicative of specific pathologies. Recent progress in the sensitivity of mass spectrometry instrumentation has increased the application of this technology; however, the field is currently limited by the expense and lack of availability of isotopically tagged metabolites. Often the isotopically tagged metabolites are difficult to produce on a large scale.

The generation of organic acid metabolites has typically required the use of biological enzymes either inside or outside of a cellular matrix. Attempts directed towards the chemical synthesis of these compounds without enzymatic assistance have suffered from low yields and poor specificity even under harsh reaction conditions.

Further, current syntheses of α-keto acid and organic acid metabolites employ biological or synthetic methods that allow only a limited number of isotopic patterns. There is a need in the art for methods to synthesize metabolites with greater flexibility. Additionally, there is a need for a cheaper and more efficient process to produce metabolites that circumvent the current syntheses which employ relatively expensive and complex processes involving enzymes, catalysis, harsh reaction conditions, multiple reagent additions, unit operations or process steps, and/or microorganisms.

SUMMARY

The present disclosure provides methods of synthesis of organic acids, for example, organic acids that are biological intermediates in metabolic pathways. In one aspect the present disclosure describes an aldol condensation using an aldehydic reactant that serves two roles: 1) it is an electrophile that forms a portion of the product carbon skeleton (aldol addition compound), and 2) it is a reductant performing a conjugate reduction on the aldol product enone (aldol condensation compound). Surprisingly, it was found that an aldol addition coupled with a conjugant reduction, where the reagent in the aldol addition may also be the reductant, yielded a cheaper, more efficient, and more flexible metabolite synthesis process.

Accordingly, in a first aspect, provided herein is a method for reducing an α,β-unsaturated bond in an aldol condensation compound, the method comprising
 (1) contacting an aldol nucleophile with an aldehydic electrophile to provide an aldol addition compound;
 (2) dehydrating the aldol addition compound to provide an aldol condensation compound having an α,β-unsaturated bond; and
 (3) reducing the α,β-unsaturated bond in the aldol condensation compound by contacting the aldol condensation compound with the aldehydic electrophile.
In this method, the aldehydic electrophile is a reactant in step (1) and a reductant in step (3).

In a second aspect, provided herein is a method for preparing an organic acid, the method comprising
 (1) contacting an α-keto acid with an aldehydic electrophile to provide an aldol addition compound;
 (2) dehydrating the aldol addition compound to provide an aldol condensation compound having an α,β-unsaturated bond;
 (3) reducing the α,β-unsaturated bond in the aldol condensation compound by contacting the aldol condensation compound with the aldehydic electrophile; and
 (4) oxidatively decarboxylating the reduced aldol condensation compound to provide the organic acid; or
 (5) reducing the keto group in the reduced aldol condensation compound to provide the organic acid; or
 (6) subjecting the reduced aldol condensation compound to reductive amination or transamination to provide the organic acid.
In this method, the aldehydic electrophile is a reactant in step (1) and a reductant in step (3).

Further, the methods of synthesis described herein allow for synthesis of isotopically labeled metabolites that are useful, for example, in metabolic flux analysis.

DETAILED DESCRIPTION

Figure 1:
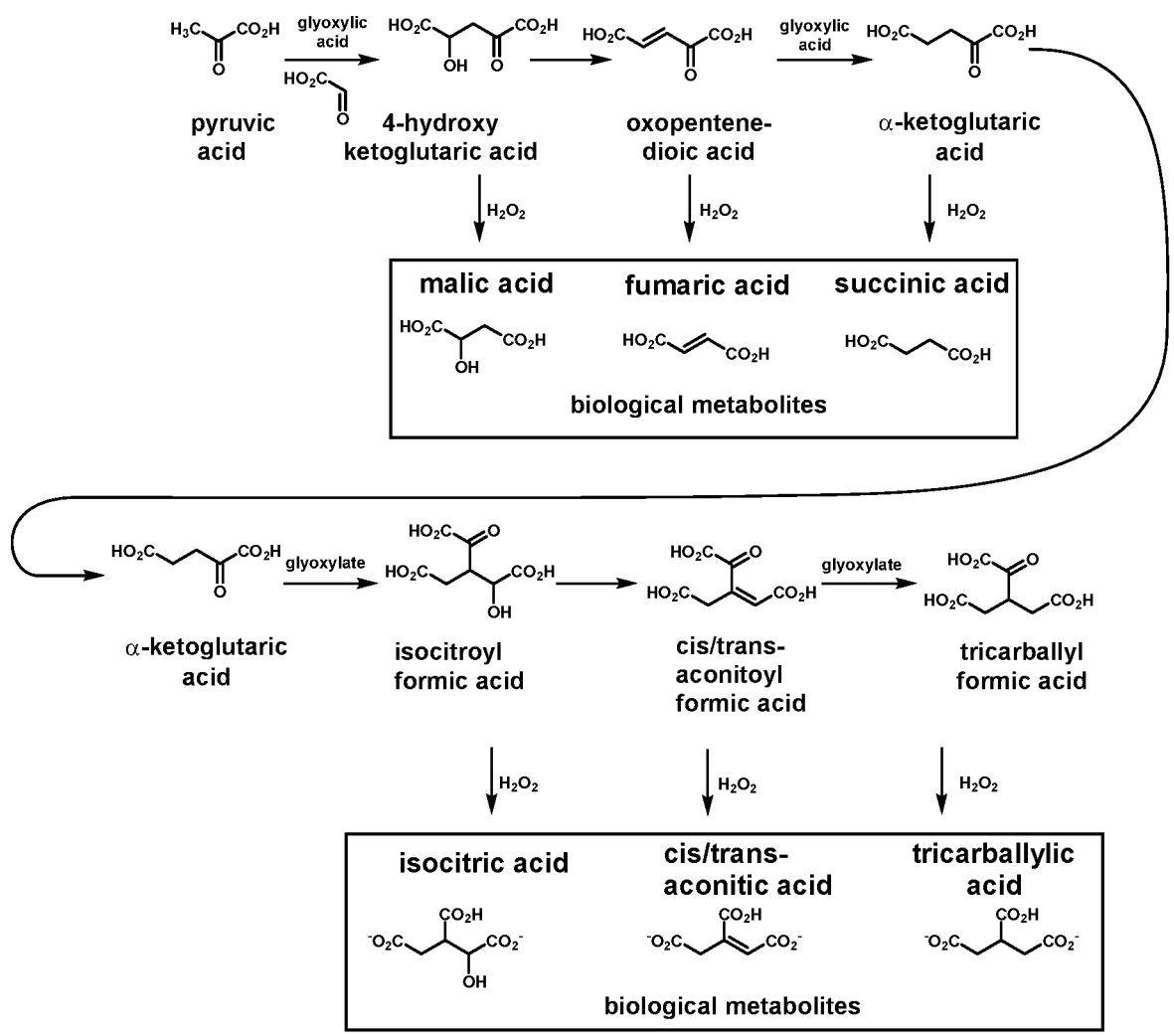
FIG. 1 illustrates reaction sequences described herein for the synthesis of certain organic acids and/or biological metabolites.

This disclosure provides, in some embodiments, isotopically enriched derivatives and non-natural compounds that can be produced by a new chemical process described herein. The isotopically enriched derivatives and non-natural compounds described herein may aid in metabolic flux analysis, metabolomics, and enzyme inhibition. The production of novel isotopes of known and unknown metabolites in high yield and purity will greatly assist metabolic analyses that use these labels to trace biological pathways and degradation.

The present disclosure, in one embodiment, relates to a method for the production of α-keto acids and organic acids thereof, in particular to a method of producing $^2$H and/or $^{13}$C enriched-α-keto acids and organic acids thereof. More particularly, the present disclosure relates to the synthesis of metabolites by exchanging of one or more carboxylate groups (—$CO^{2-}$) for α-ketoacids (—$C(O)CO^{2-}$), which enables the synthesis of these metabolites to progress in water at neutral pH and produce patterns of isotopic labelling not previously available. Thus, an α-ketoacid moiety is converted to an organic acid moiety thereof such that the net conversion is the removal of the keto group of the α-ketoacid moiety.

Advantageously, the exchange of one or more carboxylate groups (—$CO_2^-$) for α-ketoacids (—$C(O)CO_2^-$) enables the synthesis of these metabolites to progress in water at about neutral pH without enzyme catalysis. An oxidation with aqueous hydrogen peroxide or $O_2$ or any other suitable oxidant at the end of the synthesis transforms the α-ketoacid into a carboxylate group. The reactions typically start from pyruvate and glyoxylate, to produce valuable analogs of metabolic intermediates. The processes provided herein confer several improvements over other methods such as selectivity, yield, mild reaction conditions, and enzyme-free processes that are easily scalable. The processes described herein have particular value in their ability to produce isotopically-labeled compounds priced at hundreds of thousands per gram from reactants available at a small fraction of that cost. Novel labeling patterns can also be generated that are currently unavailable through any other route. The processes described herein also enable the synthesis of chemical analogs of biological metabolites that are potentially useful as pharmaceuticals (e.g., and without limitation, enzyme inhibitors, compounds for metabolic flux analyses) and in materials chemistry (e.g., and without limitation, biodegradable polyesters). Also included in the scope of embodiments provided herein are analogs and metabolic intermediates produced from the synthesis of metabolites.

Definitions

The following description sets forth exemplary embodiments of the present technology. It should be recognized, however, that such description is not intended as a limitation on the scope of the present disclosure but is instead provided as a description of exemplary embodiments.

As used in the present specification, the following words, phrases and symbols are generally intended to have the meanings as set forth below, except to the extent that the context in which they are used indicates otherwise.

A dash ("-") that is not between two letters or symbols is used to indicate a point of attachment for a substituent. For example, —$C(O)NH_2$ is attached through the carbon atom. A dash at the front or end of a chemical group is a matter of convenience; chemical groups may be depicted with or without one or more dashes without losing their ordinary meaning. A wavy line drawn through a line in a structure indicates a point of attachment of a group. Unless chemically or structurally required, no directionality is indicated or implied by the order in which a chemical group is written or named.

The prefix "$C_{u-v}$" indicates that the following group has from u to v carbon atoms. For example, "$C_{1-6}$ alkyl" indicates that the alkyl group has from 1 to 6 carbon atoms.

Reference to "about" a value or parameter herein includes (and describes) embodiments that are directed to that value or parameter per se. In certain embodiments, the term "about" includes the indicated amount±10%. In other embodiments, the term "about" includes the indicated amount±5%. In certain other embodiments, the term "about" includes the indicated amount±1%. Also, to the term "about X" includes description of "X". Also, the singular forms "a" and "the" include plural references unless the context clearly dictates otherwise. Thus, e.g., reference to "the compound" includes a plurality of such compounds and reference to "the assay" includes reference to one or more assays and equivalents thereof known to those skilled in the art.

Reference to "substantially" a value or parameter herein includes embodiments that are directed to that parameter or value per se. In certain embodiments, the term "substantially" includes the indicated amount±10%. In certain embodiments, the term "substantially" includes the indicated amount±5%. In certain embodiments, the term "substantially" includes the indicated amount±1%.

"Alkyl" refers to an unbranched or branched saturated hydrocarbon chain. As used herein, alkyl has 1 to 20 carbon atoms (i.e. $C_{1-20}$ alkyl), 1 to 8 carbon atoms (i.e., $C_{1-8}$ alkyl), 1 to 6 carbon atoms (i.e., $C_{1-6}$ alkyl), or 1 to 4 carbon atoms (i.e., $C_{1-4}$ alkyl). Examples of alkyl groups include methyl, ethyl, propyl, isopropyl, n-butyl, sec-butyl, iso-butyl, tert-butyl, pentyl, 2-pentyl, isopentyl, neopentyl, hexyl, 2-hexyl, 3-hexyl, and 3-methylpentyl. When an alkyl residue having a specific number of carbons is named by chemical name or identified by molecular formula, all positional isomers having that number of carbons may be encompassed; thus, for example, "butyl" includes n-butyl (i.e. —$(CH_2)_3CH_3$), sec-butyl (i.e. —$CH(CH_3)CH_2CH_3$), isobutyl (i.e. —$CH_2CH(CH_3)_2$) and tert-butyl (i.e. —$C(CH_3)_3$); and "propyl" includes n-propyl (i.e. —$(CH_2)_2CH_3$) and isopropyl (i.e. —$CH(CH_3)_2$).

"Alkenyl" refers to an alkyl group containing at least one carbon-carbon double bond and having from 2 to 20 carbon atoms (i.e., $C_{2-20}$ alkenyl), 2 to 8 carbon atoms (i.e., $C_{2-8}$ alkenyl), 2 to 6 carbon atoms (i.e., $C_{2-6}$ alkenyl), or 2 to 4 carbon atoms (i.e., $C_{2-4}$ alkenyl). Examples of alkenyl groups include ethenyl, propenyl, butadienyl (including 1,2-butadienyl and 1,3-butadienyl).

"Alkynyl" refers to an alkyl group containing at least one carbon-carbon triple bond and having from 2 to 20 carbon atoms (i.e., $C_{2-20}$ alkynyl), 2 to 8 carbon atoms (i.e., $C_{2-8}$ alkynyl), 2 to 6 carbon atoms (i.e., $C_{2-6}$ alkynyl), or 2 to 4 carbon atoms (i.e., $C_{2-4}$ alkynyl). The term "alkynyl" also includes those groups having one triple bond and one double bond.

"Alkoxy" refers to the group "alkyl-O—". Examples of alkoxy groups include methoxy, ethoxy, n-propoxy, iso-propoxy, n-butoxy, tert-butoxy, sec-butoxy, n-pentoxy, n-hexoxy, and 1,2-dimethylbutoxy.

"Alkylthio" refers to the group "alkyl-S—".

"Alkylsulfonyl" refers to the group —$S(O)_2R$, where R is alkyl.

"Alkylsulfinyl" refers to the group —$S(O)R$, where R is alkyl.

"Acyl" refers to a group —$C(O)R$, wherein R is hydrogen, alkyl, cycloalkyl, heterocyclyl, aryl, heteroalkyl, or heteroaryl; each of which may be optionally substituted, as defined herein. Examples of acyl include formyl, acetyl, cylcohexylcarbonyl, cyclohexylmethyl-carbonyl, and benzoyl.

"Amido" refers to both a "C-amido" group which refers to the group —$C(O)NR^yR^z$ and an "N-amido" group which refers to the group —NR$^y$C(O)R$^z$, wherein R$^y$ and R$^z$ are independently selected from the group consisting of hydrogen, alkyl, aryl, haloalkyl, or heteroaryl; each of which may be optionally substituted.

"Amino" refers to the group —NR$^y$R$^z$ wherein R$^y$ and R$^z$ are independently selected from the group consisting of hydrogen, alkyl, haloalkyl, aryl, or heteroaryl; each of which may be optionally substituted.

"Amidino" refers to —C(NH)(NH$_2$).

"Aryl" refers to an aromatic carbocyclic group having a single ring (e.g. monocyclic) or multiple rings (e.g. bicyclic or tricyclic) including fused systems. As used herein, aryl has 6 to 20 ring carbon atoms (i.e., C$_{6-20}$ aryl), 6 to 12 carbon ring atoms (i.e., C$_{6-12}$ aryl), or 6 to 10 carbon ring atoms (i.e., C$_{6-10}$ aryl). Examples of aryl groups include phenyl, naphthyl, fluorenyl, and anthryl. Aryl, however, does not encompass or overlap in any way with heteroaryl defined below. If one or more aryl groups are fused with a heteroaryl, the resulting ring system is heteroaryl. If one or more aryl groups are fused with a heterocyclyl, the resulting ring system is heterocyclyl.

"Azido" refers to —N$_3$.

"Carbamoyl" refers to both an "O-carbamoyl" group which refers to the group —O—C(O)NR$^y$R$^z$ and an "N-carbamoyl" group which refers to the group —NR$^y$C(O)OR$^z$, wherein R$^y$ and R$^z$ are independently selected from the group consisting of hydrogen, alkyl, aryl, haloalkyl, or heteroaryl; each of which may be optionally substituted.

"Carboxyl" refers to —C(O)OH. Carboxyl may also be drawn herein as carboxylate —CO$_2$$^-$. As used herein, the chemical suffixes -ate and -ic acid are interchangeable and both refer to a molecule with at least one carboxylic acid functional group that may or may not be ionized at higher pH to provide a salt. The term "salt" refers to an ionic compound formed between an acid and a base. A salt of a compound disclosed herein is formed between an acid and a base. When the compound provided herein contains an acidic functionality, such salts include, without limitation, alkali metal, alkaline earth metal, and ammonium salts. Exemplary, and non-limiting cations useful in salts include Na, K, Rb, Cs, NH$_4$, Ca, Ba, imidazolium, and ammonium cations. Accordingly, where a carboxylate is drawn, it is to be understood that a suitable counterion is present. In such instances the counterion present arises from a base in the reaction mixture (e.g., Na, K, Rb, Cs, NH$_4$, Ca, Ba or other suitable counterions).

"Carboxyl ester" refers to both —OC(O)R and —C(O)OR, wherein R is hydrogen, alkyl, cycloalkyl, heterocyclyl, aryl, heteroalkyl, or heteroaryl; each of which may be optionally substituted, as defined herein.

"Cyano" or "carbonitrile" refers to the group —CN.

"Cycloalkyl" refers to a saturated or partially unsaturated cyclic alkyl group having a single ring or multiple rings including fused, bridged, and spiro ring systems. The term "cycloalkyl" includes cycloalkenyl groups (i.e. the cyclic group having at least one double bond). As used herein, cycloalkyl has from 3 to 20 ring carbon atoms (i.e., C$_{3-20}$ cycloalkyl), 3 to 12 ring carbon atoms (i.e., C$_{3-12}$ cycloalkyl), 3 to 10 ring carbon atoms (i.e., C$_{3-10}$ cycloalkyl), 3 to 8 ring carbon atoms (i.e., C$_{3-8}$ cycloalkyl), or 3 to 6 ring carbon atoms (i.e., C$_{3-6}$ cycloalkyl). Examples of cycloalkyl groups include cyclopropyl, cyclobutyl, cyclopentyl, and cyclohexyl.

"Guanidino" refers to —NHC(NH)(NH$_2$).

"Hydrazino" refers to —NHNH$_2$.

"Imino" refers to a group —C(NR)R, wherein each R is alkyl, cycloalkyl, heterocyclyl, aryl, heteroalkyl, or heteroaryl; each of which may be optionally substituted, as defined herein.

"Halogen" or "halo" includes fluoro, chloro, bromo, and iodo. "Haloalkyl" refers to an unbranched or branched alkyl group as defined above, wherein one or more hydrogen atoms are replaced by a halogen. For example, where a residue is substituted with more than one halogen, it may be referred to by using a prefix corresponding to the number of halogen moieties attached. Dihaloalkyl and trihaloalkyl refer to alkyl substituted with two ("di") or three ("tri") halo groups, which may be, but are not necessarily, the same halogen. Examples of haloalkyl include difluoromethyl (—CHF$_2$) and trifluoromethyl (—CF$_3$).

"Haloalkoxy" refers to an alkoxy group as defined above, wherein one or more hydrogen atoms are replaced by a halogen.

"Heteroalkyl" refers to an alkyl group in which one or more of the carbon atoms (and any associated hydrogen atoms) are each independently replaced with the same or different heteroatomic group. The term "heteroalkyl" includes unbranched or branched saturated chain having carbon and heteroatoms. By way of example, 1, 2 or 3 carbon atoms may be independently replaced with the same or different heteroatomic group. Heteroatomic groups include, but are not limited to, —NR—, —O—, —S—, —S(O)—, —S(O)$_2$—, and the like, where R is H, alkyl, aryl, cycloalkyl, heteroalkyl, heteroaryl or heterocyclyl, each of which may be optionally substituted. Examples of heteroalkyl groups include —OCH$_3$, —CH$_2$OCH$_3$, —SCH$_3$, —CH$_2$SCH$_3$, —NRCH$_3$, and —CH$_2$NRCH$_3$, where R is hydrogen, alkyl, aryl, arylalkyl, heteroalkyl, or heteroaryl, each of which may be optionally substituted. As used herein, heteroalkyl includes 1 to 10 carbon atoms, 1 to 8 carbon atoms, or 1 to 4 carbon atoms; and 1 to 3 heteroatoms, 1 to 2 heteroatoms, or 1 heteroatom.

"Heteroaryl" refers to an aromatic group having a single ring, multiple rings, or multiple fused rings, with one or more ring heteroatoms independently selected from nitrogen, oxygen, and sulfur. As used herein, heteroaryl includes 1 to 20 ring carbon atoms (i.e., C$_{1-20}$ heteroaryl), 3 to 12 ring carbon atoms (i.e., C$_{3-12}$ heteroaryl), or 3 to 8 carbon ring atoms (i.e., C$_{3-8}$ heteroaryl); and 1 to 5 heteroatoms, 1 to 4 heteroatoms, 1 to 3 ring heteroatoms, 1 to 2 ring heteroatoms, or 1 ring heteroatom independently selected from nitrogen, oxygen, and sulfur. Examples of heteroaryl groups include pyrimidinyl, purinyl, pyridyl, pyridazinyl, benzothiazolyl, and pyrazolyl. Examples of the fused-heteroaryl rings include, but are not limited to, benzo[d]thiazolyl, quinolinyl, isoquinolinyl, benzo[b]thiophenyl, indazolyl, benzo[d]imidazolyl, pyrazolo[1,5-a]pyridinyl, and imidazo[1,5-a]pyridinyl, where the heteroaryl can be bound via either ring of the fused system. Any aromatic ring, having a single or multiple fused rings, containing at least one heteroatom, is considered a heteroaryl regardless of the attachment to the remainder of the molecule (i.e., through any one of the fused rings). Heteroaryl does not encompass or overlap with aryl as defined above.

"Heterocyclyl" refers to a saturated or unsaturated cyclic alkyl group, with one or more ring heteroatoms independently selected from nitrogen, oxygen and sulfur. The term "heterocyclyl" includes heterocycloalkenyl groups (i.e. the heterocyclyl group having at least one double bond), bridged-heterocyclyl groups, fused-heterocyclyl groups, and spiro-heterocyclyl groups. A heterocyclyl may be a single ring or multiple rings wherein the multiple rings may be fused, bridged, or spiro. Any non-aromatic ring containing at least one heteroatom is considered a heterocyclyl, regardless of the attachment (i.e., can be bound through a carbon atom or a heteroatom). Further, the term heterocyclyl is intended to encompass any non-aromatic ring containing at least one heteroatom, which ring may be fused to an aryl or heteroaryl ring, regardless of the attachment to the remainder of the molecule. As used herein, heterocyclyl has 2 to 20 ring carbon atoms (i.e., $C_{2-20}$ heterocyclyl), 2 to 12 ring carbon atoms (i.e., $C_{2-12}$ heterocyclyl), 2 to 10 ring carbon atoms (i.e., $C_{2-10}$ heterocyclyl), 2 to 8 ring carbon atoms (i.e., $C_{2-8}$ heterocyclyl), 3 to 12 ring carbon atoms (i.e., $C_{3-12}$ heterocyclyl), 3 to 8 ring carbon atoms (i.e., $C_{3-8}$ heterocyclyl), or 3 to 6 ring carbon atoms (i.e., $C_{3-6}$ heterocyclyl); having 1 to 5 ring heteroatoms, 1 to 4 ring heteroatoms, 1 to 3 ring heteroatoms, 1 to 2 ring heteroatoms, or 1 ring heteroatom independently selected from nitrogen, sulfur or oxygen. Examples of heterocyclyl groups include pyrrolidinyl, piperidinyl, piperazinyl, oxetanyl, dioxolanyl, azetidinyl, and morpholinyl. As used herein, the term "bridged-heterocyclyl" refers to a four- to ten-membered cyclic moiety connected at two non-adjacent atoms of the heterocyclyl with one or more (e.g. 1 or 2) four- to ten-membered cyclic moiety having at least one heteroatom where each heteroatom is independently selected from nitrogen, oxygen, and sulfur. As used herein, bridged-heterocyclyl includes bicyclic and tricyclic ring systems. Also used herein, the term "spiro-heterocyclyl" refers to a ring system in which a three- to ten-membered heterocyclyl has one or more additional ring, wherein the one or more additional ring is three- to ten-membered cycloalkyl or three- to ten-membered heterocyclyl, where a single atom of the one or more additional ring is also an atom of the three- to ten-membered heterocyclyl. Examples of the spiro-heterocyclyl rings include bicyclic and tricyclic ring systems, such as 2-oxa-7-azaspiro[3.5]nonanyl, 2-oxa-6-azaspiro[3.4]octanyl, and 6-oxa-1-azaspiro[3.3]heptanyl. Examples of the fused-heterocyclyl rings include, but are not limited to, 1,2,3,4-tetrahydroisoquinolinyl, 4,5,6,7-tetrahydrothieno[2,3-c]pyridinyl, indolinyl, and isoindolinyl, where the heterocyclyl can be bound via either ring of the fused system.

"Hydroxy" or "hydroxyl" refers to the group —OH.

"Oxo" refers to the group (=O) or (O).

"Nitro" refers to the group —$NO_2$.

"Sulfonyl" refers to the group —$S(O)_2R$, where R is alkyl, haloalkyl, heterocyclyl, cycloalkyl, heteroaryl, or aryl. Examples of sulfonyl are methylsulfonyl, ethylsulfonyl, phenylsulfonyl, and toluenesulfonyl.

"Thiocyanate" refers to the group —SCN.

"Thiol" refers to the group —SH.

"Thioxo" or "thione" refer to the group (=S) or (S).

Certain commonly used alternative chemical names may be used. For example, a divalent group such as a divalent "alkyl" group, a divalent "aryl" group, etc., may also be referred to as an "alkylene" group or an "alkylenyl" group, an "arylene" group or an "arylenyl" group, respectively. Also, unless indicated explicitly otherwise, where combinations of groups are referred to herein as one moiety, e.g. arylalkyl, the last mentioned group contains the atom by which the moiety is attached to the rest of the molecule.

The terms "optional" or "optionally" means that the subsequently described event or circumstance may or may not occur, and that the description includes instances where said event or circumstance occurs and instances in which it does not. Also, the term "optionally substituted" refers to any one or more hydrogen atoms on the designated atom or group which may or may not be replaced by a moiety other than hydrogen.

Some of the compounds exist as tautomers. Tautomers are in equilibrium with one another. For example, α-keto acid containing compounds may exist in equilibrium with their enolate tautomers. Regardless of which tautomer is shown, and regardless of the nature of the equilibrium among tautomers, the compounds are understood by one of ordinary skill in the art to comprise both α-keto acid and enolate acid tautomers.

The term "substituted" means that any one or more hydrogen atoms on the designated atom or group is replaced with one or more substituents other than hydrogen, provided that the designated atom's normal valence is not exceeded. The one or more substituents include, but are not limited to, alkyl, alkenyl, alkynyl, alkoxy, acyl, amino, amido, amidino, aryl, azido, carbamoyl, carboxyl, carboxyl ester, cyano, guanidino, halo, haloalkyl, haloalkoxy, heteroalkyl, heteroaryl, heterocyclyl, hydroxy, hydrazino, imino, oxo, nitro, alkylsuifinyl, sulfonic acid, alkylsulfonyl, thiocyanate, thiol, thione, or combinations thereof. Polymers or similar indefinite structures arrived at by defining substituents with further substituents appended ad infinitum (e.g., a substituted aryl having a substituted alkyl which is itself substituted with a substituted aryl group, which is further substituted by a substituted heteroalkyl group, etc.) are not intended for inclusion herein. Unless otherwise noted, the maximum number of serial substitutions in compounds described herein is three. For example, serial substitutions of substituted aryl groups with two other substituted aryl groups are limited to ((substituted aryl)substituted aryl) substituted aryl. Similarly, the above definitions are not intended to include impermissible substitution patterns (e.g., methyl substituted with 5 fluorines or heteroaryl groups having two adjacent oxygen ring atoms). Such impermissible substitution patterns are well known to the skilled artisan. When used to modify a chemical group, the term "substituted" may describe other chemical groups defined herein. Unless specified otherwise, where a group is described as optionally substituted, any substituents of the group are themselves unsubstituted. For example, in some embodiments, the term "substituted alkyl" refers to an alkyl group having one or more substituents including hydroxyl, halo, alkoxy, cycloalkyl, heterocyclyl, aryl, and heteroaryl. In other embodiments, the one or more substituents may be further substituted with halo, alkyl, haloalkyl, hydroxyl, alkoxy, cycloalkyl, heterocyclyl, aryl, or heteroaryl, each of which is substituted. In other embodiments, the substituents may be further substituted with halo, alkyl, haloalkyl, alkoxy, hydroxyl, cycloalkyl, heterocyclyl, aryl, or heteroaryl, each of which is unsubstituted.

As used herein, the term "aldol addition" describes a bimolecular carbon-carbon bond forming chemical reaction between two species containing at least one carbonyl functional group to produce a single product with a 3-hydroxy carbonyl.

As used herein, the term "aldol condensation" describes a bimolecular carbon-carbon bond forming chemical reaction between two species containing at least one carbonyl functional group to produce a single product with a conjugated enone.

As used herein, the term "oxidative decarboxylation" describes the chemical process of transforming an α-keto acid (—$C(O)CO_2^-$) into a carboxylic acid (—$CO_2$—) and one molecule of $CO_2$ (carbon dioxide). This is typically, but not necessarily, done using either hydrogen peroxide ($H_2O_2$) or molecular oxygen ($O_2$) as the oxidant.

As used herein, the term "dehydration" describes the elimination of $H_2O$ (water) or OH—(hydroxide) leaving behind a double bond where the dehydration occurred.

"Aldol nucleophile" refers to any compound that comprises an enolizable proton and can function as a nucelophile in an aldol reaction. In some embodiments, an aldol nucelophile is an α-ketoacid described herein.

"Aldol addition compound" refers to a beta-hydroxy compound obtained from the reaction of an aldol nucleophile with an electrophile. In some embodiments the electrophile is an aldehydic electrophile described herein (also referred to as an aldehyde reactant). "Aldol enone compound" refers to an α,β-unsaturated compound formed by dehydration of the aldol addition compound. The aldol enone compound is also referred to as the "aldol condensation product."

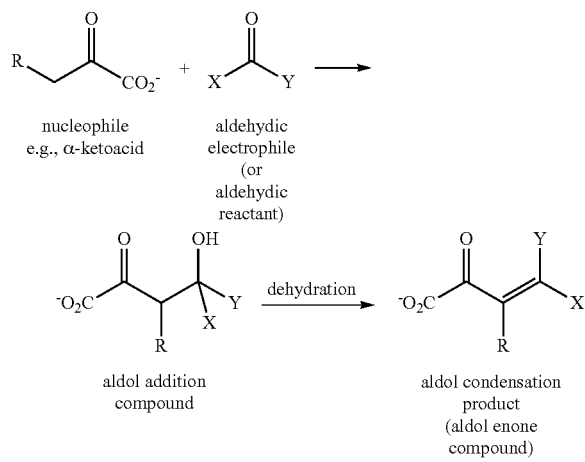

The term "oxidizing" or "oxidation" refers to taking one or more electrons away from a bond or an atom, preferably taking two electrons away from a bond or an atom. Non-limiting examples of oxidation include conversion of an alcohol to an aldehyde.

The term "reducing" or "reduction" refers to adding one or more electron across a bond or an atom, preferably adding two electrons to a bond or an atom. Non-limiting examples of reduction include conversion of a carboxylic acid or an ester thereof to an alcohol.

As used herein the term "hydrolysis" comprises a chemical reaction in which water reacts with a starting compound to produce one or more resulting compound(s); it typically involves the splitting of a bond on the starting compound and the addition of a hydrogen cation and/or of a hydroxide anion to the structure of the starting compound, to obtain the resulting compound(s). Said hydrolysis reaction can be carried out under acidic (pH<7), basic (pH>7) or even neutral conditions (pH=7).

As used herein, the terms "isotope", "isotopic", or "isotopically labeled" refer to an atom having the same number of protons but a different number of neutrons as compared with the most abundant form of the element. Any formula or structure given herein, is intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the disclosure include isotopes of hydrogen, carbon, nitrogen, oxygen, phosphorous, fluorine and chlorine, such as, but not limited to $^2H$ (deuterium, D), $^3H$ (tritium), $^{11}C$, $^{13}C$, $^{14}C$, $^{15}N$, $^{18}F$, $^{31}P$, $^{32}P$, $^{35}S$, $^{36}Cl$ and $^{125}I$. Various isotopically labeled compounds of the present disclosure, for example those into which radioactive isotopes such as $^2H$, $^3H$, $^{13}C$, $^{14}C$ and $^{15}N$ are incorporated. Such isotopically labelled compounds may be useful in metabolic studies, reaction kinetic studies, detection or imaging techniques, such as positron emission tomography (PET) or single-photon emission computed tomography (SPECT) including drug or substrate tissue distribution assays or in radioactive treatment of patients. The concentration of an isotope may be defined by an isotopic enrichment factor.

The terms "isotopologue" or "stable isotope" refers to a species that differs from a specific compound disclosed herein only in the isotopic composition thereof. The term "naturally occurring" refers to compounds having a natural abundance of a specified isotope or of all the isotopes in the compound. By contrast, the isotopologues described herein are not naturally occurring. Preferably, the compounds are enriched with nuclei, such as $^2H$, $^3H$, $^{13}C$, $^{14}C$, $^{16}O$, $^{18}O$ and/or $^{15}N$ nuclei. The term "isotopically enriched" means that the concentration of nuclei in the compound is above the typical value of natural abundance of said nuclei, preferably above at least 10% of natural abundance, more preferably above at least 25%, and even more preferably above at least 75% of its natural abundance and most preferably above at least 90% of its natural abundance. For any chemical structure(s) or reaction(s) described or disclosed, hydrogen atoms, which by convention are not shown, may be deuterium or tritium. In some instances a compound prepared by the processes described herein may be isotopically enriched in one or more of $^2H$ (deuterium, D), $^3H$ (tritium), $^{11}C$, $^{13}C$, $^{14}C$, and/or $^{15}N$. In certain embodiments, a compound prepared by the processes described herein may be isotopically enriched in one or more of $^2H$ (deuterium, D), $^3H$ (tritium), $^{11}C$, $^{13}C$, $^{14}C$, and/or $^{15}N$ such that one or more (e.g., 1, 2, 3, 4, 5, or 6 atoms in a specific compound) are isotopically enriched. In certain embodiments, provided is a composition comprising a compound prepared by the processes described herein, wherein at least about 90%, or at least about 92%, or at least about 94%, or at least about 95%, or at least about 96%, or at least about 97%, or at least about 98%, or at least about 99% of at least one atom at a specified position is isotopically labeled (e.g., with an isotope selected from $^2H$ (deuterium, D), $^3H$ (tritium), $^{11}C$, $^{13}C$, $^{14}C$, and/or $^{15}N$).

The natural abundance of various isotopes in nature has been approximated, for example, in the CRC Handbook of Chemistry and Physics, published by CRC Press, Inc. The most abundantly occurring form of carbon, the carbon-12 ($^{12}C$) isotope, is approximately 98.90% abundant in nature. The stable carbon-13 ($^{13}C$) isotope, by contrast, is only approximately 1.10% naturally abundant. The most abundantly occurring isotope of hydrogen (H) is approximately 99.985% abundant in nature. The isotope deuterium (H), by contrast, is only approximately 0.015% naturally abundant. Various isotopes of nitrogen and oxygen exist in nature, as well. For example, $^{14}N$ and $^{15}N$ are 99.63% and 0.37% naturally abundant, respectively; $^{16}O$, $^{17}O$ and $^{18}O$ are 99.76%, 0.04% and 0.20% naturally abundant, respectively.

The compounds described herein, may contain an asymmetric carbon atom, for example, as the result of four different substituents bound to a carbon atom, deuterium substitution or otherwise. As such, compounds as described herein can exist as either individual enantiomers, or mixtures of the two enantiomers. Compounds that contain more than one asymmetric carbon can exist as multiple diastereomers, with each having an associated enantiomer. Accordingly, a compound described herein unless expressly noted otherwise will include racemic mixtures, racemic mixtures of diastereomers, and also individual respective stereoisomers that are substantially free from another possible stereoisomer.

Methods of obtaining by purification or synthesis an individual diastereomer from a mixture of diastereomers are understood in the art and may be applied as practicable to final compounds or to starting material or intermediates described herein. Methods of obtaining by purification or synthesis an individual enantiomer from a racemic mixture are understood in the art and may be applied as practicable to final compounds or to starting material or intermediates.

Methods of Synthesis

Provided herein are methods for the synthesis of an important class of biological compounds, referred to as organic acids, in water without enzymes. In a specific embodiment, this disclosure relates to the synthesis of $^{13}$C-labeled metabolites through a novel reaction pathway that bypasses the currently employed enzymatic approaches. In one aspect, the methods of synthesis described herein allow for the formation of fumaroyl formate, α-ketoglutarate, isocitroyl formate and aconitoyl formate from pyruvate and glyoxylate and their derivatives. A subsequent oxidative decarboxylation generates the metabolites fumarate, isocitrate, aconitate and related derivatives. The reactions also allow for the installation of rare isotopes at positions previously unavailable or prohibitively expensive. As one non-limiting example, $^{13}$Cl α-ketoglutarate, which has a list price of $12,000 per 10 milligrams (Medical Isotopes Inc., as of Jul. 27, 2018), can be synthesized using this method with less than $100 of labeled starting material. The methods of the present disclosure have high potential utility in pharmaceutical and materials chemistry.

Provided herein, in one aspect, is a method for reducing an aldol condensation compound, the method comprising (1) contacting an aldol nucleophile with an aldehydic electrophile to provide an aldol addition compound;

(2) dehydrating the aldol addition compound to provide an aldol condensation compound having an α,β-unsaturated bond; and (3) reducing the α,β-unsaturated bond in the aldol condensation compound by contacting the aldol condensation compound with the aldehydic electrophile, wherein the aldehydic electrophile is a reactant in step (1) and a reductant in step (3).

In one group of embodiments, the method involves reactions between nucleophiles and aldehydic elctrophiles having the following structures:

Nucleophile x' = CO$_2$R, CN, C(S)OR,
C(NR)OR, OR, SR, NR$_2$

R = hydrogen, or a substituted or unsubstituted alkyl group, or a heteroatom, or a carboxylate, amide or nitrile

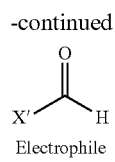

Electrophile x' = CO$_2$R, CN, C(S)OR,
C(NR)OR, OR, SR, NR$_2$.

In some embodiments, the aldehydic electrophile is of Formula (B):

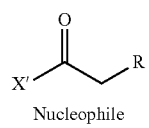

(B)

wherein X is selected from the group consisting of H, COOH, and C(=O)OC$_{1-12}$alkyl; and Y is H. In some embodiments, the nucleophile is an α-keto acid of Formula (A) as described herein.

In a further aspect, provided herein is a method for preparing an organic acid, the method comprising (1) contacting an α-keto acid with an aldehydic electrophile to provide an aldol addition compound;

(2) dehydrating the aldol addition compound to provide an aldol condensation compound having an α,β-unsaturated bond;

(3) reducing the α,β-unsaturated bond in the aldol condensation compound by contacting the aldol condensation compound with the aldehydic electrophile; and (4) oxidatively decarboxylating the reduced aldol condensation compound to provide the organic acid; or (5) reducing the keto group in the reduced aldol condensation compound to provide the organic acid; or (6) subjecting the reduced aldol condensation compound to reductive amination or transmination to provide the organic acid.

In some or any embodiments of the methods described above and below, the organic acid product is an organic acid derived from an α-keto acid. Through control of aldehyde equivalents (e.g., glyoxylic acid equivalents), as well as temperature, time and pH, the reaction progress can be optimized to favor a particular step along a reaction pathway, for example, as shown in FIG. 1, indicating in part, the aldol addition followed by the conjugate reduction rendering the aldol addition irreversible, and other steps. Typically, reaction temperatures may range from 0 to 200 degree centigrade, time may range from 5 minutes to one month, and pH may generally range from about 1 to about 13. Without being bound by any theory, it is believed that control of the reaction and output products are regulated primarily by chemical kinetics as a function of time and temperature.

In a sub-group of embodiments of the methods described above and below, provided herein is a method for the conversion of α-keto acids to organic acids thereof (diacids thereof), where the organic acids are represented by the structure of Formula (F) below, the method comprising (1) contacting an alpha keto acid of Formula (A) with an aldehydic electrophile of Formula (B)

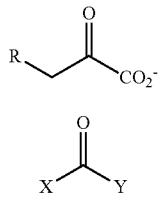
(A)

(B)

to provide an aldol addition compound of Formula (C)

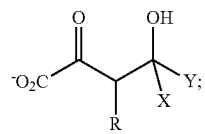
(C)

(2) dehydrating the compound of Formula (C) to provide an aldol condensation compound of Formula (D)

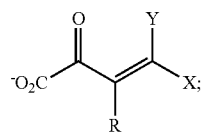
(D)

(3) reducing the compound of Formula (D) to provide a compound of Formula (E)

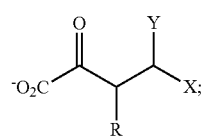
(E)

by contacting the compound of Formula (D) with the aldehydic electrophile; and
(4) oxidatively decarboxylating the compound of Formula (E) to provide an organic acid of Formula (F)

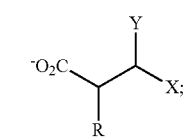
(F)

wherein
R is $C_{1-12}$alkyl, $C_{2-10}$heteroalkyl, $C_{6-20}$aryl, $C_{3-12}$heteroaryl, $C_{3-10}$cycloalkyl, $C_{2-10}$heterocyclyl, $C_{1-12}$alkyl-$C_{6-20}$aryl, $C_{1-12}$alkyl-$C_{3-12}$heteroaryl, $C_{1-12}$alkyl-$C_{3-10}$cycloalkyl, or $C_{1-12}$alkyl-$C_{2-10}$heterocyclyl, wherein alkyl, heteroalkyl, aryl, heteroaryl, cycloalkyl, and heterocyclyl are independently optionally substituted with one or more substituents selected from the group consisting of alkyl, alkenyl, alkynyl, alkoxy, acyl, amino, amido, amidino, aryl, azido, carbamoyl, carboxyl, carboxyl ester, cyano, guanidino, halo, haloalkyl, haloalkoxy, heteroalkyl, heteroaryl, heterocyclyl, hydroxy, hydrazino, imino, oxo, nitro, alkylsulfinyl, sulfonic acid, alkylsulfonyl, thiocyanate, thiol, thione, and combinations thereof;

X is selected from the group consisting of H, COOH, and C($=$O)O$C_{1-12}$alkyl; and Y is H.

In a sub-group of embodiments of the methods described above and below, provided herein is a method for the conversion of α-keto acids to organic acids thereof (amino acids thereof), where the organic acids are represented by the structure of Formula (G) below, the method comprising (1) contacting an alpha keto acid of Formula (A) with an aldehydic electrophile of Formula (B)

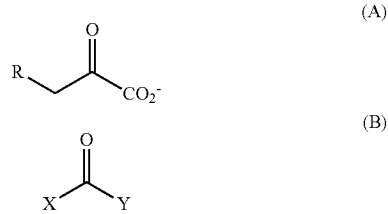
(A)

(B)

to provide an aldol addition compound of Formula (C)

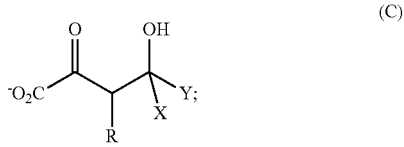
(C)

(2) dehydrating the compound of Formula (C) to provide an aldol condensation compound of Formula (D)

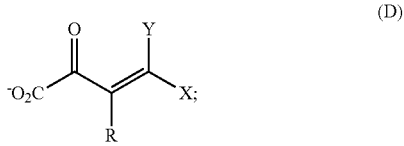
(D)

(3) reducing the compound of Formula (D) to obtain a compound of Formula (E)

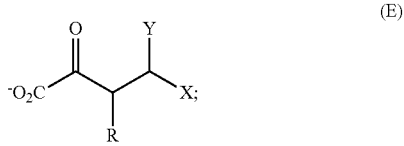
(E)

by contacting the compound of Formula (D) with the aldehydic electrophile; and
(6) subjecting the compound of Formula (E) to reductive amination or transamination to provide an organic acid of Formula (G)

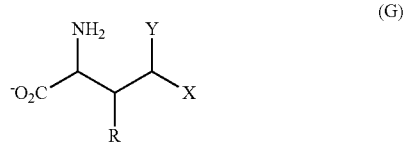

(G)

wherein
R is $C_{1-12}$alkyl, $C_{2-10}$heteroalkyl, $C_{6-20}$aryl, $C_{3-12}$heteroaryl, $C_{3-10}$cycloalkyl, $C_{2-10}$heterocyclyl, $C_{1-12}$alkyl-$C_{6-20}$aryl, $C_{1-12}$alkyl-$C_{3-12}$heteroaryl, $C_{1-12}$alkyl-$C_{3-10}$cycloalkyl, or $C_{1-12}$alkyl-$C_{2-10}$heterocyclyl, wherein alkyl, heteroalkyl, aryl, heteroaryl, cycloalkyl, and heterocyclyl are independently optionally substituted with one or more substituents selected from the group consisting of alkyl, alkenyl, alkynyl, alkoxy, acyl, amino, amido, amidino, aryl, azido, carbamoyl, carboxyl, carboxyl ester, cyano, guanidino, halo, haloalkyl, haloalkoxy, heteroalkyl, heteroaryl, heterocyclyl, hydroxy, hydrazino, imino, oxo, nitro, alkylsulfinyl, sulfonic acid, alkylsulfonyl, thiocyanate, thiol, thione, or combinations thereof;

X is selected from the group consisting of H, COOH, and $C(=O)OC_{1-12}$alkyl; and Y is H.

The reductive amination of the compound of Formula (E), step (6) above, is conducted in the presence of any suitable reductive amination reagent. In a specific embodiment, the reductive amination is conducted in the presence of sodium borohydride or sodium cyanoborohydride. In a further embodiment, the reductive amination is conducted under enzyme free conditions and in water. In some embodiments, the reductive amination is conducted in the presence of an amine comprising a radioisotope of nitrogen (e.g., ammonia with a radioisotope of nitrogen).

The transamination of the compound of Formula (E), step (6) above, is conducted in the presence of a nitrogen donor and a Lewis acid. In a specific embodiment, glycine is used as the nitrogen donor, and aluminum potassium sulfate (e.g., $AlK(SO_4)_2$) or potassium alum is used as a Lewis acid catalyst. Potassium alum is typically available in a dodecahydrate form (e.g., $AlK(SO_4)_2 \cdot 12\ H_2O$). In some embodiments, the transamination is conducted in the presence of an amine comprising a radioisotope of nitrogen (e.g., glycine with radioisotope of nitrogen). In a further embodiment, the transamination is conducted under enzyme free conditions and in water.

In a sub-group of embodiments of the methods described above and below, provided herein is a method for the conversion of α-keto acids to organic acids thereof (alpha-hydroxy diacids thereof), where the organic acids are represented by the structure of Formula (H) below, the method comprising (1) contacting an alpha keto acid of Formula (A) with an aldehydic electrophile of Formula (B)

(A)

(B)

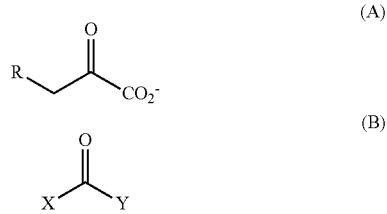

to provide an aldol addition compound of Formula (C)

(C)

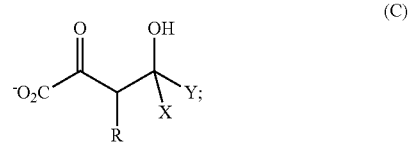

(2) dehydrating the compound of Formula (C) to provide an aldol condensation compound of Formula (D)

(D)

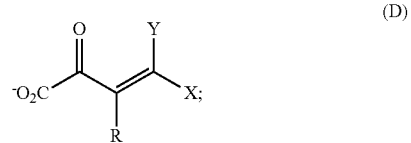

(3) reducing the compound of Formula (D) to provide a compound of Formula (E)

(E)

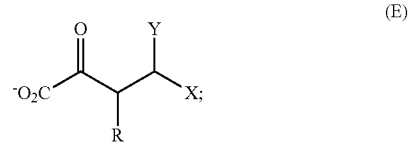

by contacting the compound of Formula (D) with the aldehydic electrophile; and (5) further reducing the compound of Formula (E) to provide an organic acid of Formula (H)

(H)

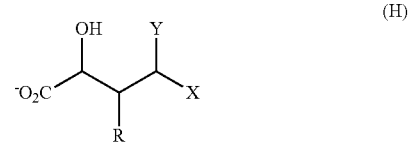

wherein
R is $C_{1-12}$alkyl, $C_{2-10}$heteroalkyl, $C_{6-20}$aryl, $C_{3-12}$heteroaryl, $C_{3-10}$cycloalkyl, $C_{2-10}$heterocyclyl, $C_{1-12}$alkyl-$C_{6-20}$aryl, $C_{1-12}$alkyl-$C_{3-12}$heteroaryl, $C_{1-12}$alkyl-$C_{3-10}$cycloalkyl, or $C_{1-12}$alkyl-$C_{2-10}$heterocyclyl, wherein alkyl, heteroalkyl, aryl, heteroaryl, cycloalkyl, and heterocyclyl are independently optionally substituted with one or more substituents selected from the group consisting of alkyl, alkenyl, alkynyl, alkoxy, acyl, amino, amido, amidino, aryl, azido, carbamoyl, carboxyl, carboxyl ester, cyano, guanidino, halo, haloalkyl, haloalkoxy, heteroalkyl, heteroaryl, heterocyclyl, hydroxy, hydrazino, imino, oxo, nitro, alkylsulfinyl, sulfonic acid, alkylsulfonyl, thiocyanate, thiol, thione, or combinations thereof;

X is selected from the group consisting of H, COOH, and $C(=O)OC_{1-12}$alkyl; and Y is H.

In an embodiment of the method described above, step (5), the reduction of a compound of Formula (E), is conducted in the presence of a metal hydride. Examples of such metal hydrides include and are not limited to sodium borohydride, lithium aluminum hydride, diisobutylaluminium hydride, L-selectride, diborane, or any other suitable metal hydride. In a specific embodiment, the metal hydride is sodium borohydride.

In a sub-group of embodiments of the methods described above and below, provided herein is a method for the conversion of α-keto acids to organic acids thereof, where the organic acids are represented by the structures of Formulas (L), (M), (N), or (O) below, the method comprising (1) contacting an alpha keto acid of Formula (A) with an aldehydic electrophile of Formula (B)

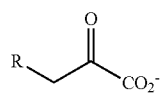
(A)

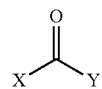
(B)

to provide an aldol addition compound of Formula (C)

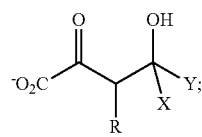
(C)

(1-1) contacting compound (C) with Compound (B) to provide a compound of Formula (J)

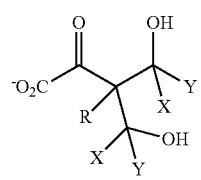
(J)

(2) dehydrating the compound of Formula (J) to provide a compound of Formula (K)

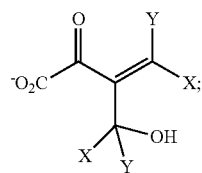
(K)

(3) reducing the compound of Formula (K) to provide a compound of Formula (L)

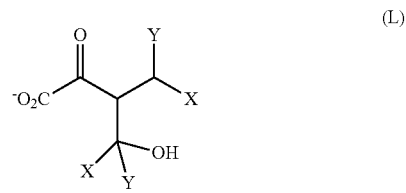
(L)

by contacting the compound of Formula (K) with the electrophilic aldehyde;

(2-1) dehydrating the compound of Formula (L) to provide a compound of Formula (M)

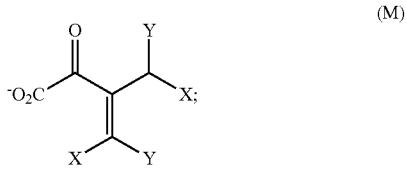
(M)

(3-1) reducing the compound of Formula (M) to obtain a compound of Formula (N)

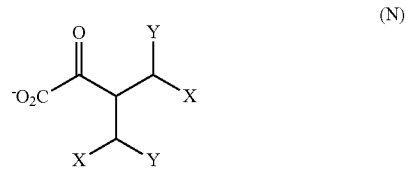
(N)

by contacting the compound of Formula (M) with the aldehydic electrophile; and (4) oxidatively decarboxylating the compound of Formula (N) to provide an organic acid of Formula (O)

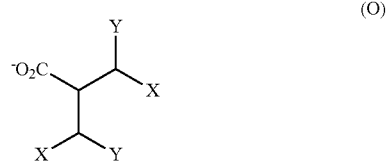
(O)

wherein
R is $C_{1-12}$alkyl, $C_{2-10}$heteroalkyl, $C_{6-20}$aryl, $C_{3-12}$heteroaryl, $C_{3-10}$cycloalkyl, $C_{2-10}$heterocyclyl, $C_{1-12}$alkyl-$C_{6-20}$aryl, $C_{1-12}$alkyl-$C_{3-12}$heteroaryl, $C_{1-12}$alkyl-$C_{3-10}$cycloalkyl, or $C_{1-12}$alkyl-$C_{2-10}$heterocyclyl, wherein alkyl, heteroalkyl, aryl, heteroaryl, cycloalkyl, and heterocyclyl are independently optionally substituted with one or more substituents selected from the group consisting of alkyl, alkenyl, alkynyl, alkoxy, acyl, amino, amido, amidino, aryl, azido, carbamoyl, carboxyl, carboxyl ester, cyano, guanidino, halo, haloalkyl, haloalkoxy, heteroalkyl, heteroaryl, heterocyclyl, hydroxy, hydrazino, imino, oxo, nitro, alkylsulfinyl, sulfonic acid, alkylsulfonyl, thiocyanate, thiol, thione, or combinations thereof;

X is selected from the group consisting of H, COOH, and
C(=O)OC$_{1-12}$alkyl; and
Y is H.

In some or any embodiments described above and below, in a nucleophile of Formula (A), R is optionally substituted C$_{1-12}$alkyl. In some of such embodiments R is C$_{1-12}$alkyl. In some of such embodiments, R is a C$_{1-6}$alkyl. In some of such embodiments, R is a C$_{1-5}$alkyl. In some of such embodiments, R is a C$_{1-4}$alkyl. In some of such embodiments, R is a C$_{1-2}$alkyl. In some of such embodiments, R is a straight chain alkyl. In some of such embodiments, R is a branched alkyl. In some of such embodiments, R is methyl and the nucleophile of Formula (A) is pyruvate.

In some or any embodiments described above and below, in a nucleophile of Formula (A), R is optionally substituted C$_{2-10}$heteroalkyl. In some or any embodiments described above and below, in a nucleophile of Formula (A), R is optionally substituted C$_{6-20}$aryl. In some or any embodiments described above and below, in a nucleophile of Formula (A), R is optionally substituted C$_{3-12}$heteroaryl. In some or any embodiments described above and below, in a nucleophile of Formula (A), R is optionally substituted C$_{3-10}$cycloalkyl. In some or any embodiments described above and below, in a nucleophile of Formula (A), R is optionally substituted C$_{2-10}$heterocyclyl. In some or any embodiments described above and below, in a nucleophile of Formula (A), R is optionally substituted C$_{1-12}$alkyl-C$_{6-20}$aryl. In some or any embodiments described above and below, in a nucleophile of Formula (A), R is optionally substituted C$_{1-12}$alkyl-C$_{3-12}$heteroaryl. In some or any embodiments described above and below, in a nucleophile of Formula (A), R is optionally substituted C$_{1-12}$alkyl-C$_{3-10}$cycloalkyl. In some or any embodiments described above and below, in a nucleophile of Formula (A), R is optionally substituted C$_{1-12}$ alkyl-C$_{2-10}$heterocyclyl. For any of the embodiments in this paragraph, alkyl, heteroalkyl, aryl, heteroaryl, cycloalkyl, and heterocyclyl are independently optionally substituted with one or more substituents selected from the group consisting of alkyl, alkenyl, alkynyl, alkoxy, acyl, amino, amido, amidino, aryl, azido, carbamoyl, carboxyl, carboxyl ester, cyano, guanidino, halo, haloalkyl, haloalkoxy, heteroalkyl, heteroaryl, heterocyclyl, hydroxy, hydrazino, imino, oxo, nitro, alkylsulfinyl, sulfonic acid, alkylsulfonyl, thiocyanate, thiol, thione, or combinations thereof. For any of the embodiments in this paragraph, alkyl, heteroalkyl, aryl, heteroaryl, cycloalkyl, and heterocyclyl are independently optionally substituted with one or more substituents selected from the group consisting of alkyl, alkoxy, halo, cyano, haloalkyl, haloalkoxy, amino, or hydroxy.

In some or any embodiments described above and below, the aldehydic electrophile is

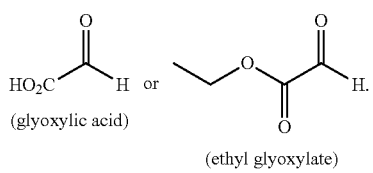

(glyoxylic acid)

(ethyl glyoxylate)

In some or any embodiments described above and below, the aldehydic electrophile is formaldehyde. In some or any embodiments described above and below, the aldehydic electrophile is glyoxylic acid. In any of these embodiments, the aldehydic electrophile is both, a reactant, and a reductant.

In some or any embodiments described above and below, the oxidative decarboxylation is conducted in the presence of a peracid. Examples of peracids include and are not limited to peracetic acid, meta-chloroperbenzoic acid, peroxymonosulfuric acid, peroxyphosphoric acid, sodium percarbonate, sodium perborate, and hydrogen peroxide. In some or any embodiments described above and below, the oxidative decarboxylation is conducted in the presence of hydrogen peroxide In some or any embodiments described above and below, the method for the synthesis of organic acids described herein (e.g., acids of Formula (F), (G), (L), (M), (N), (O)) from α-ketoacids is an enzyme-free method. In some or any embodiments described above and below, the method for the synthesis of organic acids described herein (e.g., acids of Formula (F), (G), (L), (M), (N), (O)) from α-ketoacids is a one-pot method. In some or any embodiments described above and below, the method for the synthesis of organic acids described herein (e.g., acids of Formula (F), (G), (L), (M), (N), (O)) from α-ketoacids is an iron-free method.

For any methods described herein, the methods comprise the use of reaction solvents. For any methods described herein, the methods comprise the use of a solvent selected from water, or a polar organic solvent, or a combination thereof. Polar organic solvents suitable for the methods described herein include and are not limited to acetonitrile, dimethyl formamide, tetrahydrofuran, methanol, ethanol, and dioxane.

In a specific embodiment, for any method described herein, the solvent is water.

For any method described herein, in some embodiments, the method steps are conducted at a reaction temperature of about room temperature. In other embodiments, the method steps are conducted at a reaction temperature ranging from about −10° C. to about 40° C. In further embodiments, the method steps are conducted at a reaction temperature ranging from about −20° C. to about 200° C., from about −20° C. to about 150° C., from about −20° C. to about 100° C., or from about −20° C. to about 50° C.

For any method described herein, in some embodiments, the solvent is water and further, the method steps are conducted at a pH that is a substantially neutral pH. In other embodiments, the method steps are conducted at a pH ranging from about 5 to about 9, or from about 6 to about 8. It will be understood that the reaction pH may be varied based on the stability of the reactants and/or products and may range from about 1 to about 13. In some embodiments the solvent is deuterated water.

For any method described herein, in some embodiments, the aldehydic electrophile comprises one or two radioisotopes of carbon.

For any method described herein, in some embodiments, the aldehydic electrophile is $^{13}$C2 labeled glyoxylic acid.

For any method described herein, in some embodiments, the organic acid product is labeled with one or more radioisotopes of carbon, nitrogen, hydrogen or oxygen, or a combination thereof.

In a specific embodiment, provided herein is a method for the production of α-keto acids and carboxylic acids thereof, in particular a method of producing $^2$H and/or $^{13}$C enriched-α-keto acids and carboxylic acids thereof. More particularly, the method relates to producing α-keto acids (of Formula (A)) by aldol addition/condensation of, for example, pyruvic acid or pyruvic acid derivatives with one or more equivalents of glyoxylic acid or glyoxylic acid derivatives (for example Formula B). A subsequent conjugate enone reduction by the glyoxylate renders the aldol reaction irreversible. Oxidation of the α-keto acid products, for example by hydrogen peroxide or $O_2$, produces a carboxylic acid derivative through loss of carbon dioxide. Advantageously, $^{13}C$ and $^2H$ isotopologues of organic acids, particularly of metabolic organic acids can be generated from inexpensive isotopically enriched pyruvic acid and glyoxylic acid derivatives. Methods for the production of the starting materials such as $^{13}C$-enriched and $^2H$-enriched pyruvic and glyoxylic acids are well established in the literature and/or the starting materials are commercially available.

In a specific instance, the processes described herein allow for the selective reduction of a conjugated enone to a keto group using glyoxylic acid as the reductant. The processes permit, in certain embodiments, improved selectivity of resulting compounds, improved control over isotope patterns in resulting compounds, improved yield, and compatibility in relatively safer and more common solvents and reaction conditions such as, for instance, water at about neutral pH.

For any method described herein, through control of the initial labelling of the starting reagents, any pattern of isotope enrichment can be achieved on the product α-keto acids and product organic acids thereof, as shown in, for example, Table A.

TABLE A

| Nucleophilic Reagent | Electrophilic Reagent | Non-limiting Example α-ketoacid product isotopologue | Non-limiting Example organic acid product isotopologue |
|---|---|---|---|
| 1-$^{13}$C-pyruvic acid | glyoxylic acid | 1-$^{13}$C-α-ketoglutaric acid | |
| 2-$^{13}$C-pyruvic acid | glyoxylic acid | 2-$^{13}$C-α-ketoglutaric acid | 1-$^{13}$C-succinic acid |
| 3-$^{13}$C-pyruvic acid | glyoxylic acid | 3-$^{13}$C-α-ketoglutaric acid | 2-$^{13}$C2-succinic acid |
| 2,3-$^{13}$C2-pyruvic acid | glyoxylic acid | 2,3-$^{13}$C2-α-ketoglutaric acid | 1,2-$^{13}$C2-succinic acid |
| 3-$^{13}$C-pyruvic acid | 1-$^{13}$C-glyoxylic acid | 3,5-$^{13}$C2-α-ketoglutaric acid | 1,3-$^{13}$C2-succinic acid |
| 2-$^{13}$C-pyruvic acid | 1-$^{13}$C-glyoxylic acid | 2,5-$^{13}$C2-α-ketoglutaric acid | 1,4-$^{13}$C2-succinic acid |
| 2,3-$^{13}$C2-pyruvic acid | 2-$^{13}$C-glyoxylic acid | 2,3,4-$^{13}$C3-α-ketoglutaric acid | 1,2,3-$^{13}$C3-succinic acid |
| 2,3-$^{13}$C2-pyruvic acid | 1-$^{13}$C-glyoxylic acid | 2,3,5-$^{13}$C3-α-ketoglutaric acid | 1,2,4-$^{13}$C3-succinic acid |
| 2,3-$^{13}$C2-pyruvic acid | 1,2-$^{13}$C2-glyoxylic acid | 2,3,4,5-$^{13}$C4-α-ketoglutaric acid | 1,2,3,4-$^{13}$C4-succinic acid |
| pyruvic acid | glyoxylic acid (1st eq) 1-$^{13}$C-glyoxylic acid (2nd eq) | 5-$^{13}$C-isocitroylformic acid | 1-$^{13}$C-isocitric acid |
| pyruvic acid | glyoxylic acid (1st eq) 2-$^{13}$C-glyoxylic acid (2nd eq) | 4-$^{13}$C-isocitroylformic acid | 2-$^{13}$C-isocitric acid |
| 3-$^{13}$C-pyruvic acid | glyoxylic acid (2 eq) | 3-$^{13}$C-isocitroylformic acid | 3-$^{13}$C-isocitric acid |
| pyruvic acid | glyoxylic acid (1st eq) 2-$^{13}$C-glyoxylic acid (2nd eq) | 6-$^{13}$C-isocitroylformic acid | 4-$^{13}$C-isocitric acid |
| pyruvic acid | 1-$^{13}$C-glyoxylic acid (1st eq) glyoxylic acid (2nd eq) | 7-$^{13}$C-isocitroylformic acid | 5-$^{13}$C-isocitric acid |
| 3-$^{13}$C-pyruvic acid | glyoxylic acid (2 eq) | 2-$^{13}$C-isocitroylformic acid | 6-$^{13}$C-isocitric acid |
| pyruvic acid | glyoxylic acid (1st eq) 1,2-$^{13}$C2-glyoxylic acid (2nd eq) | 4,5-$^{13}$C2-isocitroylformic acid | 1,2-$^{13}$C2-isocitric acid |
| 3-$^{13}$C-pyruvic acid | glyoxylic acid (1st eq) 1-$^{13}$C-glyoxylic acid (2nd eq) | 3,5-$^{13}$C2-isocitroylformic acid | 1,3-$^{13}$C2-isocitric acid |
| pyruvic acid | 2-$^{13}$C-glyoxylic acid (1st eq) 1-$^{13}$C-glyoxylic acid (2nd eq) | 5,6-$^{13}$C2-isocitroylformic acid | 1,4-$^{13}$C2-isocitric acid |
| pyruvic acid | 1-$^{13}$C-glyoxylic acid (1st eq) 1-$^{13}$C-glyoxylic acid (2nd eq) | 5,7-$^{13}$C2-isocitroylformic acid | 1,5-$^{13}$C2-isocitric acid |
| 2-$^{13}$C-pyruvic acid | 1-$^{13}$C-glyoxylic acid (1st eq) glyoxylic acid ($2^{nd}$ eq) | 2,5-$^{13}$C2-isocitroylformic acid | 1,6-$^{13}$C2-isocitric acid |
| 3-$^{13}$C-pyruvic acid | glyoxylic acid (1st eq) 2-$^{13}$C-glyoxylic acid (2nd eq) | 3,4-$^{13}$C2-isocitroylformic acid | 2,3-$^{13}$C2-isocitric acid |
| pyruvic acid | 2-$^{13}$C-glyoxylic acid (1st eq) 2-$^{13}$C-glyoxylic acid (2nd eq) | 4,6-$^{13}$C2-isocitroylformic acid | 2,4-$^{13}$C2-isocitric acid |
| pyruvic acid | 1-$^{13}$C-glyoxylic acid (1st eq) 2-$^{13}$C-glyoxylic acid (2nd eq) | 4,7-$^{13}$C2-isocitroylformic acid | 2,5-$^{13}$C2-isocitric acid |
| 2-$^{13}$C-pyruvic acid | glyoxylic acid (1st eq) 2-$^{13}$C-glyoxylic acid (2nd eq) | 2,4-$^{13}$C2-isocitroylformic acid | 2,6-$^{13}$C2-isocitric acid |
| 3-$^{13}$C-pyruvic acid | 2-$^{13}$C-glyoxylic acid (1st eq) glyoxylic acid ($2^{nd}$ eq) | 3,6-$^{13}$C2-isocitroylformic acid | 3,4-$^{13}$C2-isocitric acid |
| 3-$^{13}$C-pyruvic acid | 1-$^{13}$C-glyoxylic acid (1st eq) glyoxylic acid ($2^{nd}$ eq) | 3,7-$^{13}$C2-isocitroylformic acid | 3,5-$^{13}$C2-isocitric acid |

TABLE A-continued

| Nucleophilic Reagent | Electrophilic Reagent | Non-limiting Example α-ketoacid product isotopologue | Non-limiting Example organic acid product isotopologue |
|---|---|---|---|
| 2,3-$^{13}$C2-pyruvic acid | glyoxylic acid (1st eq) glyoxylic acid (2nd eq) | 2,3-$^{13}$C2-isocitroylformic acid | 3,6-$^{13}$C2-isocitric acid |
| pyruvic acid | 1,2-$^{13}$C-gyoxylic acid (1st eq) glyoxylic acid (2nd eq) | 6,7-$^{13}$C2-isocitroylformic acid | 4,5-$^{13}$C2-isocitric acid |
| 2-$^{13}$C-pyruvic acid | 2-$^{13}$C-glyoxylic acid (1st eq) glyoxylic acid (2nd eq) | 2,6-$^{13}$C2-isocitroylformic acid | 4,6-$^{13}$C2-isocitric acid |
| 2-$^{13}$C-pyruvic acid | 1-$^{13}$C-glyoxylic acid (1st eq) glyoxylic acid (2nd eq) | 2,7-$^{13}$C2-isocitroylformic acid | 5,6-$^{13}$C2-isocitric acid |
| 3-$^{13}$C-pyruvic acid | glyoxylic acid (1st eq) 1,2-$^{13}$C2-glyoxylic acid (2nd eq) | 3,4,5-$^{13}$C3-isocitroylformic acid | 1,2,3-$^{13}$C3-isocitric acid |
| 2-$^{13}$C-pyruvic acid | 1,2-$^{13}$C2-glyoxylic acid (1st eq) glyoxylic acid (2nd eq) | 2,6,7-$^{13}$C3-isocitroylformic acid | 4,5,6-$^{13}$C3-isocitric acid |
| 3-$^{13}$C-pyruvic acid | 2-$^{13}$C-glyoxylic acid (1st eq) 1,2-$^{13}$C2-glyoxylic acid (2nd eq) | 3,4,5,6-$^{13}$C4-isocitroylformic acid | 1,2,3,4-$^{13}$C4-isocitric acid |
| 2-$^{13}$C-pyruvic acid | 1-$^{13}$C-glyoxylic acid (1st eq) 1,2-$^{13}$C2-glyoxylic acid (2nd eq) | 2,4,5,7-$^{13}$C4-isocitroylformic acid | 1,2,5,6-$^{13}$C4-isocitric acid |
| 2,3-$^{13}$C2-pyruvic acid | 1,2-$^{13}$C-glyoxylic acid (1st eq) 1,2-$^{13}$C2-glyoxylic acid (2nd eq) | 2,3,4,5,6,7-$^{13}$C6-isocitroylformic acid | 1,2,3,4,5,6-$^{13}$C6-isocitric acid |

Only a small fraction of potential $^{13}$C-isotopic patterns has been previously reported for products such as α-ketoglutaric acid, isocitric acid and tricarballylic acid. No potential $^{13}$C-isotopic patterns have been previously reported for products such as 4-hydroxyketoglutaric acid and cis-aconitic acid. Some intermediates, for example isocitroyl formic acid are not natural compounds and have not been report in $^{13}$C-labeled or unlabeled forms.

Contemplated within the scope of embodiments described herein is the synthesis of any synthetic target comprising a carboxylic acid by starting with an α-keto acid in order to enable higher yielding syntheses under milder conditions. Additionally, the target carboxylic acid can be generated at the end of the synthesis by treatment of the α-keto acid with an oxidant, for example dilute aqueous hydrogen peroxide (or other oxidant).

Described herein is a method for the production of $^{2}$H and/or $^{13}$C enriched-α-keto acids and organic acids thereof as set forth in the instant disclosure.

Described herein is a method for the production of $^{2}$H and/or $^{13}$C enriched-α-keto acids and organic acids thereof comprising the step of:
  synthesizing metabolites by exchanging of one or more carboxylate groups (—CO$_2$—) for α-ketoacids (—C(O)CO$_2$—), which enables the synthesis of these metabolites to progress in water at neutral pH without enzyme catalysis to produce patterns of isotopic labelling not previously available.

Described herein is a method for the production of $^{2}$H and/or $^{13}$C enriched-α-keto acids and organic acids thereof comprising the steps of:
  combining a nucleophile with an electrophile under appropriate reaction conditions wherein the electrophile also serves as a reductant, and
  treating the resulting compounds with hydrogen peroxide (or other oxidant) to selectively yield, based on timing of the reaction, certain compounds useful for physiological testing of metabolism.

In such embodiments, the nucleophile may be pyruvic acid and the electrophile may be glyoxylic acid; and/or atoms of pyruvic acid and glyoxylic acid may be replaced with isotopes of carbon, oxygen, and hydrogen atoms in certain combinations to yield desirable isotopic patterns in resulting compounds; and/or certain resulting compounds may comprise isotopologues of α-ketoglutaric acid and/or isocitroylformic acid, or malic acid, succinic acid, fumaric acid, isocitric acid, cis/trans-aconitric acid, and/or tricarballylic acid.

Described herein is a method of manufacturing certain isotopic patterns of compounds useful for physiological testing of metabolism, the method comprises the steps of:
  combining isotopologues of pyruvic acid and glyoxylic acid in at least one reaction vessel at between 0 and 200 degrees centigrade, using primarily water as a solvent, at substantially neutral pH;
  monitoring the reaction progression by chemical composition and/or time;
  extracting certain desirable compounds from the at least one reaction vessel;
  combining the extracted compounds with hydrogen peroxide (or other oxidant) to yield desirable isotopologue metabolites; and,
  purifying and packaging the isotopologue metabolites.

Described herein is a method of producing $^{2}$H and/or $^{13}$C enriched-α-keto acids and carboxylic acids thereof useful for physiological testing, the method comprises the steps of:
  conducting an aldol addition and/or condensation of pyruvic acid or pyruvic acid derivatives with one or more equivalents of glyoxylic acid or glyoxylic acid derivatives to provide a first compound;
  conducting on said first compound a conjugate enone reduction by glyoxylate, wherein such aldol reaction is thermodynamically irreversible yielding a second compound;
  conducting an oxidation reaction of such second compound by hydrogen peroxide or diatomic oxygen yielding a third compound comprising carboxylic acid derivatives having $^{13}C$ and $^2H$ isotope patterns; and purifying and packaging said third compound.

Compounds

In some embodiments, provided herein are compounds that are metabolites observed in abberrant pathways in cells (e.g., aberrant tricarboxylic acid (TCA) cycle in cancer cells). In some embodiments, the compounds are radioisotopically labeled and are useful in monitoring aberrant cell pathways (e.g., in cancer diagnostic assays) and/or for perturbing cell pathways (e.g., for therapeutic modulation of aberrant cell pathways in cancer cells, or aberrant cell pathways arising from pathogenic activity such as malaria or bacterial infections). Accordingly, within the scope of embodiments presented herein is the use of any compound described herein for the treatment of a disease or condition associated with metabolic irregularities caused by altered cell expression or pathogenic activity.

In another aspect, provided herein is an organic acid prepared by any method or process described herein. In some of such embodiments, the organic acid is $^2H$, $^{13}C$ or $^{14}C$ isotopically enriched. In further embodiments, the organic acid is $^2H$, $^3H$, $^{13}C$, $^{14}C$, or $^{15}N$ isotopically enriched.

Provided herein are isotoplogue metabolites prepared by any method or process described herein. Also provided is the use of the isotopologue metabolites as markers for metabolic flux analysis.

α-Ketoglutaric Acid Isotopologues

In certain embodiments, provided herein is at least one compound prepared by the methods described herein having the structure of Formula 1a-1 and accompanying text below:

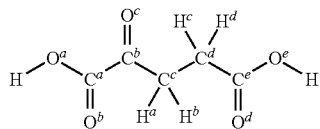

1a-1 or a salt or derivative thereof, wherein atoms of a synthesized compound described by the formula above may be selected as follows, either independently or in combination with any other atoms:

each of atoms $C^a$, $C^b$, $C^c$, $C^d$, and $C^e$ may be independently selected as $^{12}C$, $^{13}C$ or $^{14}C$, or a combination thereof;

each of atoms $H^a$, $H^b$, $H^c$, and $H^d$ may be independently selected as $^1H$, $^2H$ or $^3H$, or a combination thereof;

each of atoms $O^a$, $O^b$, $O^c$, $O^d$, and $O^e$ may be independently selected as $^{16}O$ or $^{18}O$, or a combination thereof.

It is understood that the following compounds have been previously reported or exist in isolatable quantities in nature:

α-ketoglutaric acid with natural isotopic ratios (unlabeled), 1,2-$^{13}C_2$-α-ketoglutaric acid, 2,3-$^{13}C_2$-α-ketoglutaric acid, 3,4-$^{13}C_2$-α-ketoglutaric acid, 4,5-$^{13}C_2$-α-ketoglutaric acid, 1,3,4-$^{13}C3$-α-ketoglutaric acid, 3,4,5-$^{13}C3$-α-ketoglutaric acid, 1,2,3,4-$^{13}C_2$-α-ketoglutaric acid, and 1,2,3,4,5-$^{13}C_2$-α-ketoglutaric acid.

In certain embodiments, the $^{13}C$ isotopic labels of compounds prepared by the methods described herein have the following patterns:

TABLE 1

| dilabeled | trilabeled | tetralabeled |
|---|---|---|
| 1,3-$^{13}C2$-α-ketoglutaric acid | 1,2,3-$^{13}C3$-α-ketoglutaric acid | 1,2,3,5-$^{13}C4$-α-ketoglutaric acid |
| 1,4-$^{13}C2$-α-ketoglutaric acid | 1,2,4-$^{13}C3$-α-ketoglutaric acid | 1,3,4,5-$^{13}C4$-α-ketoglutaric acid |
| 1,5-$^{13}C2$-α-ketoglutaric acid | 1,2,5-$^{13}C3$-α-ketoglutaric acid | 2,3,4,5-$^{13}C4$-α-ketoglutaric acid |
| 2,4-$^{13}C2$-α-ketoglutaric acid | 1,3,5-$^{13}C3$-α-ketoglutaric acid | |
| 2,5-$^{13}C2$-α-ketoglutaric acid | 1,4,5-$^{13}C3$-α-ketoglutaric acid | |
| 3,5-$^{13}C2$-α-ketoglutaric acid | 2,4,5-$^{13}C3$-α-ketoglutaric acid | |

2-Hydroxyglutaric Acid Isotopologues

In certain embodiments, at least one compound prepared by the methods described herein comprises the following, described in Formula 1a-2 and/or Formula 1b-2 and accompanying text below:

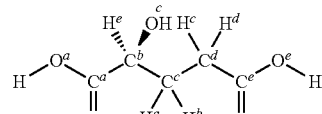

1a-2

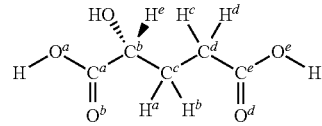

1b-2 or a salt or derivative thereof, wherein atoms of a synthesized compound described by the formula above may be selected as follows, either independently or in combination with any other atoms:

each of atoms $C^a$, $C^b$, $C^c$, $C^d$, and $C^e$ may be independently selected as $^{12}C$, $^{13}C$ or $^{14}C$, or a combination thereof;

each of atoms $H^a$, $H^b$, $H^c$, $H^d$, and $H^e$ may be independently selected as $^1H$ or $^2H$, or a combination thereof;

each of atoms $O^a$, $O^b$, $O^c$, $O^d$, and $O^e$ may be independently selected as $^{16}O$ or $^{18}O$, or a combination thereof.

It is understood that the following compounds have been previously reported or exist in isolatable quantities in nature: hydroxyglutaric acid with natural isotopic ratios (unlabeled), (RS)-1-$^{13}C1$-2-hydroxyglutaric acid, (RS)-1,2,3,4-$^{13}C4$-2-hydroxyglutaric acid, (R)-1,2,3,4-$^{13}C_{4-2}$-hydroxyglutaric acid, and (R)-1,2,3,4,5-$^{13}C_{5-2}$-hydroxyglutaric acid In one embodiment, the $^{13}C$ isotopic labels of compounds prepared by the methods described herein have the patterns below. Except for any isomers noted as excluded above, each compound listing includes all enantiomers and diastereomers independently and in combination. In one embodiment, provided is a compound as named in Table 2, or a salt, stereoisomer or mixture of stereoisomers thereof. In some embodiments, the compound of Table 2, or a salt, stereoisomer or mixture of stereoisomers thereof, is provided by a method disclosed herein.

TABLE 2

| monolabeled | dilabeled | trilabeled |
|---|---|---|
| 1-$^{13}$C1-2-hydroxyglutaric acid | 1,2-$^{13}$C2-2-hydroxyglutaric acid | 1,2,4-$^{13}$C3-2-hydroxyglutaric acid |
| 2-$^{13}$C1-2-hydroxyglutaric acid | 1,3-$^{13}$C2-2-hydroxyglutaric acid | 1,2,5-$^{13}$C3-2-hydroxyglutaric acid |
| 3-$^{13}$C1-2-hydroxyglutaric acid | 1,4-$^{13}$C2-2-hydroxyglutaric acid | 1,3,4-$^{13}$C3-2-hydroxyglutaric acid |
| 4-$^{13}$C1-2-hydroxyglutaric acid | 1,5-$^{13}$C2-2-hydroxyglutaric acid | 1,3,5-$^{13}$C3-2-hydroxyglutaric acid |
| 5-$^{13}$C1-2-hydroxyglutaric acid | 2,3-$^{13}$C2-2-hydroxyglutaric acid | 1,4,5-$^{13}$C3-2-hydroxyglutaric acid |
| tetralabeled 1,2,3,5-$^{13}$C4-2-hydroxyglutaric acid | 2,4-$^{13}$C2-2-hydroxyglutaric acid | 2,3,4-$^{13}$C3-2-hydroxyglutaric acid |
| 1,3,4,5-$^{13}$C4-2-hydroxyglutaric acid | 2,5-$^{13}$C2-2-hydroxyglutaric acid | 2,4,5-$^{13}$C3-2-hydroxyglutaric acid |
| 2,3,4,5-$^{13}$C4-2-hydroxyglutaric acid | 3,4-$^{13}$C2-2-hydroxyglutaric acid | 3,4,5-$^{13}$C3-2-hydroxyglutaric acid |
| | 3,5-$^{13}$C2-2-hydroxyglutaric acid | |
| | 4,5-$^{13}$C2-2-hydroxyglutaric acid | |

Oxopentenedioic Acid Isotopologues

In certain embodiments, at least one compound prepared by the methods described herein comprises the following, described in Formula 1a-3 and accompanying text below:

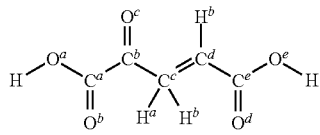

Formula 1a-3 or a salt or derivative thereof, wherein atoms of a synthesized compound described by the formula above may be selected as follows, either independently or in combination with any other atoms:

each of atoms $C^a$, $C^b$, $C^c$, $C^d$, and $C^e$ may be independently selected as $^{12}$C, $^{13}$C or $^{14}$C, or a combination thereof;

each of atoms $H^a$, and $H^b$ may be independently selected as $^1$H or $^2$H, or a combination thereof;

each of atoms $O^a$, $O^b$, $O^c$, $O^d$, and $O^e$ may be independently selected as $^{16}$O or $^{18}$O, or a combination thereof.

It is understood that the following compound has been previously reported or exists in isolatable quantities in nature: oxopentanedioic acid with natural isotopic ratios (unlabeled)

In one embodiment, the $^{13}$C isotopic labels of compounds prepared by the methods described herein have the patterns below. In one embodiment, provided is a compound as named in Table 3, or a salt, stereoisomer or mixture of stereoisomers thereof. In some embodiments, the compound of Table 3, or a salt, stereoisomer or mixture of stereoisomers thereof, is provided by a method disclosed herein.

TABLE 3

| monolabeled | dilabeled | trilabeled |
|---|---|---|
| 1-$^{13}$C1-oxopentenedioic acid | 1,2-$^{13}$C2-oxopentenedioic acid | 1,2,3-$^{13}$C3-oxopentenedioic acid |
| 2-$^{13}$C1-oxopentenedioic acid | 1,3-$^{13}$C2-oxopentenedioic acid | 1,2,4-$^{13}$C3-oxopentenedioic acid |
| 3-$^{13}$C1-oxopentenedioic acid | 1,4-$^{13}$C2-oxopentenedioic acid | 1,2,5-$^{13}$C3-oxopentenedioic acid |
| 4-$^{13}$C1-oxopentenedioic acid | 1,5-$^{13}$C2-oxopentenedioic acid | 1,3,4-$^{13}$C3-oxopentenedioic acid |
| 5-$^{13}$C1-oxopentenedioic acid | 2,3-$^{13}$C2-oxopentenedioic acid | 1,3,5-$^{13}$C3-oxopentenedioic acid |
| tetralabeled 1,2,3,4-$^{13}$C4-oxopentenedioic acid | 2,4-$^{13}$C2-oxopentenedioic acid | 1,4,5-$^{13}$C3-oxopentenedioic acid |
| 1,2,3,5-$^{13}$C4-oxopentenedioic acid | 2,5-$^{13}$C2-oxopentenedioic acid | 2,3,4-$^{13}$C3-oxopentenedioic acid |
| 1,3,4,5-$^{13}$C4-oxopentenedioic acid | 3,4-$^{13}$C2-oxopentenedioic acid | 2,4,5-$^{13}$C3-oxopentenedioic acid |
| 2,3,4,5-$^{13}$C4-oxopentenedioic acid | 3,5-$^{13}$C2-oxopentenedioic acid | 3,4,5-$^{13}$C3-oxopentenedioic acid |
| | 4,5-$^{13}$C2-oxopentenedioic acid | pentalabeled 1,2,3,4,5-$^{13}$C5-oxopentenedioic acid |

DL-4-Hydroxyketoglutaric Acid Isotopologues

In certain embodiments, at least one compound prepared by the methods described herein comprises the following, described in Formula 1a-4 and/or 1b-4 and accompanying test below:

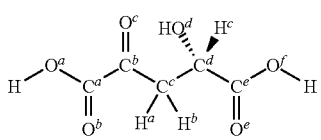

Formula 1a-4

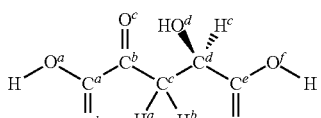

Formula 1b-4 or a salt or derivative thereof, wherein atoms of a synthesized compound described by the formula above may be selected as follows, either independently or in combination with any other atoms:

each of atoms $C^a$, $C^b$, $C^c$, $C^d$, and $C^e$ may be independently selected as $^{12}$C, $^{13}$C or $^{14}$C, or a combination thereof;

each of atoms $H^a$, $H^b$, and $H^c$ may be independently selected as $^1$H or $^2$H, or a combination thereof;

each of atoms $O^a$, $O^b$, $O^c$, $O^d$, $O^e$, and $O^f$ may be independently selected as $^{16}$O or $^{18}$O, or a combination thereof.

It is understood that the following compound has been previously reported or exists in isolatable quantities in nature: hydroxyketoglutaric acid with natural isotopic ratios (unlabeled).

In one embodiment, the $^{13}$C isotopic labels of compounds prepared by the methods described herein have the patterns below. Except for any isomers noted as excluded above, each compound listing includes all enantiomers and diastereomers independently and in combination. In one embodiment, provided is a compound as named in Table 4, or a salt, stereoisomer or mixture of stereoisomers thereof. In some embodiments, the compound of Table 4, or a salt, stereoisomer or mixture of stereoisomers thereof, is provided by a method disclosed herein.

TABLE 4

| monolabeled | dilabeled | trilabeled |
|---|---|---|
| 1-$^{13}$C1-4-hydroxy-ketoglutaric acid | 1,2-$^{13}$C2-4-hydroxy-ketoglutaric acid | 1,2,3-$^{13}$C3-4-hydroxy-ketoglutaric acid |
| 2-$^{13}$C1-4-hydroxy- | 1,3-$^{13}$C2-4-hydroxy- | 1,2,4-$^{13}$C3-4-hydroxy- |

TABLE 4-continued

| ketoglutaric acid | ketoglutaric acid | ketoglutaric acid |
|---|---|---|
| 3-$^{13}$C1-4-hydroxy-ketoglutaric acid | 1,4-$^{13}$C2-4-hydroxy-ketoglutaric acid | 1,2,5-$^{13}$C3-4-hydroxy-ketoglutaric acid |
| 4-$^{13}$C1-4-hydroxy-ketoglutaric acid | 1,5-$^{13}$C2-4-hydroxy-ketoglutaric acid | 1,3,4-$^{13}$C3-4-hydroxy-ketoglutaric acid |
| 5-$^{13}$C1-4-hydroxy-ketoglutaric acid | 2,3-$^{13}$C2-4-hydroxy-ketoglutaric acid | 1,3,5-$^{13}$C3-4-hydroxy-ketoglutaric acid |
| tetralabeled | 2,4-$^{13}$C2-4-hydroxy-ketoglutaric acid | 1,4,5-$^{13}$C3-4-hydroxy-ketoglutaric acid |
| 1,2,3,4-$^{13}$C4-4-hydroxy-ketoglutaric acid | 2,5-$^{13}$C2-4-hydroxy-ketoglutaric acid | 2,3,4-$^{13}$C3-4-hydroxy-ketoglutaric acid |
| 1,2,3,5-$^{13}$C4-4-hydroxy-ketoglutaric acid | 3,4-$^{13}$C2-4-hydroxy-ketoglutaric acid | 2,4,5-$^{13}$C3-4-hydroxy-ketoglutaric acid |
| 1,3,4,5-$^{13}$C4-4-hydroxy-ketoglutaric acid | 3,5-$^{13}$C2-4-hydroxy-ketoglutaric acid | 3,4,5-$^{13}$C3-4-hydroxy-ketoglutaric acid |
| 2,3,4,5-$^{13}$C4-4-hydroxy-ketoglutaric acid | 4,5-$^{13}$C2-4-hydroxy-ketoglutaric acid | |

2,4-Dihydroxyglutaric Acid Isotopologues, Also Known as 3-Deoxy-Pentaric Acid

In certain embodiments, at least one compound prepared by the methods described herein comprises the following, described in Formula 1a-5 and/or 1b-5 and/or 1c-5 and/or 1d-5 and accompanying text below:

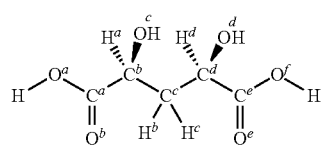

1a-1

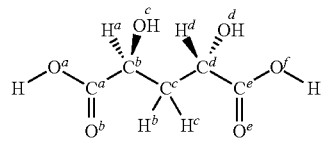

1b-1

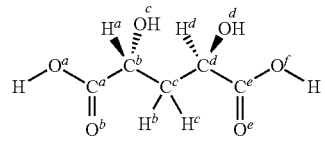

1c-1

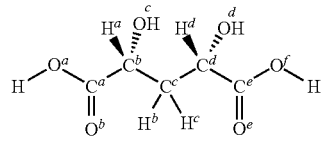

1d-1 or a salt or derivative thereof, wherein atoms of a synthesized compound described by the formula above may be selected as follows, either independently or in combination with any other atoms:

each of atoms $C^a$, $C^b$, $C^c$, $C^d$, and $C^e$, may be independently selected as $^{12}$C, $^{13}$C or $^{14}$C, or a combination thereof;

each of atoms $H^a$, $H^b$, $H^c$, and $H^d$ may be independently selected as $^1$H or $^2$H, or a combination thereof;

each of atoms $O^a$, $O^b$, $O^c$, $O^d$, $O^e$ and $O^f$ may be independently selected as $^{16}$O or $^{18}$O, or a combination thereof.

It is understood that the following compound has been previously reported or exists in isolatable quantities in nature: dihydroxyketoglutaric acid with natural isotopic ratios (unlabeled).

In one embodiment, the $^{13}$C isotopic labels of compounds prepared by the methods described herein have the patterns below. Except for any isomers noted as excluded above, each compound listing includes all enantiomers and diastereomers independently and in combination. In one embodiment, provided is a compound as named in Table 5, or a salt, stereoisomer or mixture of stereoisomers thereof. In some embodiments, the compound of Table 5, or a salt, stereoisomer or mixture of stereoisomers thereof, is provided by a method disclosed herein.

TABLE 5

| monolabeled | dilabeled | trilabeled |
|---|---|---|
| 1-$^{13}$C1-2,4-dihydroxyketoglutaric acid | 1,2-$^{13}$C2-2,4-dihydroxyketoglutaric acid | 1,2,3-$^{13}$C3-2,4-dihydroxyketoglutaric acid |
| 2-$^{13}$C1-2,4-dihydroxyketoglutaric acid | 1,3-$^{13}$C2-2,4-dihydroxyketoglutaric acid | 1,2,4-$^{13}$C3-2,4-dihydroxyketoglutaric acid |
| 3-$^{13}$C1-2,4-dihydroxyketoglutaric acid | 1,4-$^{13}$C2-2,4-dihydroxyketoglutaric acid | 1,2,5-$^{13}$C3-2,4-dihydroxyketoglutaric acid |
| 4-$^{13}$C1-2,4-dihydroxyketoglutaric acid | 1,5-$^{13}$C2-2,4-dihydroxyketoglutaric acid | 1,3,4-$^{13}$C3-2,4-dihydroxyketoglutaric acid |
| 5-$^{13}$C1-2,4-dihydroxyketoglutaric acid | 2,3-$^{13}$C2-2,4-dihydroxyketoglutaric acid | 1,3,5-$^{13}$C3-2,4-dihydroxyketoglutaric acid |
| tetralabeled | 2,4-$^{13}$C2-2,4-dihydroxyketoglutaric acid | 1,4,5-$^{13}$C3-2,4-dihydroxyketoglutaric acid |
| 1,2,3,4-$^{13}$C4-2,4-dihydroxyketoglutaric acid | 2,5-$^{13}$C2-2,4-dihydroxyketoglutaric acid | 2,3,4-$^{13}$C3-2,4-dihydroxyketoglutaric acid |
| 1,2,3,5-$^{13}$C4-2,4-dihydroxyketoglutaric acid | 3,4-$^{13}$C2-2,4-dihydroxyketoglutaric acid | 2,4,5-$^{13}$C3-2,4-dihydroxyketoglutaric acid |
| 1,3,4,5-$^{13}$C4-2,4-dihydroxyketoglutaric acid | 3,5-$^{13}$C2-2,4-dihydroxyketoglutaric acid | 3,4,5-$^{13}$C3-2,4-dihydroxyketoglutaric acid |
| 2,3,4,5-$^{13}$C4-4-hydroxyketoglutaric acid | 4,5-$^{13}$C2-4-hydroxy-ketoglutaric acid | |

Gamma-Hydroxyglutamic Acid Isotopologues

In certain embodiments, at least one compound prepared by the methods described herein comprises the following, described in Formula 1a-6 and/or 1b-6 and/or 1c-6 and/or 1d-6 and accompanying text below.

1a-6

1b-6

1c-6

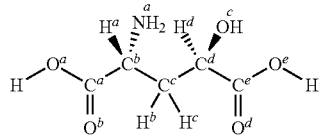

1d-6

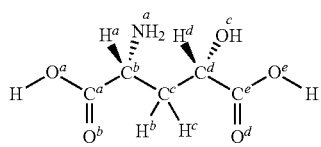

or a salt or derivative thereof, wherein atoms of a synthesized compound described by the formula above may be selected as follows, either independently or in combination with any other atoms:

each of atoms $C^a$, $C^b$, $C^c$, $C^d$, and $C^e$ may be independently selected as $^{12}C$, $^{13}C$ or $^{14}C$, or a combination thereof;

each of atoms $H^a$, $H^b$, $H^c$, and $H^d$ may be independently selected as $^{1}H$ or $^{2}H$, or a combination thereof;

each of atoms $O^a$, $O^b$, $O^c$, $O^d$, and $O^e$ may be independently selected as $^{16}O$ or $^{18}O$, or a combination thereof.

$N^a$ is independently $^{14}N$ or $^{15}N$

It is understood that the following compounds have been previously reported or exist in isolatable quantities in nature: gamma-hydroxyglutamic acid with natural isotopic ratios (unlabeled); 1-$^{14}$C1-gamma-hydroxyglutamic acid In one embodiment, the $^{13}C$ isotopic labels of compounds prepared by the methods described herein have the patterns below. Except for any isomers noted as excluded above, each compound listing includes all enantiomers and diastereomers independently and in combination. In one embodiment, provided is a compound as named in Table 6, or a salt, stereoisomer or mixture of stereoisomers thereof. In some embodiments, the compound of Table 6, or a salt, stereoisomer or mixture of stereoisomers thereof, is provided by a method disclosed herein.

TABLE 6

| monolabeled | dilabeled | trilabeled |
|---|---|---|
| 1-$^{13}$C1-gamma-hydroxyglutamate | 1,2-$^{13}$C2-gamma-hydroxyglutamate | 1,2,3-$^{13}$C3-gamma-hydroxyglutamate |
| 2-$^{13}$C1-gamma-hydroxyglutamate | 1,3-$^{13}$C2-gamma-hydroxyglutamate | 1,2,4-$^{13}$C3-gamma-hydroxyglutamate |
| 3-$^{13}$C1-gamma-hydroxyglutamate | 1,4-$^{13}$C2-gamma-hydroxyglutamate | 1,2,5-$^{13}$C3-gamma-hydroxyglutamate |
| 4-$^{13}$C1-gamma-hydroxyglutamate | 1,5-$^{13}$C2-gamma-hydroxyglutamate | 1,3,4-$^{13}$C3-gamma-hydroxyglutamate |
| 5-$^{13}$C1-gamma-hydroxyglutamate | 2,3-$^{13}$C2-gamma-hydroxyglutamate | 1,3,5-$^{13}$C3-gamma-hydroxyglutamate |
| tetralabeled | 2,4-$^{13}$C2-gamma-hydroxyglutamate | 1,4,5-$^{13}$C3-gamma-hydroxyglutamate |
| 1,2,3,4-$^{13}$C4-gamma-hydroxyglutamate | 2,5-$^{13}$C2-gamma-hydroxyglutamate | 2,3,4-$^{13}$C3-gamma-hydroxyglutamate |
| 1,2,3,5-$^{13}$C4-gamma-hydroxyglutamate | 3,4-$^{13}$C2-gamma-hydroxyglutamate | 2,4,5-$^{13}$C3-gamma-hydroxyglutamate |
| 1,3,4,5-$^{13}$C4-gamma-hydroxyglutamate | 3,5-$^{13}$C2-gamma-hydroxyglutamate | 3,4,5-$^{13}$C3-gamma-hydroxyglutamate |
| 2,3,4,5-$^{13}$C4-gamma-hydroxyglutamate | 4,5-$^{13}$C2-gamma-hydroxyglutamate | |

Fumaric Acid Isotopologues

In certain embodiments, at least one compound prepared by the methods described herein comprises the following, described in Formula 1a-7 and accompanying text below:

Formula 1a-7

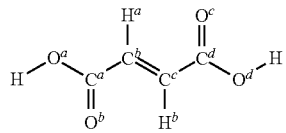

or a salt or derivative thereof, wherein atoms of a synthesized compound described by the formula above may be selected as follows, either independently or in combination with any other atoms:

each of atoms $C^a$, $C^b$, $C^c$, and $C^d$ may be independently selected as $^{12}C$, $^{13}C$ or $^{14}C$, or a combination thereof;

each of atoms $H^a$, and $H^b$ may be independently selected as $^{1}H$ or $^{2}H$, or a combination thereof;

each of atoms $O^a$, $O^b$, $O^c$, and $O^d$ may be independently selected as $^{16}O$ or $^{18}O$, or a combination thereof.

It is understood that the following compounds have been previously reported or exist in isolatable quantities in nature: fumaric acid with natural isotopic ratios (unlabeled), 1-$^{13}$C1-fumaric acid, 1,4-$^{13}$C2-fumaric acid, 2,3-$^{13}$C2-fumaric acid, and 1,2,3,4-$^{13}$C3-fumaric acid.

In one embodiment, the $^{13}C$ isotopic labels of compounds prepared by the methods described herein have the patterns below. In one embodiment, provided is a compound as named in Table 7, or a salt, stereoisomer or mixture of stereoisomers thereof. In some embodiments, the compound of Table 7, or a salt, stereoisomer or mixture of stereoisomers thereof, is provided by a method disclosed herein.

TABLE 7

| monolabeled | dilabeled | trilabeled |
|---|---|---|
| 2-$^{13}$C1-fumaric acid | 1,3-$^{13}$C2-fumaric acid | 1,2,3-$^{13}$C3-fumaric acid |
| 3-$^{13}$C1-fumaric acid | 2,4-$^{13}$C2-fumaric acid | 1,2,4-$^{13}$C3-fumaric acid |
| 4-$^{13}$C1-fumaric acid | 3,4-$^{13}$C2-fumaric acid | 1,3,4-$^{13}$C3-fumaric acid |
| | | 2,3,4-$^{13}$C3-fumaric acid |

Succinic Acid Isotopologues

In certain embodiments, at least one compound comprises the following, described in Formula 1a-8 and accompanying text below:

Formula 1a-8

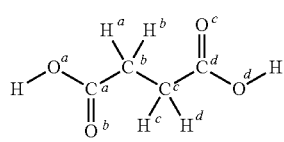

or a salt or derivative thereof, wherein atoms of a synthesized compound described by the formula above may be selected as follows, either independently or in combination with any other atoms:

each of atoms $C^a$, $C^b$, $C^c$, and $C^d$ may be independently selected as $^{12}C$, $^{13}C$ or $^{14}C$, or a combination thereof;

each of atoms $H^a$, $H^b$, $H^c$, and $H^d$ may be independently selected as $^{1}H$ or $^{2}H$, or a combination thereof;

each of atoms $O^a$, $O^b$, $O^c$, and $O^d$ may be independently selected as $^{16}O$ or $^{18}O$, or a combination thereof.

It is understood that the following compounds have been previously reported or exist in isolatable quantities in nature: succinic acid with natural isotopic ratios (unlabeled), 1-$^{13}$C1-succinic acid, 2-$^{13}$C1-succinic acid, 1,4-$^{13}$C2-succinic acid, 1,2-$^{13}$C2-succinic acid, 2,3-$^{13}$C2-succinic acid.

In one embodiment, the $^{13}$C isotopic labels of compounds prepared by the methods described herein have the patterns below. In one embodiment, provided is a compound as named in Table 8, or a salt, stereoisomer or mixture of stereoisomers thereof. In some embodiments, the compound of Table 8, or a salt, stereoisomer or mixture of stereoisomers thereof, is provided by a method disclosed herein.

TABLE 8

| dilabeled | trilabeled |
|---|---|
| 1,3-$^{13}$C2-succinic acid | 1,2,3-$^{13}$C3-succinic acid |
|  | 1,2,4-$^{13}$C3-succinic acid |

Malic Acid Isotopologues

In certain embodiments, at least one compound prepared by the methods described herein comprises the following, described in Formula 1a-9 and/or 1b-9 and accompanying text below:

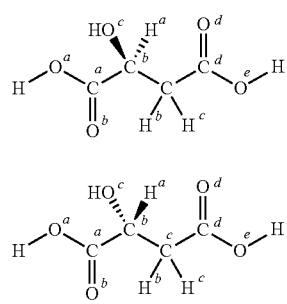

1a-9

1b-9 or a salt or derivative thereof, wherein atoms of a synthesized compound described by the formula above may be selected as follows, either independently or in combination with any other atoms:

each of atoms $C^a$, $C^b$, $C^c$, and $C^d$ may be independently selected as $^{12}$C, $^{13}$C or $^{14}$C, or a combination thereof;

each of atoms $H^a$, $H^b$, and $H^c$ may be independently selected as $^1$H, $^2$H or $^3$H, or a combination thereof;

each of atoms $O^a$, $O^b$, $O^c$, $O^d$, and $O^e$ may be independently selected as $^{16}$O or $^{18}$O, or a combination thereof.

It is understood that the following compounds have been previously reported or exist in isolatable quantities in nature: malic acid with natural isotopic ratios (unlabeled), 1-$^{13}$C1-malic acid, 2-$^{13}$C1-malic acid, 3-$^{13}$C1-malic acid, 4-$^{13}$C1-malic acid, 1,2-$^{13}$C2-(S)-malic acid, 1,4-$^{13}$C2-malic acid, 2,4-$^{13}$C2-malic acid, and 1,2,3,4-$^{13}$C4-malic acid.

In one embodiment, the $^{13}$C isotopic labels of compounds prepared by the methods described herein have the patterns below. Except for any isomers noted as excluded above, each compound listing includes all enantiomers and diastereomers independently and in combination. In one embodiment, provided is a compound as named in Table 9, or a salt, stereoisomer or mixture of stereoisomers thereof. In some embodiments, the compound of Table 9, or a salt, stereoisomer or mixture of stereoisomers thereof, is provided by a method disclosed herein.

TABLE 9

| dilabeled | trilabeled |
|---|---|
| 1,2-$^{13}$C2-(R)-malic acid | 1,2,3-$^{13}$C3-malic acid |
| 1,3-$^{13}$C2-malic acid | 1,2,4-$^{13}$C3-malic acid |
| 2,3-$^{13}$C2-malic acid | 1,3,4-$^{13}$C3-malic acid |
| 3,4-$^{13}$C2-malic acid | 2,3,4-$^{13}$C3-malic acid |

Isocitroylformic Acid Isotopologues

In certain embodiments, at least one compound prepared by the methods described herein comprises the following, described in Formula 1a-10 and/or 1b-10 and/or 1c-10 and/or 1d-10 and accompanying text below:

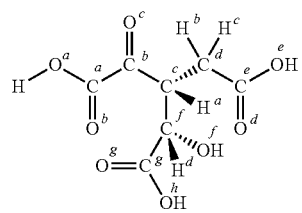

1a-10

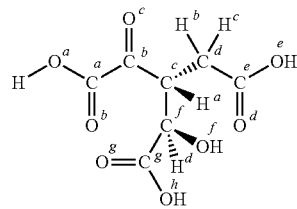

1b-10

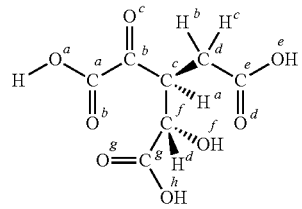

1c-10

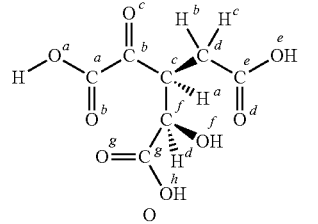

1d-10

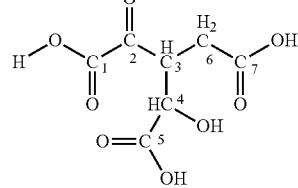

carbon numbering scheme used herein or a salt or derivative thereof, wherein atoms of a synthesized compound described by the formula above may be selected as follows, either independently or in combination with any other atoms:

35 each of atoms $C^a$, $C^b$, $C^c$, $C^d$, $C^e$, $C^f$, and $C^g$ may be independently selected as $^{12}C$, $^{13}C$ or $^{14}C$, or a combination thereof;

each of atoms $H^a$, $H^b$, $H^c$ and $H^d$ may be independently selected as $^{1}H$, $^{2}H$ or $^{3}H$, or a combination thereof;

each of atoms $O^a$, $O^b$, $O^c$, $O^d$, $O^e$, $O^f$, $O^g$ and $O^h$ may be independently selected as $^{16}O$ or $^{18}O$, or a combination thereof.

In one embodiment, the $^{13}C$ isotopic labels of compounds prepared by the methods described herein have the patterns below. Except for any isomers noted as excluded above, each compound listing includes all enantiomers and diastereomers independently and in combination. In one embodiment, provided is a compound as named in Table 10, or a salt, stereoisomer or mixture of stereoisomers thereof. In some embodiments, the compound of Table 10, or a salt, stereoisomer or mixture of stereoisomers thereof, is provided by a method disclosed herein.

TABLE 10

| unlabeled | trilabeled | tetralabeled |
|---|---|---|
| 1,2,3,4,5,6,7-$^{12}$C7-isocitroylformic acid | 1,2,3-$^{13}$C3-isocitroylformic acid | 1,2,3,4-$^{13}$C4-isocitroylformic acid |
| monolabeled | 1,2,4-$^{13}$C3-isocitroylformic acid | 1,2,3,5-$^{13}$C4-isocitroylformic acid |
| 1-$^{13}$C1-isocitroylformic acid | 1,2,5-$^{13}$C3-isocitroylformic acid | 1,2,3,6-$^{13}$C4-isocitroylformic acid |
| 2-$^{13}$C1-isocitroylformic acid | 1,2,6-$^{13}$C3-isocitroylformic acid | 1,2,3,7-$^{13}$C4-isocitroylformic acid |
| 3-$^{13}$C1-isocitroylformic acid | 1,2,7-$^{13}$C3-isocitroylformic acid | 1,2,4,5-$^{13}$C4-isocitroylformic acid |
| 4-$^{13}$C1-isocitroylformic acid | 1,3,4-$^{13}$C3-isocitroylformic acid | 1,2,4,6-$^{13}$C4-isocitroylformic acid |
| 5-$^{13}$C1-isocitroylformic acid | 1,3,5-$^{13}$C3-isocitroylformic acid | 1,2,4,7-$^{13}$C4-isocitroylformic acid |
| 6-$^{13}$C1-isocitroylformic acid | 1,3,6-$^{13}$C3-isocitroylformic acid | 1,2,5,6-$^{13}$C4-isocitroylformic acid |
| 7-$^{13}$C1-isocitroylformic acid | 1,3,7-$^{13}$C3-isocitroylformic acid | 1,2,5,7-$^{13}$C4-isocitroylformic acid |
| dilabeled | 1,4,5-$^{13}$C3-isocitroylformic acid | 1,2,6,7-$^{13}$C4-isocitroylformic acid |
| 1,2-$^{13}$C2-isocitroylformic acid | 1,4,6-$^{13}$C3-isocitroylformic acid | 1,3,4,5-$^{13}$C4-isocitroylformic acid |
| 1,3-$^{13}$C2-isocitroylformic acid | 1,4,7-$^{13}$C3-isocitroylformic acid | 1,3,4,6-$^{13}$C4-isocitroylformic acid |
| 1,4-$^{13}$C2-isocitroylformic acid | 1,5,6-$^{13}$C3-isocitroylformic acid | 1,3,6,7-$^{13}$C4-isocitroylformic acid |
| 1,5-$^{13}$C2-isocitroylformic acid | 1,5,7-$^{13}$C3-isocitroylformic acid | 1,4,5,6-$^{13}$C4-isocitroylformic acid |
| 1,6-$^{13}$C2-isocitroylformic acid | 1,6,7-$^{13}$C3-isocitroylformic acid | 1,4,5,7-$^{13}$C4-isocitroylformic acid |
| 1,7-$^{13}$C2-isocitroylformic acid | 2,3,4-$^{13}$C3-isocitroylformic acid | 1,4,6,7-$^{13}$C4-isocitroylformic acid |
| 2,3-$^{13}$C2-isocitroylformic acid | 2,3,5-$^{13}$C3-isocitroylformic acid | 1,5,6,7-$^{13}$C4-isocitroylformic acid |
| 2,4-$^{13}$C2-isocitroylformic acid | 2,3,6-$^{13}$C3-isocitroylformic acid | pentalabeled |
| 2,5-$^{13}$C2-isocitroylformic acid | 2,3,7-$^{13}$C3-isocitroylformic acid | 1,2,3,4,5-$^{13}$C5-isocitroylformic acid |
| 2,6-$^{13}$C2-isocitroylformic acid | 3,4,5-$^{13}$C3-isocitroylformic acid | 1,2,3,4,6-$^{13}$C5-isocitroylformic acid |
| 2,7-$^{13}$C2-isocitroylformic acid | 3,4,6-$^{13}$C3-isocitroylformic acid | 1,2,3,4,7-$^{13}$C5-isocitroylformic acid |
| 3,4-$^{13}$C2-isocitroylformic acid | 3,4,7-$^{13}$C3-isocitroylformic acid | 1,2,3,5,6-$^{13}$C5-isocitroylformic acid |
| 3,5-$^{13}$C2-isocitroylformic acid | 3,5,6-$^{13}$C3-isocitroylformic acid | 1,2,3,5,7-$^{13}$C5-isocitroylformic acid |
| 3,6-$^{13}$C2-isocitroylformic acid | 3,5,7-$^{13}$C3-isocitroylformic acid | 1,2,3,6,7-$^{13}$C5-isocitroylformic acid |
| 3,7-$^{13}$C2-isocitroylformic acid | 3,6,7-$^{13}$C3-isocitroylformic acid | 1,3,4,5,6-$^{13}$C5-isocitroylformic acid |
| 4,5-$^{13}$C2-isocitroylformic acid | 4,5,6-$^{13}$C3-isocitroylformic acid | 1,3,4,5,7-$^{13}$C5-isocitroylformic acid |
| 4,6-$^{13}$C2-isocitroylformic acid | 4,5,7-$^{13}$C3-isocitroylformic acid | 1,3,4,6,7-$^{13}$C5-isocitroylformic acid |
| 4,7-$^{13}$C2-isocitroylformic acid | 4,6,7-$^{13}$C3-isocitroylformic acid | 1,4,5,6,7-$^{13}$C5-isocitroylformic acid |
| 5,6-$^{13}$C2- | | |

36

TABLE 10-continued

| isocitroylformic acid 5,7-$^{13}$C2-isocitroylformic acid 6,7-$^{13}$C2-isocitroylformic acid | isocitroylformic acid 5,6,7-$^{13}$C3-isocitroylformic acid heptalabeled 1,2,3,4,5,6,7-$^{13}$C7-isocitroylformic acid | hexalabeled 1,2,3,4,5,6-$^{13}$C6-isocitroylformic acid 1,2,3,4,5,7-$^{13}$C6-isocitroylformic acid 1,3,4,5,6,7-$^{13}$C6-isocitroylformic acid |

Isocitric Acid Isotopologues

In certain embodiments, at least one compound prepared by the methods described herein comprises the following, described in Formula 1a-11 and/or 1b-11 and/or 1c-11 and/or 1d-11 and accompanying text below:

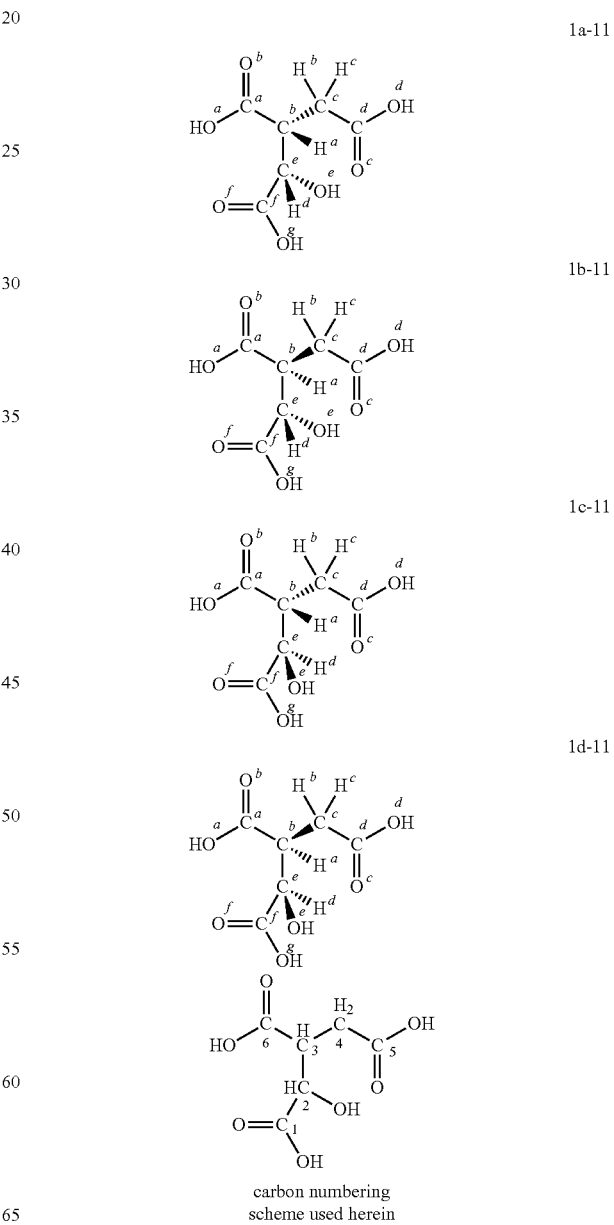

carbon numbering scheme used herein or a salt or derivative thereof, wherein atoms of a synthesized compound described by the formula above may be selected as follows, either independently or in combination with any other atoms:

each of atoms $C^a$, $C^b$, $C^c$, $C^d$, $C^e$, and $C^f$ may be independently selected as $^{12}C$, $^{13}C$ or $^{14}C$, or a combination thereof;

each of atoms $H^a$, $H^b$, $H^c$ and $H^d$ may be independently selected as $^1H$, $^2H$ or $^3H$, or a combination thereof;

each of atoms $O^a$, $O^b$, $O^c$, $O^d$, $O^e$, Of, and $O^g$ may be independently selected as $^{16}O$ or $^{18}O$, or a combination thereof.

It is understood that the following compounds have been previously reported or exist in isolatable quantities in nature: isocitric acid with natural isotopic ratios (unlabeled), 1-$^{13}C1$-isocitric acid, 4-$^{13}C1$-isocitric acid, 5-$^{13}C1$-isocitric acid, 6-$^{13}C1$-isocitric acid, 1,4,5-$^{13}C3$-isocitric acid.

In one embodiment, the $^{13}C$ isotopic labels of compounds prepared by the methods described herein have the patterns below. Except for any isomers noted as excluded above, each compound listing includes all enantiomers and diastereomers independently and in combination. In one embodiment, provided is a compound as named in Table 11, or a salt, stereoisomer or mixture of stereoisomers thereof. In some embodiments, the compound of Table 11, or a salt, stereoisomer or mixture of stereoisomers thereof, is provided by a method disclosed herein.

TABLE 11

| monolabeled | trilabeled | tetralabeled |
|---|---|---|
| 2-$^{13}C1$-isocitric acid | 1,2,3-$^{13}C3$-isocitric acid | 1,2,3,4-$^{13}C4$-isocitric acid |
| 3-$^{13}C1$-isocitric acid | 1,2,4-$^{13}C3$-isocitric acid | 1,2,3,5-$^{13}C4$-isocitric acid |
| dilabeled | 1,2,5-$^{13}C3$-isocitric acid | 1,2,3,6-$^{13}C4$-isocitric acid |
| 1,2-$^{13}C2$-isocitric acid | 1,2,6-$^{13}C3$-isocitric acid | 1,2,4,5-$^{13}C4$-isocitric acid |
| 1,3-$^{13}C2$-isocitric acid | 1,3,4-$^{13}C3$-isocitric acid | 1,2,4,6-$^{13}C4$-isocitric acid |
| 1,4-$^{13}C2$-isocitric acid | 1,3,5-$^{13}C3$-isocitric acid | 1,2,5,6-$^{13}C4$-isocitric acid |
| 1,5-$^{13}C2$-isocitric acid | 1,3,6-$^{13}C3$-isocitric acid | 1,3,4,5-$^{13}C4$-isocitric acid |
| 1,6-$^{13}C2$-isocitric acid | 1,4,6-$^{13}C3$-isocitric acid | 1,3,4,6-$^{13}C4$-isocitric acid |
| 2,3-$^{13}C2$-isocitric acid | 1,5,6-$^{13}C3$-isocitric acid | 1,4,5,6-$^{13}C4$-isocitric acid |
| 2,4-$^{13}C2$-isocitric acid | 2,3,4-$^{13}C3$-isocitric acid | pentalabeled |
| 2,5-$^{13}C2$-isocitric acid | 2,3,5-$^{13}C3$-isocitric acid | 1,2,3,4,5-$^{13}C5$-isocitric acid |
| 2,6-$^{13}C2$-isocitric acid | 2,3,6-$^{13}C3$-isocitric acid | 1,2,3,4,6-$^{13}C5$-isocitric acid |
| 3,4-$^{13}C2$-isocitric acid | 3,4,5-$^{13}C3$-isocitric acid | 1,2,3,5,6-$^{13}C5$-isocitric acid |
| 3,5-$^{13}C2$-isocitric acid | 3,4,6-$^{13}C3$-isocitric acid | 1,3,4,5,6-$^{13}C5$-isocitric acid |
| 3,6-$^{13}C2$-isocitric acid | 3,5,6-$^{13}C3$-isocitric acid | hexalabeled |
| 4,5-$^{13}C2$-isocitric acid | 4,5,6-$^{13}C3$-isocitric acid | 1,2,3,4,5,6-$^{13}C6$-isocitric acid |
| 4,6-$^{13}C2$-isocitric acid | | |
| 5,6-$^{13}C2$-isocitric acid | | |

Tricarballylic Acid Isotopologues

In certain embodiments, at least one compound prepared by the methods described herein comprises the following, described in Formula 1a-12 and/or 1b-12 and accompanying text below:

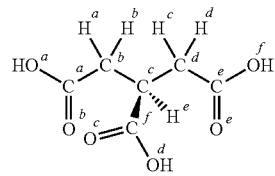

1a-12

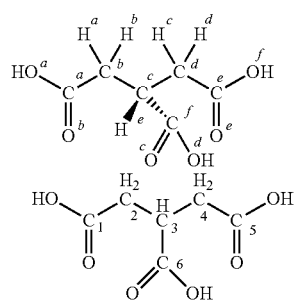

1b-12 carbon numbering scheme used herein or a salt or derivative thereof, wherein atoms of a synthesized compound described by the formula above may be selected as follows, either independently or in combination with any other atoms:

each of atoms $C^a$, $C^b$, $C^c$, $C^d$, $C^e$, and $C^f$ may be independently selected as $^{12}C$, $^{13}C$ or $^{14}C$, or a combination thereof;

each of atoms $H^a$, $H^b$, $H^c$, $H^d$ and $H^e$ may be independently selected as $^1H$, $^2H$ or $^3H$, or a combination thereof;

each of atoms $O^a$, $O^b$, $O^c$, $O^d$, and $O^e$ may be independently selected as $^{16}O$ or $^{18}O$, or a combination thereof.

It is understood that the following compounds have been previously reported or exist in isolatable quantities in nature: tricarballylic acid with natural isotopic ratios, 1-$^{14}C1$-tricarballylic acid, 2-$^{14}C1$-tricarballylic acid.

In one embodiment, the $^{13}C$ isotopic labels of compounds prepared by the methods described herein have the patterns below. Each compound listing includes both enantiomers independently and in combination. In one embodiment, provided is a compound as named in Table 12, or a salt, stereoisomer or mixture of stereoisomers thereof. In some embodiments, the compound of Table 12, or a salt, stereoisomer or mixture of stereoisomers thereof, is provided by a method disclosed herein.

TABLE 12

| monolabeled |
|---|
| 1-$^{13}C1$-tricarballylic acid |
| 2-$^{13}C1$-tricarballylic acid |
| 3-$^{13}C1$-tricarballylic acid |
| 4-$^{13}C1$-tricarballylic acid |
| 5-$^{13}C1$-tricarballylic acid |
| 6-$^{13}C1$-tricarballylic acid |
| dilabeled |
| 1,2-$^{13}C2$-tricarballylic acid |
| 1,3-$^{13}C2$-tricarballylic acid |
| 1,4-$^{13}C2$-tricarballylic acid |
| 1,5-$^{13}C2$-tricarballylic acid |
| 1,6-$^{13}C2$-tricarballylic acid |
| 2,3-$^{13}C2$-tricarballylic acid |
| 2,4-$^{13}C2$-tricarballylic acid |
| 2,5-$^{13}C2$-tricarballylic acid |

TABLE 12-continued 2,6-$^{13}$C2-tricarballylic acid
3,4-$^{13}$C2-tricarballylic acid
3,5-$^{13}$C2-tricarballylic acid
3,6-$^{13}$C2-tricarballylic acid
4,5-$^{13}$C2-tricarballylic acid
4,6-$^{13}$C2-tricarballylic acid
5,6-$^{13}$C2-tricarballylic acid trilabeled 1,2,3-$^{13}$C3-tricarballylic acid
1,2,4-$^{13}$C3-tricarballylic acid
1,2,5-$^{13}$C3-tricarballylic acid
1,2,6-$^{13}$C3-tricarballylic acid
1,3,4-$^{13}$C3-tricarballylic acid
1,3,5-$^{13}$C3-tricarballylic acid
1,3,6-$^{13}$C3-tricarballylic acid
1,4,5-$^{13}$C3-tricarballylic acid
1,4,6-$^{13}$C3-tricarballylic acid
1,5,6-$^{13}$C3-tricarballylic acid
2,3,4-$^{13}$C3-tricarballylic acid
2,3,5-$^{13}$C3-tricarballylic acid
2,3,6-$^{13}$C3-tricarballylic acid
3,4,5-$^{13}$C3-tricarballylic acid
3,4,6-$^{13}$C3-tricarballylic acid
3,5,6-$^{13}$C3-tricarballylic acid
4,5,6-$^{13}$C3-tricarballylic acid tetralabeled 1,2,3,4-$^{13}$C4-tricarballylic acid
1,2,3,5-$^{13}$C4-tricarballylic acid
1,2,3,6-$^{13}$C4-tricarballylic acid
1,2,4,5-$^{13}$C4-tricarballylic acid
1,2,4,6-$^{13}$C4-tricarballylic acid
1,2,5,6-$^{13}$C4-tricarballylic acid
1,3,4,5-$^{13}$C4-tricarballylic acid
1,3,4,6-$^{13}$C4-tricarballylic acid
1,4,5,6-$^{13}$C4-tricarballylic acid pentalabeled 1,2,3,4,5-$^{13}$C5-tricarballylic acid
1,2,3,4,6-$^{13}$C5-tricarballylic acid
1,2,3,5,6-$^{13}$C5-tricarballylic acid
1,3,4,5,6-$^{13}$C5-tricarballylic acid hexalabeled 1,2,3,4,5,6-$^{13}$C6-tricarballylic acid Trans-Aconitoyl Formic Acid Isotopologues In certain embodiments, at least one compound prepared by the methods described herein comprises the following, described in Formula 1a-13 and accompanying text below:

1a-13

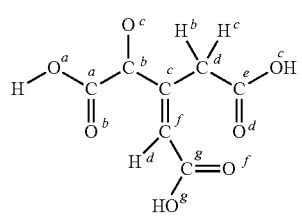

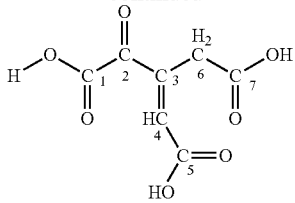

carbon numbering scheme used herein or a salt or derivative thereof, wherein atoms of a synthesized compound described by the formula above may be selected as follows, either independently or in combination with any other atoms:

each of atoms $C^a$, $C^b$, $C^c$, $C^d$, $C^e$, $C^f$, and $C^g$ may be independently selected as $^{12}$C, $^{13}$C or $^{14}$C, or a combination thereof;

each of atoms $H^a$, $H^b$, $H^c$ and $H^d$ may be independently selected as $^1$H, $^2$H or $^3$H, or a combination thereof;

each of atoms $O^a$, $O^b$, $O^c$, $O^d$, $O^e$, $O^f$, and $O^g$ may be independently selected as $^{16}$O or $^{18}$O, or a combination thereof.

In one embodiment, the $^{13}$C isotopic labels of compounds prepared by the methods described herein have the patterns below. In one embodiment, provided is a compound as named in Table 13, or a salt, stereoisomer or mixture of stereoisomers thereof. In some embodiments, the compound of Table 13, or a salt, stereoisomer or mixture of stereoisomers thereof, is provided by a method disclosed herein.

TABLE 13 unlabeled 1,2,3,4,5,6,7-$^{12}$C7-trans-aconitoyl formic acid monolabeled

1-$^{13}$C1-trans-aconitoyl formic acid
2-$^{13}$C1-trans-aconitoyl formic acid
3-$^{13}$C1-trans-aconitoyl formic acid
4-$^{13}$C1-trans-aconitoyl formic acid
5-$^{13}$C1-trans-aconitoyl formic acid
6-$^{13}$C1-trans-aconitoyl formic acid
7-$^{13}$C1-trans-aconitoyl formic acid dilabeled 1,2-$^{13}$C2-trans-aconitoyl formic acid
1,3-$^{13}$C2-trans-aconitoyl formic acid
1,4-$^{13}$C2-trans-aconitoyl formic acid
1,5-$^{13}$C2-trans-aconitoyl formic acid
1,6-$^{13}$C2-trans-aconitoyl formic acid
1,7-$^{13}$C2-trans-aconitoyl formic acid
2,3-$^{13}$C2-trans-aconitoyl formic acid
2,4-$^{13}$C2-trans-aconitoyl formic acid
2,5-$^{13}$C2-trans-aconitoyl formic acid TABLE 13-continued 2,6-$^{13}$C2-trans-aconitoyl formic acid
2,7-$^{13}$C2-trans-aconitoyl formic acid
3,4-$^{13}$C2-trans-aconitoyl formic acid
3,5-$^{13}$C2-trans-aconitoyl formic acid
3,6-$^{13}$C2-trans-aconitoyl formic acid
3,7-$^{13}$C2-trans-aconitoyl formic acid
4,5-$^{13}$C2-trans-aconitoyl formic acid
4,6-$^{13}$C2-trans-aconitoyl formic acid
4,7-$^{13}$C2-trans-aconitoyl formic acid
5,6-$^{13}$C2-trans-aconitoyl formic acid
5,7-$^{13}$C2-trans-aconitoyl formic acid
6,7-$^{13}$C2-trans-aconitoyl formic acid trilabeled 1,2,3-$^{13}$C3-trans-aconitoyl formic acid
1,2,4-$^{13}$C3-trans-aconitoyl formic acid
1,2,5-$^{13}$C3-trans-aconitoyl formic acid
1,2,6-$^{13}$C3-trans-aconitoyl formic acid
1,2,7-$^{13}$C3-trans-aconitoyl formic acid
1,3,4-$^{13}$C3-trans-aconitoyl formic acid
1,3,5-$^{13}$C3-trans-aconitoyl formic acid
1,3,6-$^{13}$C3-trans-aconitoyl formic acid
1,3,7-$^{13}$C3-trans-aconitoyl formic acid
1,4,5-$^{13}$C3-trans-aconitoyl formic acid
1,4,6-$^{13}$C3-trans-aconitoyl formic acid
1,4,7-$^{13}$C3-trans-aconitoyl formic acid
1,5,6-$^{13}$C3-trans-aconitoyl formic acid
1,5,7-$^{13}$C3-trans-aconitoyl formic acid
1,6,7-$^{13}$C3-trans-aconitoyl formic acid
2,3,4-$^{13}$C3-trans-aconitoyl formic acid
2,3,5-$^{13}$C3-trans-aconitoyl formic acid
2,3,6-$^{13}$C3-trans-aconitoyl formic acid
2,3,7-$^{13}$C3-trans-aconitoyl formic acid
3,4,5-$^{13}$C3-trans-aconitoyl formic acid
3,4,6-$^{13}$C3-trans-aconitoyl formic acid
3,4,7-$^{13}$C3-trans-aconitoyl formic acid
3,5,6-$^{13}$C3-trans-aconitoyl formic acid
3,5,7-$^{13}$C3-trans-aconitoyl formic acid
3,6,7-$^{13}$C3-trans-aconitoyl formic acid
4,5,6-$^{13}$C3-trans-aconitoyl formic acid
4,5,7-$^{13}$C3-trans-aconitoyl formic acid
4,6,7-$^{13}$C3-trans-aconitoyl formic acid
5,6,7-$^{13}$C3-trans-aconitoyl formic acid heptalabeled 1,2,3,4,5,6,7-$^{13}$C7-trans-aconitoyl formic acid tetralabeled 1,2,3,4-$^{13}$C4-trans-aconitoyl formic acid
1,2,3,5-$^{13}$C4-trans-aconitoyl formic acid
1,2,3,6-$^{13}$C4-trans-aconitoyl formic acid
1,2,3,7-$^{13}$C4-trans-aconitoyl formic acid
1,2,4,5-$^{13}$C4-trans-aconitoyl formic acid
1,2,4,6-$^{13}$C4-trans-aconitoyl formic acid
1,2,4,7-$^{13}$C4-trans-aconitoyl formic acid
1,2,5,6-$^{13}$C4-trans-aconitoyl formic acid
1,2,5,7-$^{13}$C4-trans-aconitoyl formic acid
1,2,6,7-$^{13}$C4-trans-aconitoyl formic acid
1,3,4,5-$^{13}$C4-trans-aconitoyl formic acid
1,3,4,6-$^{13}$C4-trans-aconitoyl formic acid
1,3,6,7-$^{13}$C4-trans-aconitoyl formic acid
1,4,5,6-$^{13}$C4-trans-aconitoyl formic acid
1,4,5,7-$^{13}$C4-trans-aconitoyl formic acid
1,4,6,7-$^{13}$C4-trans-aconitoyl formic acid
1,5,6,7-$^{13}$C4-trans-aconitoyl formic acid pentalabeled 1,2,3,4,5-$^{13}$C5-trans-aconitoyl formic acid
1,2,3,4,6-$^{13}$C5-trans-aconitoyl formic acid
1,2,3,4,7-$^{13}$C5-trans-aconitoyl formic acid
1,2,3,5,6-$^{13}$C5-trans-aconitoyl formic acid
1,2,3,5,7-$^{13}$C5-trans-aconitoyl formic acid
1,2,3,6,7-$^{13}$C5-trans-aconitoyl formic acid
1,3,4,5,6-$^{13}$C5-trans-aconitoyl formic acid
1,3,4,5,7-$^{13}$C5-trans-aconitoyl formic acid
1,3,4,6,7-$^{13}$C5-trans-aconitoyl formic acid
1,4,5,6,7-$^{13}$C5-trans-aconitoyl formic acid hexalabeled 1,2,3,4,5,6-$^{13}$C6-trans-aconitoyl formic acid
1,2,3,4,5,7-$^{13}$C6-trans-aconitoyl formic acid
1,3,4,5,6,7-$^{13}$C6-trans-aconitoyl formic acid

Cis-Aconitoyl Formic Acid Isotopologues

In certain embodiments, at least one compound prepared by the methods described herein comprises the following, described in Formula 1a-14 and accompanying text below:

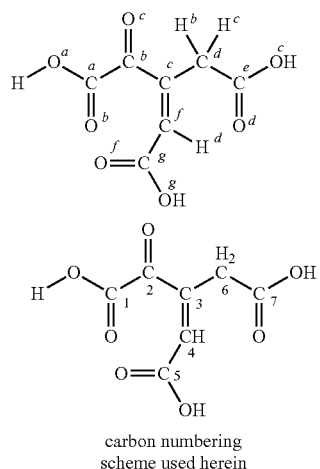

1a-14 carbon numbering scheme used herein or a salt or derivative thereof, wherein atoms of a synthesized compound described by the formula above may be selected as follows, either independently or in combination with any other atoms:

each of atoms $C^a$, $C^b$, $C^c$, $C^d$, $C^e$, $C^f$, and $C^g$ may be independently selected as $^{12}C$, $^{13}C$ or $^{14}C$, or a combination thereof;

each of atoms $H^a$, $H^b$, $H^c$ and $H^d$ may be independently selected as $^1H$, $^2H$ or $^3H$, or a combination thereof;

each of atoms $O^a$, $O^b$, $O^c$, $O^d$, $O^e$, $O^f$, and $O^g$ may be independently selected as $^{16}O$ or $^{18}O$, or a combination thereof.

In one embodiment, the $^{13}C$ isotopic labels of compounds prepared by the methods described herein have the patterns below. In one embodiment, provided is a compound as named in Table 14, or a salt, stereoisomer or mixture of stereoisomers thereof. In some embodiments, the compound of Table 14, or a salt, stereoisomer or mixture of stereoisomers thereof, is provided by a method disclosed herein.

TABLE 14

| unlabeled |
| --- |
| 1,2,3,4,5,6,7-$^{12}$C7-cis-aconitoyl formic acid |
| monolabeled |
| 1-$^{13}$C1-cis-aconitoyl formic acid |
| 2-$^{13}$C1-cis-aconitoyl formic acid |
| 3-$^{13}$C1-cis-aconitoyl formic acid |
| 4-$^{13}$C1-cis-aconitoyl formic acid |

TABLE 14-continued

| |
| --- |
| 5-$^{13}$C1-cis-aconitoyl formic acid |
| 6-$^{13}$C1-cis-aconitoyl formic acid |
| 7-$^{13}$C1-cis-aconitoyl formic acid |
| dilabeled |
| 1,2-$^{13}$C2-cis-aconitoyl formic acid |
| 1,3-$^{13}$C2-cis-aconitoyl formic acid |
| 1,4-$^{13}$C2-cis-aconitoyl formic acid |
| 1,5-$^{13}$C2-cis-aconitoyl formic acid |
| 1,6-$^{13}$C2-cis-aconitoyl formic acid |
| 1,7-$^{13}$C2-cis-aconitoyl formic acid |
| 2,3-$^{13}$C2-cis-aconitoyl formic acid |
| 2,4-$^{13}$C2-cis-aconitoyl formic acid |
| 2,5-$^{13}$C2-cis-aconitoyl formic acid |
| 2,6-$^{13}$C2-cis-aconitoyl formic acid |
| 2,7-$^{13}$C2-cis-aconitoyl formic acid |
| 3,4-$^{13}$C2-cis-aconitoyl formic acid |
| 3,5-$^{13}$C2-cis-aconitoyl formic acid |
| 3,6-$^{13}$C2-cis-aconitoyl formic acid |
| 3,7-$^{13}$C2-cis-aconitoyl formic acid |
| 4,5-$^{13}$C2-cis-aconitoyl formic acid |
| 4,6-$^{13}$C2-cis-aconitoyl formic acid |
| 4,7-$^{13}$C2-cis-aconitoyl formic acid |
| 5,6-$^{13}$C2-cis-aconitoyl formic acid |
| 5,7-$^{13}$C2-cis-aconitoyl formic acid |
| 6,7-$^{13}$C2-cis-aconitoyl formic acid |
| trilabeled |
| 1,2,3-$^{13}$C3-cis-aconitoyl formic acid |
| 1,2,4-$^{13}$C3-cis-aconitoyl formic acid |
| 1,2,5-$^{13}$C3-cis-aconitoyl formic acid |
| 1,2,6-$^{13}$C3-cis-aconitoyl formic acid |
| 1,2,7-$^{13}$C3-cis-aconitoyl formic acid |
| 1,3,4-$^{13}$C3-cis-aconitoyl formic acid |
| 1,3,5-$^{13}$C3-cis-aconitoyl formic acid |
| 1,3,6-$^{13}$C3-cis-aconitoyl formic acid |
| 1,3,7-$^{13}$C3-cis-aconitoyl formic acid |
| 1,4,5-$^{13}$C3-cis-aconitoyl formic acid |
| 1,4,6-$^{13}$C3-cis-aconitoyl formic acid |
| 1,4,7-$^{13}$C3-cis-aconitoyl formic acid |
| 1,5,6-$^{13}$C3-cis-aconitoyl formic acid |
| 1,5,7-$^{13}$C3-cis-aconitoyl formic acid |

TABLE 14-continued 1,6,7-$^{13}$C3-cis-aconitoyl formic acid
2,3,4-$^{13}$C3-cis-aconitoyl formic acid
2,3,5-$^{13}$C3-cis-aconitoyl formic acid
2,3,6-$^{13}$C3-cis-aconitoyl formic acid
2,3,7-$^{13}$C3-cis-aconitoyl formic acid
3,4,5-$^{13}$C3-cis-aconitoyl formic acid
3,4,6-$^{13}$C3-cis-aconitoyl formic acid
3,4,7-$^{13}$C3-cis-aconitoyl formic acid
3,5,6-$^{13}$C3-cis-aconitoyl formic acid
3,5,7-$^{13}$C3-cis-aconitoyl formic acid
3,6,7-$^{13}$C3-cis-aconitoyl formic acid
4,5,6-$^{13}$C3-cis-aconitoyl formic acid
4,5,7-$^{13}$C3-cis-aconitoyl formic acid
4,6,7-$^{13}$C3-cis-aconitoyl formic acid
5,6,7-$^{13}$C3-cis-aconitoyl formic acid heptalabeled 1,2,3,4,5,6,7-$^{13}$C7-cis-aconitoyl formic acid tetralabeled 1,2,3,4-$^{13}$C4-cis-aconitoyl formic acid
1,2,3,5-$^{13}$C4-cis-aconitoyl formic acid
1,2,3,6-$^{13}$C4-cis-aconitoyl formic acid
1,2,3,7-$^{13}$C4-cis-aconitoyl formic acid
1,2,4,5-$^{13}$C4-cis-aconitoyl formic acid
1,2,4,6-$^{13}$C4-cis-aconitoyl formic acid
1,2,4,7-$^{13}$C4-cis-aconitoyl formic acid
1,2,5,6-$^{13}$C4-cis-aconitoyl formic acid
1,2,5,7-$^{13}$C4-cis-aconitoyl formic acid
1,2,6,7-$^{13}$C4-cis-aconitoyl formic acid
1,3,4,5-$^{13}$C4-cis-aconitoyl formic acid
1,3,4,6-$^{13}$C4-cis-aconitoyl formic acid
1,3,6,7-$^{13}$C4-cis-aconitoyl formic acid
1,4,5,6-$^{13}$C4-cis-aconitoyl formic acid
1,4,5,7-$^{13}$C4-cis-aconitoyl formic acid
1,4,6,7-$^{13}$C4-cis-aconitoyl formic acid
1,5,6,7-$^{13}$C4-cis-aconitoyl formic acid pentalabeled 1,2,3,4,5-$^{13}$C5-cis-aconitoyl formic acid
1,2,3,4,6-$^{13}$C5-cis-aconitoyl formic acid
1,2,3,4,7-$^{13}$C5-cis-aconitoyl formic acid
1,2,3,5,6-$^{13}$C5-cis-aconitoyl formic acid

TABLE 14-continued 1,2,3,5,7-$^{13}$C5-cis-aconitoyl formic acid
1,2,3,6,7-$^{13}$C5-cis-aconitoyl formic acid
1,3,4,5,6-$^{13}$C5-cis-aconitoyl formic acid
1,3,4,5,7-$^{13}$C5-cis-aconitoyl formic acid
1,3,4,6,7-$^{13}$C5-cis-aconitoyl formic acid
1,4,5,6,7-$^{13}$C5-cis-aconitoyl formic acid hexalabeled 1,2,3,4,5,6-$^{13}$C6-cis-aconitoyl formic acid
1,2,3,4,5,7-$^{13}$C6-cis-aconitoyl formic acid
1,3,4,5,6,7-$^{13}$C6-cis-aconitoyl formic acid Cis-Aconitic Acid Isotopologues In certain embodiments, at least one compound prepared by the methods described herein comprises the following, described in Formula 1a-15 and accompanying text below:

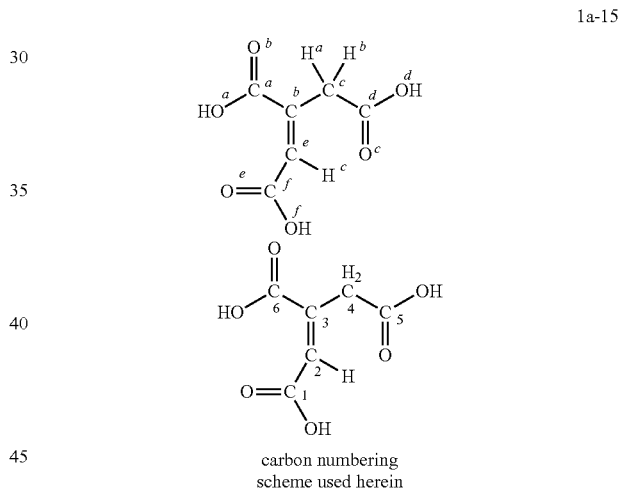

1a-15 carbon numbering scheme used herein or a salt or derivative thereof, wherein atoms of a synthesized compound described by the formula above may be selected as follows, either independently or in combination with any other atoms:

each of atoms $C^a$, $C^b$, $C^c$, $C^d$, $C^e$, and $C^f$ may be independently selected as $^{12}$C, $^{13}$C or $^{14}$C, or a combination thereof;

each of atoms $H^a$, $H^b$, and $H^c$ may be independently selected as $^1$H, $^2$H or $^3$H, or a combination thereof;

each of atoms $O^a$, $O^b$, $O^c$, $O^d$, $O^e$, and $O^f$ may be independently selected as $^{16}$O or $^{18}$O, or a combination thereof.

It is understood that the following compounds have been previously reported or exist in isolatable quantities in nature: cis-aconitic acid with natural isotopic ratios, 1,5-$^{14}$C2-cis-aconitic acid.

In one embodiment, the $^{13}$C isotopic labels of compounds prepared by the methods described herein have the patterns below. Except for any isomers noted as excluded above, each compound listing includes all enantiomers and diastereomers independently and in combination. In one embodiment, provided is a compound as named in Table 15, or a salt, stereoisomer or mixture of stereoisomers thereof. In some embodiments, the compound of Table 15, or a salt, stereoisomer or mixture of stereoisomers thereof, is provided by a method disclosed herein.

TABLE 15 monolabeled

1-$^{13}$C1-cis-aconitic acid
2-$^{13}$C1-cis-aconitic acid
3-$^{13}$C1-cis-aconitic acid
4-$^{13}$C1-cis-aconitic acid
5-$^{13}$C1-cis-aconitic acid
6-$^{13}$C1-cis-aconitic acid dilabeled 1,2-$^{13}$C2-cis-aconitic acid
1,3-$^{13}$C2-cis-aconitic acid
1,4-$^{13}$C2-cis-aconitic acid
1,5-$^{13}$C2-cis-aconitic acid
1,6-$^{13}$C2-cis-aconitic acid
2,3-$^{13}$C2-cis-aconitic acid
2,4-$^{13}$C2-cis-aconitic acid
2,5-$^{13}$C2-cis-aconitic acid
2,6-$^{13}$C2-cis-aconitic acid
3,4-$^{13}$C2-cis-aconitic acid
3,5-$^{13}$C2-cis-aconitic acid
3,6-$^{13}$C2-cis-aconitic acid
4,5-$^{13}$C2-cis-aconitic acid
4,6-$^{13}$C2-cis-aconitic acid
5,6-$^{13}$C2-cis-aconitic acid trilabeled 1,2,3-$^{13}$C3-cis-aconitic acid
1,2,4-$^{13}$C3-cis-aconitic acid
1,2,5-$^{13}$C3-cis-aconitic acid
1,2,6-$^{13}$C3-cis-aconitic acid
1,3,4-$^{13}$C3-cis-aconitic acid
1,3,5-$^{13}$C3-cis-aconitic acid
1,3,6-$^{13}$C3-cis-aconitic acid
1,4,5-$^{13}$C3-cis-aconitic acid
1,4,6-$^{13}$C3-cis-aconitic acid
1,5,6-$^{13}$C3-cis-aconitic acid
2,3,4-$^{13}$C3-cis-aconitic acid
2,3,5-$^{13}$C3-cis-aconitic acid
2,3,6-$^{13}$C3-cis-aconitic acid
3,4,5-$^{13}$C3-cis-aconitic acid
3,4,6-$^{13}$C3-cis-aconitic acid
3,5,6-$^{13}$C3-cis-aconitic acid
4,5,6-$^{13}$C3-cis-aconitic acid tetralabeled 1,2,3,4-$^{13}$C4-cis-aconitic acid
1,2,3,5-$^{13}$C4-cis-aconitic acid
1,2,3,6-$^{13}$C4-cis-aconitic acid
1,2,4,5-$^{13}$C4-cis-aconitic acid
1,2,4,6-$^{13}$C4-cis-aconitic acid
1,2,5,6-$^{13}$C4-cis-aconitic acid
1,3,4,5-$^{13}$C4-cis-aconitic acid
1,3,4,6-$^{13}$C4-cis-aconitic acid
1,4,5,6-$^{13}$C4-cis-aconitic acid pentalabeled 1,2,3,4,5-$^{13}$C5-cis-aconitic acid
1,2,3,4,6-$^{13}$C5-cis-aconitic acid
1,2,3,5,6-$^{13}$C5-cis-aconitic acid
1,3,4,5,6-$^{13}$C5-cis-aconitic acid hexalabeled 1,2,3,4,5,6-$^{13}$C6-cis-aconitic acid Trans-Aconitic Acid Isotopologues In certain embodiments, at least one compound prepared by the methods described herein comprises the following, described in Formula 1a-16 and accompanying text below:

1a-16

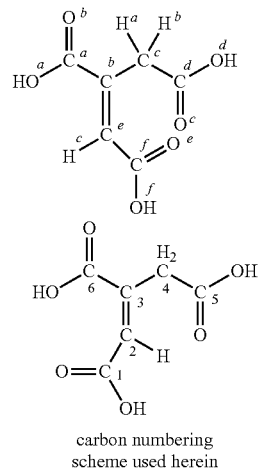

carbon numbering
scheme used herein or a salt or derivative thereof, wherein atoms of a synthesized compound described by the formula above may be selected as follows, either independently or in combination with any other atoms:

each of atoms $0C^a$, $C^b$, $C^c$, $C^d$, $C^e$, and $C^f$ may be independently selected as $^{12}C$, $^{13}C$ or $^{14}C$, or a combination thereof;

each of atoms $H^a$, $H^b$, and $H^c$ may be independently selected as $^1H$, $^2H$ or $^3H$, or a combination thereof;

each of atoms $O^a$, $O^b$, $O^c$, $O^d$, $O^e$, and $O^f$ may be independently selected as $^{16}O$ or $^{18}O$, or a combination thereof.

It is understood that the following compounds have been previously reported or exist in isolatable quantities in nature: trans-aconitic acid with natural isotopic ratios, 1-$^{14}$C1-trans-aconitic acid, 1,5-$^{14}$C2-trans-aconitic acid.

In one embodiment, the $^{13}$C isotopic labels of compounds prepared by the methods described herein have the patterns below. Except for any isomers noted as excluded above, each compound listing includes all enantiomers and diastereomers independently and in combination. In one embodiment, provided is a compound as named in Table 16, or a salt, stereoisomer or mixture of stereoisomers thereof. In some embodiments, the compound of Table 16, or a salt, stereoisomer or mixture of stereoisomers thereof, is provided by a method disclosed herein.

TABLE 16 monolabeled

1-$^{13}$C1-trans-aconitic acid
2-$^{13}$C1-trans-aconitic acid
3-$^{13}$C1-trans-aconitic acid
4-$^{13}$C1-trans-aconitic acid
5-$^{13}$C1-trans-aconitic acid
6-$^{13}$C1-trans-aconitic acid dilabeled 1,2-$^{13}$C2-trans-aconitic acid
1,3-$^{13}$C2-trans-aconitic acid

TABLE 16-continued 1,4-¹³C2-trans-aconitic acid
1,5-¹³C2-trans-aconitic acid
1,6-¹³C2-trans-aconitic acid
2,3-¹³C2-trans-aconitic acid
2,4-¹³C2-trans-aconitic acid
2,5-¹³C2-trans-aconitic acid
2,6-¹³C2-trans-aconitic acid
3,4-¹³C2-trans-aconitic acid
3,5-¹³C2-trans-aconitic acid
3,6-¹³C2-trans-aconitic acid
4,5-¹³C2-trans-aconitic acid
4,6-¹³C2-trans-aconitic acid
5,6-¹³C2-trans-aconitic acid trilabeled 1,2,3-¹³C3-trans-aconitic acid
1,2,4-¹³C3-trans-aconitic acid
1,2,5-¹³C3-trans-aconitic acid
1,2,6-¹³C3-trans-aconitic acid
1,3,4-¹³C3-trans-aconitic acid
1,3,5-¹³C3-trans-aconitic acid
1,3,6-¹³C3-trans-aconitic acid
1,4,5-¹³C3-trans-aconitic acid
1,4,6-¹³C3-trans-aconitic acid
1,5,6-¹³C3-trans-aconitic acid
2,3,4-¹³C3-trans-aconitic acid
2,3,5-¹³C3-trans-aconitic acid
2,3,6-¹³C3-trans-aconitic acid
3,4,5-¹³C3-trans-aconitic acid
3,4,6-¹³C3-trans-aconitic acid
3,5,6-¹³C3-trans-aconitic acid
4,5,6-¹³C3-trans-aconitic acid tetralabeled 1,2,3,4-¹³C4-trans-aconitic acid
1,2,3,5-¹³C4-trans-aconitic acid
1,2,3,6-¹³C4-trans-aconitic acid
1,2,4,5-¹³C4-trans-aconitic acid
1,2,4,6-¹³C4-trans-aconitic acid
1,2,5,6-¹³C4-trans-aconitic acid
1,3,4,5-¹³C4-trans-aconitic acid
1,3,4,6-¹³C4-trans-aconitic acid
1,4,5,6-¹³C4-trans-aconitic acid pentalabeled 1,2,3,4,5-¹³C5-trans-aconitic acid
1,2,3,4,6-¹³C5-trans-aconitic acid
1,2,3,5,6-¹³C5-trans-aconitic acid
1,3,4,5,6-¹³C5-trans-aconitic acid hexalabeled 1,2,3,4,5,6-¹³C6-trans-aconitic acid

(E)-3-(carboxylatomethyl)-2-hydroxypent-3-Enedioic Acid Isotopologues (Table 17)

In certain embodiments, at least one compound prepared by the methods described herein comprises the following, described in Formula 1a-17 and/or 1b-17 and accompanying text below:

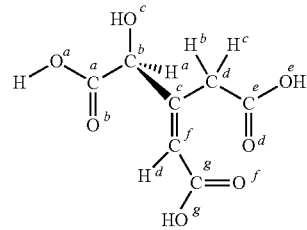

1b-17

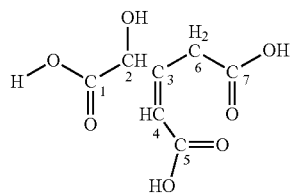

carbon numbering
scheme used herein or a salt or derivative thereof, wherein atoms of a synthesized compound described by the formula above may be selected as follows, either independently or in combination with any other atoms:

each of atoms $C^a$, $C^b$, $C^c$, $C^d$, $C^e$, $C^f$, and $C^g$ may be independently selected from $^{12}C$, $^{13}C$ or $^{14}C$, or a combination thereof;

each of atoms $H^a$, $H^b$, $H^c$ and $H^d$ may be independently selected from $^{1}H$, $^{2}H$ or $^{3}H$, or a combination thereof;

each of atoms $O^a$, $O^b$, $O^c$, $O^d$, $O^e$, $O^f$, and $O^g$ may be independently selected from $^{16}O$ or $^{18}O$, or a combination thereof.

In one embodiment, provided is a compound of Formula 1a-17 or 1b-17 or a salt, stereoisomer or mixture of stereoisomers thereof. In some embodiments, the compound of Formula 1a-17 or 1b-17, or a salt, stereoisomer or mixture of stereoisomers thereof, is provided by a method disclosed herein.

(Z)-3-(carboxylatomethyl)-2-hydroxypent-3-Enedioic Acid Isotopologues

In certain embodiments, at least one compound prepared by the methods described herein comprises the following, described in Formula 1a-18 and/or 1b-18 and accompanying text below:

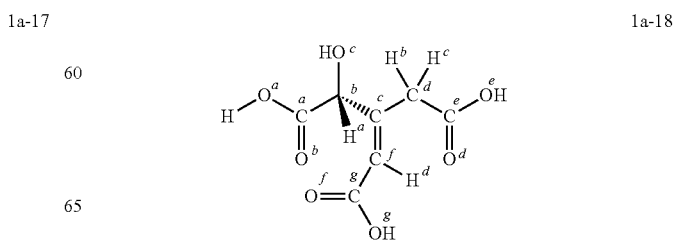

-continued

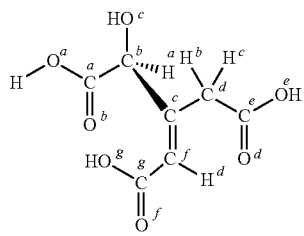

1b-18

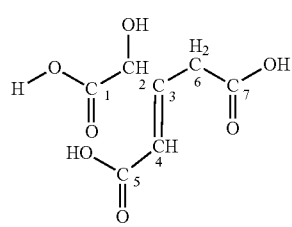

carbon numbering
scheme used herein or a salt or derivative thereof, wherein atoms of a synthesized compound described by the formula above may be selected as follows, either independently or in combination with any other atoms:

each of atoms $C^a$, $C^b$, $C^c$, $C^d$, $C^e$, $C^f$, and $C^g$ may be independently selected as $^{12}C$, $^{13}C$ or $^{14}C$, or a combination thereof;

each of atoms $H^a$, $H^b$, $H^c$ and $H^d$ may be independently selected as $^1H$, $^2H$ or $^3H$, or a combination thereof;

each of atoms $O^a$, $O^b$, $O^c$, $O^d$, $O^e$, $O^f$, and $O^g$ may be independently selected as $^{16}O$ or $^{18}O$, or a combination thereof.

In one embodiment, provided is a compound of Formula 1a-18 or 1b-18 or a salt, stereoisomer or mixture of stereoisomers thereof. In some embodiments, the compound of Formula 1a-18 or 1b-18, or a salt, stereoisomer or mixture of stereoisomers thereof, is provided by a method disclosed herein.

3-(carboxylatomethyl)-2,4-Dihydroxypentanedioic Acid Isotopologues

In certain embodiments, at least one compound prepared by the methods described herein comprises the following, described in Formula 1a-19 and accompanying text below:

1a-19

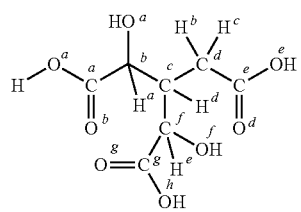

-continued

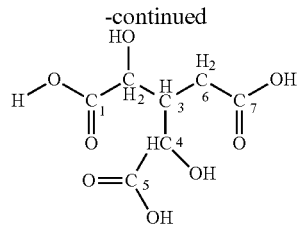

carbon numbering
scheme used herein or a salt or derivative thereof, including all stereoisomers independently and in combination, wherein atoms of a synthesized compound described by the formula above may be selected as follows, either independently or in combination with any other atoms:

each of atoms $C^a$, $C^b$, $C^c$, $C^d$, $C^e$, $C^f$, and $C^g$ may be independently selected as $^{12}C$, $^{13}C$ or $^{14}C$, or a combination thereof;

each of atoms $H^a$, $H^b$, $H^c$, $H^d$ and $H^e$ may be independently selected as $^1H$, $^2H$ or $^3H$, or a combination thereof;

each of atoms $O^a$, $O^b$, $O^c$, $O^d$, $O^e$, $O^f$, $O^g$ and $O^h$ may be independently selected as $^{16}O$ or $^{18}O$, or a combination thereof.

In one embodiment, provided is a compound of Formula 1a-19, or a salt, stereoisomer or mixture of stereoisomers thereof. In some embodiments, the compound of Formula 1a-19, or a salt, stereoisomer or mixture of stereoisomers thereof, is provided by a method disclosed herein.

3-(carboxylatomethyl)-2-hydroxy-4-Aminopentanedioic Acid Isotopologues

In certain embodiments, at least one compound prepared by the methods described herein comprises the following, described in Formula 1a-20 and accompanying text below:

1a-20

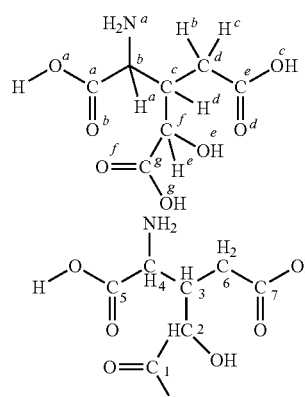

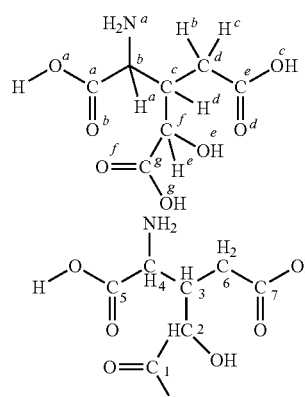

carbon numbering
scheme used herein or a salt or derivative thereof, including all stereoisomers independently and in combination, wherein atoms of a synthesized compound described by the formula above may be selected as follows, either independently or in combination with any other atoms:

each of atoms $C^a$, $C^b$, $C^c$, $C^d$, $C^e$, $C^f$, and $C^g$ may be independently selected as $^{12}C$, $^{13}C$ or $^{14}C$, or a combination thereof;

each of atoms $H^a$, $H^b$, $H^c$, $H^d$ and $H^e$ may be independently selected as $^1H$, $^2H$ or $^3H$, or a combination thereof;

each of atoms $O^a$, $O^b$, $O^c$, $O^d$, $O^e$, $O^f$, and $O^g$ may be independently selected as $^{16}O$ or $^{18}O$, or a combination thereof.

$N^a$ is independently $^{14}N$ or $^{15}N$.

In one embodiment, provided is a compound of Formula 1a-20, or a salt, stereoisomer or mixture of stereoisomers thereof. In some embodiments, the compound of Formula 1a-20, or a salt, stereoisomer or mixture of stereoisomers thereof, is provided by a method disclosed herein.

(E)-3-(carboxylatomethyl)-4-aminopent-3-Enedioic Acid Isotopologues

In certain embodiments, at least one compound prepared by the methods described herein comprises the following, described in Formula 1a-21 and accompanying text below:

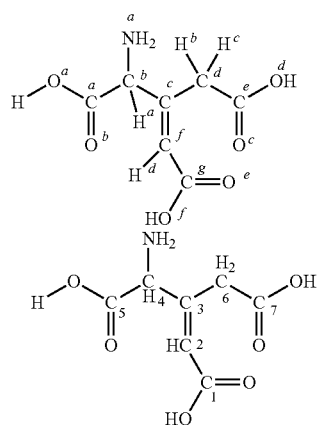

1a-21 carbon numbering scheme used herein or a salt or derivative thereof, including all stereoisomers independently and in combination, wherein atoms of a synthesized compound described by the formula above may be selected as follows, either independently or in combination with any other atoms:

each of atoms $C^a$, $C^b$, $C^c$, $C^d$, $C^e$, $C^f$, and $C^g$ may be independently selected as $^{12}C$, $^{13}C$ or $^{14}C$, or a combination thereof;

each of atoms $H^a$, $H^b$, $H^c$, and $H^d$ may be independently selected as $^1H$, $^2H$ or $^3H$, or a combination thereof;

each of atoms $O^a$, $O^b$, $O^c$, $O^d$, $O^e$, and $O^f$ may be independently selected as $^{16}O$ or $^{18}O$, or a combination thereof.

$N^a$ is independently $^{14}N$ or $^{15}N$

In one embodiment, provided is a compound of Formula 1a-21, or a salt, stereoisomer or mixture of stereoisomers thereof. In some embodiments, the compound of Formula 1a-21, or a salt, stereoisomer or mixture of stereoisomers thereof, is provided by a method disclosed herein.

(Z)-3-(carboxylatomethyl)-4-aminopent-3-Enedioic Acid Isotopologues

In certain embodiments, at least one compound prepared by the methods described herein comprises the following, described in Formula 1a-22 and accompanying text below:

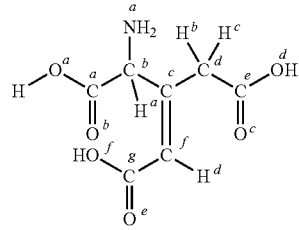

1a-22

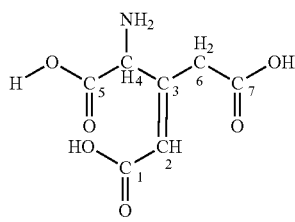

carbon numbering scheme used herein or a salt or derivative thereof, including all stereoisomers independently and in combination, wherein atoms of a synthesized compound described by the formula above may be selected as follows, either independently or in combination with any other atoms:

each of atoms $C^a$, $C^b$, $C^c$, $C^d$, $C^e$, $C^f$, and $C^g$ may be independently selected as $^{12}C$, $^{13}C$ or $^{14}C$, or a combination thereof;

each of atoms $H^a$, $H^b$, $H^c$, and $H^d$ may be independently selected as $^1H$, $^2H$ or $^3H$, or a combination thereof;

each of atoms $O^a$, $O^b$, $O^c$, $O^d$, $O^e$, and $O^f$ may be independently selected as $^{16}O$ or $^{18}O$, or a combination thereof.

$N^a$ is independently $^{14}N$ or $^{15}N$

In one embodiment, provided is a compound of Formula 1a-22, or a salt, stereoisomer or mixture of stereoisomers thereof. In some embodiments, the compound of Formula 1a-22, or a salt, stereoisomer or mixture of stereoisomers thereof, is provided by a method disclosed herein.

Tricarballylate Formic Acid Isotopologues

In certain embodiments, at least one compound prepared by the methods described herein comprises the following, described in Formula 1a-23 and accompanying text below:

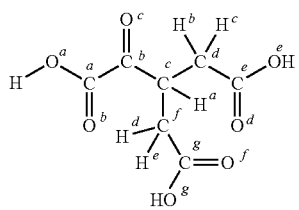

1a-23

-continued

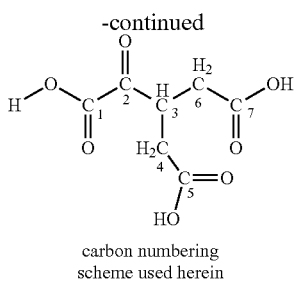

carbon numbering
scheme used herein or a salt or derivative thereof, including all stereoisomers independently and in combination, wherein atoms of a synthesized compound described by the formula above may be selected as follows, either independently or in combination with any other atoms:

each of atoms $C^a$, $C^b$, $C^c$, $C^d$, $C^e$, $C^f$, and $C^g$ may be independently selected as $^{12}C$, $^{13}C$ or $^{14}C$, or a combination thereof;

each of atoms $H^a$, $H^b$, $H^c$, $H^d$ and $H^e$ may be independently selected as $^1H$, $^2H$ or $^3H$, or a combination thereof;

each of atoms $O^a$, $O^b$, $O^c$, $O^d$, $O^e$, $O^f$, and $O^g$ may be independently selected as $^{16}O$ or $^{18}O$, or a combination thereof.

In one embodiment, provided is a compound of Formula 1a-23, or a salt, stereoisomer or mixture of stereoisomers thereof. In some embodiments, the compound of Formula 1a-23, or a salt, stereoisomer or mixture of stereoisomers thereof, is provided by a method disclosed herein.

3-(carboxylatomethyl)-2-Hydroxypentanedioic Acid Isotopologues

In certain embodiments, at least one compound prepared by the methods described herein comprises the following, described in Formula 1a-24 and accompanying text below:

1a-24

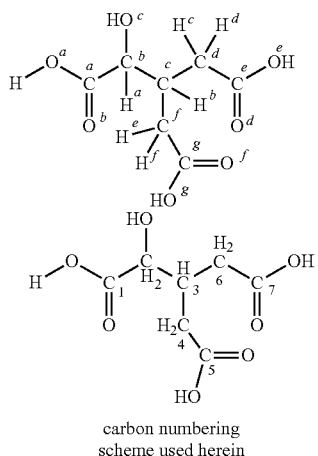

carbon numbering
scheme used herein or a salt or derivative thereof, including all stereoisomers independently and m combination, wherein atoms of a synthesized compound described by the formula above may be selected as follows, either independently or in combination with any other atoms:

each of atoms $C^a$, $C^b$, $C^c$, $C^d$, $C^e$, $C^f$, and $C^g$ may be independently selected as $^{12}C$, $^{13}C$ or $^{14}C$, or a combination thereof;

each of atoms $H^a$, $H^b$, $H^c$, $H^d$, $H^e$ and $H^f$ may be independently selected as $^1H$, $^2H$ or $^3H$, or a combination thereof;

each of atoms $O^a$, $O^b$, $O^c$, $O^d$, $O^e$, $O^f$, and $O^g$ may be independently selected as $^{16}O$ or $^{18}O$, or a combination thereof.

In one embodiment, provided is a compound of Formula 1a-24, or a salt, stereoisomer or mixture of stereoisomers thereof. In some embodiments, the compound of Formula 1a-24, or a salt, stereoisomer or mixture of stereoisomers thereof, is provided by a method disclosed herein.

3-(carboxylatomethyl)-2-Aminopentanedioic Acid Isotopologues Also Known as 3-(carboxymethyl)-Glutamic Acid In certain embodiments, at least one compound prepared by the methods described herein comprises the following, described in Formula 1a-25 and accompanying text below:

1a-25

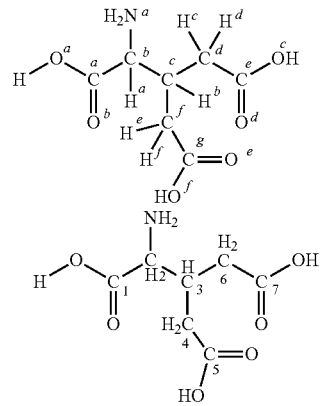

carbon numbering
scheme used herein or a salt or derivative thereof, including all stereoisomers independently and in combination, wherein atoms of a synthesized compound described by the formula above may be selected as follows, either independently or in combination with any other atoms:

each of atoms $C^a$, $C^b$, $C^c$, $C^d$, $C^e$, $C^f$, and $C^g$ may be independently selected as $^{12}C$, $^{13}C$ or $^{14}C$, or a combination thereof;

each of atoms $H^a$, $H^b$, $H^c$, $H^d$, $H^e$ and $H^f$ may be independently selected as $^1H$, $^2H$ or $^3H$, or a combination thereof;

each of atoms $O^a$, $O^b$, $O^c$, $O^d$, $O^e$, and $O^f$ may be independently selected as $^{16}O$ or $^{18}O$, or a combination thereof.

$N^a$ is independently $^{14}N$ or $^{15}N$

It is understood that the following compound has been previously reported or exists in isolatable quantities in nature: 3-(carboxymethyl)-glutamic acid of natural isotopic ratios.

In one embodiment, provided is a compound of Formula 1a-25, or a salt, stereoisomer or mixture of stereoisomers thereof. In some embodiments, the compound of Formula 1a-25, or a salt, stereoisomer or mixture of stereoisomers thereof, is provided by a method disclosed herein.

4-(carboxylatomethyl)-Zymonic Acid Isotopologues Also Known as 2-carboxy-2,5-dihydro-4-hydroxy-5-oxo-2-Furanacetic Acid In certain embodiments, at least one compound prepared by the methods described herein comprises the following, described in Formula 1a-26 and accompanying text below:

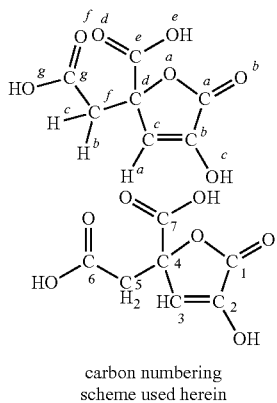

1a-26 carbon numbering scheme used herein or a salt or derivative thereof, including all stereoisomers independently and in combination, wherein atoms of a synthesized compound described by the formula above may be selected as follows, either independently or in combination with any other atoms:

each of atoms $C^a$, $C^b$, $C^c$, $C^d$, $C^e$, $C^f$, and $C^g$ may be independently selected as $^{12}C$, $^{13}C$ or $^{14}C$, or a combination thereof;

each of atoms $H^a$, $H^b$, and $H^c$ may be independently selected as $^1H$, $^2H$ or $^3H$, or a combination thereof;

each of atoms $O^a$, $O^b$, $O^c$, $O^d$, $O^e$, $O^f$, and $O^g$ may be independently selected as $^{16}O$ or $^{18}O$, or a combination thereof.

It is understood that the following compound has been previously reported or exists in isolatable quantities in nature: 4-(carboxylatomethyl)-zymonic acid of natural isotopic ratios.

In one embodiment, provided is a compound of Formula 1a-26, or a salt, stereoisomer or mixture of stereoisomers thereof. In some embodiments, the compound of Formula 1a-26, or a salt, stereoisomer or mixture of stereoisomers thereof, is provided by a method disclosed herein.

4-(carboxylatomethyl)-2-Enol-γ-Butyrlactone Isotopologues

In certain embodiments, at least one compound prepared by the methods described herein comprises the following, described in Formula 1a-27 and accompanying text below:

1a-27

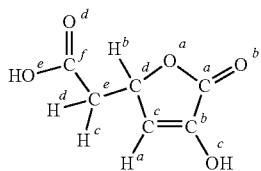

-continued

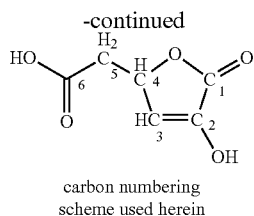

carbon numbering scheme used herein or a salt or derivative thereof, including all stereoisomers independently and in combination, wherein atoms of a synthesized compound described by the formula above may be selected as follows, either independently or in combination with any other atoms:

each of atoms $C^a$, $C^b$, $C^c$, $C^d$, $C^e$, and $C^f$ may be independently selected as $^{12}C$, $^{13}C$ or $^{14}C$, or a combination thereof;

each of atoms $H^a$, $H^b$, $H^c$, and $H^d$ may be independently selected as $^1H$, $^2H$ or $^3H$, or a combination thereof;

each of atoms $O^a$, $O^b$, $O^c$, $O^d$, and $O^e$ may be independently selected as $^{16}O$ or $^{18}O$, or a combination thereof.

In one embodiment, provided is a compound of Formula 1a-27, or a salt, stereoisomer or mixture of stereoisomers thereof. In some embodiments, the compound of Formula 1a-27, or a salt, stereoisomer or mixture of stereoisomers thereof, is provided by a method disclosed herein.

Compositions

Provided herein is a composition comprising an organic acid that is prepared by any method or process described herein. In some of such embodiments, the organic acid is $^2H$ or $^{13}C$ isotopically enriched. Provided herein are compositions comprising isotopically enriched metabolites and metabolic derivatives described herein. Also provided is:

An α-ketoglutaric acid isotopologues composition of matter comprising one or more compounds set forth in Table 1.

A 2-hydroxyglutaric acid isotopologues composition of matter one or more compounds set forth in Table 2.

An oxopentanedioic acid isotopologues composition of matter one or more compounds set forth in Table 3.

A DL-4-hydroxyketoglutaric acid isotopologues composition of matter one or more compounds set forth in Table 4.

A 2,4-dihydroxyglutaric acid isotopologues composition of matter one or more compounds set forth in Table 5.

A gamma-hydroxyglutamic acid isotopologues composition of matter one or more compounds set forth in Table 6.

A fumaric acid isotopologues composition of matter one or more compounds set forth in Table 7.

A succinic acid isotopologues composition of matter one or more compounds set forth in Table 8.

A malic acid isotopologues composition of matter one or more compounds set forth in Table 9.

An isocitroylformic acid isotopologues composition of matter one or more compounds set forth in Table 10.

A isocitric acid isotopologues composition of matter one or more compounds set forth in Table 11.

A tricarballylic acid isotopologues composition of matter one or more compounds set forth in Table 12.

A trans-aconitoyl formic acid isotopologues composition of matter one or more compounds set forth in Table 13.

A cis-aconitoyl formic acid isotopologues composition of matter as set forth in Table 14.

A cis-aconitic acid isotopologues composition of matter one or more compounds set forth in Table 15.

A trans-aconitic acid isotopologues composition of matter one or more compounds set forth in Table 16.

An (E)-3-(carboxylatomethyl)-2-hydroxypent-3-enedioic acid isotopologues composition of matter comprising one or more compounds of formula 1a-17 or 1b-17.

A (E)-3-(carboxylatomethyl)-2-hydroxypent-3-enedioic acid isotopologues composition of matter comprising one or more compounds of formula 1a-18 or 1b-18.

A 3-(carboxylatomethyl)-2,4-dihydroxypentanedioic acid isotopologues composition of matter comprising one or more compounds of formula 1a-19.

A 3-(carboxylatomethyl)-2-hydroxy-4-aminopentanedioic acid isotopologues composition of matter comprising one or more compounds of formula 1a-20.

An (E)-3-(carboxylatomethyl)-4-aminopent-3-enedioic acid isotopologues composition of matter comprising one or more compounds of formula 1a-21.

A (Z)-3-(carboxylatomethyl)-4-aminopent-3-enedioic acid isotopologues composition of matter comprising one or more compounds of formula 1a-22.

A tricarballylate formic acid isotopologues composition of matter comprising one or more compounds of formula 1a-23.

A 3-(carboxylatomethyl)-2-hydroxypentanedioic acid isotopologues composition of matter comprising one or more compounds of formula 1a-24.

A 3-(carboxylatomethyl)-2-aminopentanedioic acid isotopologues composition of matter comprising one or more compounds of formula 1a-25.

A 4-(carboxylatomethyl)-zymonic acid isotopologues composition of matter comprising one or more compounds of formula 1a-26.

A 4-(carboxylatomethyl)-2-Enol-?-butyrolactone isotopologues composition of matter comprising one or more compounds of formula 1a-27.

In an embodiment, provided herein is a compound selected from the group consisting of:

TABLE B

| | | |
|---|---|---|
| 1,3-$^{13}$C2-α-ketoglutaric acid | 1,2,3-$^{13}$C3-α-ketoglutaric acid | 1,2,3,5-$^{13}$C4-α-ketoglutaric acid |
| 1,4-$^{13}$C2-α-ketoglutaric acid | 1,2,4-$^{13}$C3-α-ketoglutaric acid | 1,3,4,5-$^{13}$C4-α-ketoglutaric acid |
| 1,5-$^{13}$C2-α-ketoglutaric acid | 1,2,5-$^{13}$C3-α-ketoglutaric acid | 2,3,4,5-$^{13}$C4-α-ketoglutaric acid |
| 2,4-$^{13}$C2-α-ketoglutaric acid | 1,3,5-$^{13}$C3-α-ketoglutaric acid | |
| 2,5-$^{13}$C2-α-ketoglutaric acid | 1,4,5-$^{13}$C3-α-ketoglutaric acid | |
| 3,5-$^{13}$C2-α-ketoglutaric acid | 2,4,5-$^{13}$C3-α-ketoglutaric acid | |
| 1-$^{13}$C1-2-hydroxyglutaric acid | 1,2-$^{13}$C2-2-hydroxyglutaric acid | 1,2,4-$^{13}$C3-2-hydroxyglutaric acid |
| 2-$^{13}$C1-2-hydroxyglutaric acid | 1,3-$^{13}$C2-2-hydroxyglutaric acid | 1,2,5-$^{13}$C3-2-hydroxyglutaric acid |
| 3-$^{13}$C1-2-hydroxyglutaric acid | 1,4-$^{13}$C2-2-hydroxyglutaric acid | 1,3,4-$^{13}$C3-2-hydroxyglutaric acid |
| 4-$^{13}$C1-2-hydroxyglutaric acid | 1,5-$^{13}$C2-2-hydroxyglutaric acid | 1,3,5-$^{13}$C3-2-hydroxyglutaric acid |
| 5-$^{13}$C1-2-hydroxyglutaric acid | 2,3-$^{13}$C2-2-hydroxyglutaric acid | 1,4,5-$^{13}$C3-2-hydroxyglutaric acid |
| | 2,4-$^{13}$C2-2-hydroxyglutaric acid | 2,3,4-$^{13}$C3-2-hydroxyglutaric acid |
| 1,2,3,5-$^{13}$C4-2-hydroxyglutaric acid | 2,5-$^{13}$C2-2-hydroxyglutaric acid | 2,4,5-$^{13}$C3-2-hydroxyglutaric acid |
| 1,3,4,5-$^{13}$C4-2-hydroxyglutaric acid | 3,4-$^{13}$C2-2-hydroxyglutaric acid | 3,4,5-$^{13}$C3-2-hydroxyglutaric acid |
| 2,3,4,5-$^{13}$C4-2-hydroxyglutaric acid | 3,5-$^{13}$C2-2-hydroxyglutaric acid | |
| | 4,5-$^{13}$C2-2-hydroxyglutaric acid | |
| 1-$^{13}$C1-4-hydroxyketoglutaric acid | 1,2-$^{13}$C2-4-hydroxyketoglutaric acid | 1,2,3-$^{13}$C3-4-hydroxyketoglutaric acid |
| 2-$^{13}$C1-4-hydroxyketoglutaric acid | 1,3-$^{13}$C2-4-hydroxyketoglutaric acid | 1,2,4-$^{13}$C3-4-hydroxyketoglutaric acid |
| 3-$^{13}$C1-4-hydroxyketoglutaric acid | 1,4-$^{13}$C2-4-hydroxyketoglutaric acid | 1,2,5-$^{13}$C3-4-hydroxyketoglutaric acid |
| 4-$^{13}$C1-4-hydroxyketoglutaric acid | 1,5-$^{13}$C2-4-hydroxyketoglutaric acid | 1,3,4-$^{13}$C3-4-hydroxyketoglutaric acid |
| 5-$^{13}$C1-4-hydroxyketoglutaric acid | 2,3-$^{13}$C2-4-hydroxyketoglutaric acid | 1,3,5-$^{13}$C3-4-hydroxyketoglutaric acid |
| | 2,4-$^{13}$C2-4-hydroxyketoglutaric acid | 1,4,5-$^{13}$C3-4-hydroxyketoglutaric acid |
| 1,2,3,4-$^{13}$C4-4-hydroxyketoglutaric acid | 2,5-$^{13}$C2-4-hydroxyketoglutaric acid | 2,3,4-$^{13}$C3-4-hydroxyketoglutaric acid |
| 1,2,3,5-$^{13}$C4-4-hydroxyketoglutaric acid | 3,4-$^{13}$C2-4-hydroxyketoglutaric acid | 2,4,5-$^{13}$C3-4-hydroxyketoglutaric acid |
| 1,3,4,5-$^{13}$C4-4-hydroxyketoglutaric acid | 3,5-$^{13}$C2-4-hydroxyketoglutaric acid | 3,4,5-$^{13}$C3-4-hydroxyketoglutaric acid |
| 2,3,4,5-$^{13}$C4-4-hydroxyketoglutaric acid | 4,5-$^{13}$C2-4-hydroxyketoglutaric acid | |
| 1-$^{13}$C1-2,4-dihydroxyketoglutaric acid | 1,2-$^{13}$C2-2,4-dihydroxyketoglutaric acid | 1,2,3-$^{13}$C3-2,4-dihydroxyketoglutaric acid |
| 2-$^{13}$C1-2,4-dihydroxyketoglutaric acid | 1,3-$^{13}$C2-2,4-dihydroxyketoglutaric acid | 1,2,4-$^{13}$C3-2,4-dihydroxyketoglutaric acid |
| 3-$^{13}$C1-2,4-dihydroxyketoglutaric acid | 1,4-$^{13}$C2-2,4-dihydroxyketoglutaric acid | 1,2,5-$^{13}$C3-2,4-dihydroxyketoglutaric acid |
| 4-$^{13}$C1-2,4-dihydroxyketoglutaric acid | 1,5-$^{13}$C2-2,4-dihydroxyketoglutaric acid | 1,3,4-$^{13}$C3-2,4-dihydroxyketoglutaric acid |
| 5-$^{13}$C1-2,4- | 2,3-$^{13}$C2-2,4- | 1,3,5-$^{13}$C3-2,4- |

TABLE B-continued

| | | |
|---|---|---|
| dihydroxyketoglutaric acid | dihydroxyketoglutaric acid 2,4-$^{13}$C2-2,4-dihydroxyketoglutaric acid | dihydroxyketoglutaric acid 1,4,5-$^{13}$C3-2,4-dihydroxyketoglutaric acid |
| 1,2,3,4-$^{13}$C4-2,4-dihydroxyketoglutaric acid | 2,5-$^{13}$C2-2,4-dihydroxyketoglutaric acid | 2,3,4-$^{13}$C3-2,4-dihydroxyketoglutaric acid |
| 1,2,3,5-$^{13}$C4-2,4-dihydroxyketoglutaric acid | 3,4-$^{13}$C2-2,4-dihydroxyketoglutaric acid | 2,4,5-$^{13}$C3-2,4-dihydroxyketoglutaric acid |
| 1,3,4,5-$^{13}$C4-2,4-dihydroxyketoglutaric acid | 3,5-$^{13}$C2-2,4-dihydroxyketoglutaric acid | 3,4,5-$^{13}$C3-2,4-dihydroxyketoglutaric acid |
| 2,3,4,5-$^{13}$C4-4-hydroxyketoglutaric acid | 4,5-$^{13}$C2-4-hydroxyketoglutaric acid | |
| 1-$^{13}$C1-gamma-hydroxyglutamate | 1,2-$^{13}$C2-gamma-hydroxyglutamate | 1,2,3-$^{13}$C3-gamma-hydroxyglutamate |
| 2-$^{13}$C1-gamma-hydroxyglutamate | 1,3-$^{13}$C2-gamma-hydroxyglutamate | 1,2,4-$^{13}$C3-gamma-hydroxyglutamate |
| 3-$^{13}$C1-gamma-hydroxyglutamate | 1,4-$^{13}$C2-gamma-hydroxyglutamate | 1,2,5-$^{13}$C3-gamma-hydroxyglutamate |
| 4-$^{13}$C1-gamma-hydroxyglutamate | 1,5-$^{13}$C2-gamma-hydroxyglutamate | 1,3,4-$^{13}$C3-gamma-hydroxyglutamate |
| 5-$^{13}$C1-gamma-hydroxyglutamate | 2,3-$^{13}$C2-gamma-hydroxyglutamate | 1,3,5-$^{13}$C3-gamma-hydroxyglutamate |
| | 2,4-$^{13}$C2-gamma-hydroxyglutamate | 1,4,5-$^{13}$C3-gamma-hydroxyglutamate |
| 1,2,3,4-$^{13}$C4-gamma-hydroxyglutamate | 2,5-$^{13}$C2-gamma-hydroxyglutamate | 2,3,4-$^{13}$C3-gamma-hydroxyglutamate |
| 1,2,3,5-$^{13}$C4-gamma-hydroxyglutamate | 3,4-$^{13}$C2-gamma-hydroxyglutamate | 2,4,5-$^{13}$C3-gamma-hydroxyglutamate |
| 1,3,4,5-$^{13}$C4-gamma-hydroxyglutamate | 3,5-$^{13}$C2-gamma-hydroxyglutamate | 3,4,5-$^{13}$C3-gamma-hydroxyglutamate |
| 2,3,4,5-$^{13}$C4-gamma-hydroxyglutamate | 4,5-$^{13}$C2-gamma-hydroxyglutamate | |
| 1,3-$^{13}$C2-succinic acid | 1,2,3-$^{13}$C3-succinic acid | |
| | 1,2,4-$^{13}$C3-succinic acid | |
| 1,2-$^{13}$C2-(R)-malic acid | 1,2,3-$^{13}$C3-malic acid | |
| 1,3-$^{13}$C2-malic acid | 1,2,4-$^{13}$C3-malic acid | |
| 2,3-$^{13}$C2-malic acid | 1,3,4-$^{13}$C3-malic acid | |
| 3,4-$^{13}$C2-malic acid | 2,3,4-$^{13}$C3-malic acid | |
| 1,2,3,4,5,6,7-$^{12}$C7-isocitroylformic acid | 1,2,3-$^{13}$C3-isocitroylformic acid | 1,2,3,4-$^{13}$C4-isocitroylformic acid |
| | 1,2,4-$^{13}$C3-isocitroylformic acid | 1,2,3,5-$^{13}$C4-isocitroylformic acid |
| 1-$^{13}$C1-isocitroylformic acid | 1,2,5-$^{13}$C3-isocitroylformic acid | 1,2,3,6-$^{13}$C4-isocitroylformic acid |
| 2-$^{13}$C1-isocitroylformic acid | 1,2,6-$^{13}$C3-isocitroylformic acid | 1,2,3,7-$^{13}$C4-isocitroylformic acid |
| 3-$^{13}$C1-isocitroylformic acid | 1,2,7-$^{13}$C3-isocitroylformic acid | 1,2,4,5-$^{13}$C4-isocitroylformic acid |
| 4-$^{13}$C1-isocitroylformic acid | 1,3,4-$^{13}$C3-isocitroylformic acid | 1,2,4,6-$^{13}$C4-isocitroylformic acid |
| 5-$^{13}$C1-isocitroylformic acid | 1,3,5-$^{13}$C3-isocitroylformic acid | 1,2,4,7-$^{13}$C4-isocitroylformic acid |
| 6-$^{13}$C1-isocitroylformic acid | 1,3,6-$^{13}$C3-isocitroylformic acid | 1,2,5,6-$^{13}$C4-isocitroylformic acid |
| 7-$^{13}$C1-isocitroylformic acid | 1,3,7-$^{13}$C3-isocitroylformic acid | 1,2,5,7-$^{13}$C4-isocitroylformic acid |
| | 1,4,5-$^{13}$C3-isocitroylformic acid | 1,2,6,7-$^{13}$C4-isocitroylformic acid |
| | 1,4,6-$^{13}$C3-isocitroylformic acid | 1,3,4,5-$^{13}$C4-isocitroylformic acid |
| 1,2-$^{13}$C2-isocitroylformic acid | 1,4,7-$^{13}$C3-isocitroylformic acid | 1,3,4,6-$^{13}$C4-isocitroylformic acid |
| 1,3-$^{13}$C2-isocitroylformic acid | 1,5,6-$^{13}$C3-isocitroylformic acid | 1,3,6,7-$^{13}$C4-isocitroylformic acid |
| 1,4-$^{13}$C2-isocitroylformic acid | 1,5,7-$^{13}$C3-isocitroylformic acid | 1,4,5,6-$^{13}$C4-isocitroylformic acid |
| 1,5-$^{13}$C2-isocitroylformic acid | 1,6,7-$^{13}$C3-isocitroylformic acid | 1,4,5,7-$^{13}$C4-isocitroylformic acid |
| 1,6-$^{13}$C2-isocitroylformic acid | 2,3,4-$^{13}$C3-isocitroylformic acid | 1,4,6,7-$^{13}$C4-isocitroylformic acid |
| 1,7-$^{13}$C2-isocitroylformic acid | 2,3,5-$^{13}$C3-isocitroylformic acid | 1,5,6,7-$^{13}$C4-isocitroylformic acid |
| 2,3-$^{13}$C2-isocitroylformic acid | 2,3,6-$^{13}$C3-isocitroylformic acid | |
| 2,4-$^{13}$C2-isocitroylformic acid | 2,3,7-$^{13}$C3-isocitroylformic acid | |
| 2,5-$^{13}$C2-isocitroylformic acid | 3,4,5-$^{13}$C3-isocitroylformic acid | 1,2,3,4,5-$^{13}$C5-isocitroylformic acid |
| 2,6-$^{13}$C2-isocitroylformic acid | 3,4,6-$^{13}$C3-isocitroylformic acid | 1,2,3,4,6-$^{13}$C5-isocitroylformic acid |

TABLE B-continued

| | | |
|---|---|---|
| 2,7-$^{13}$C2-isocitroylformic acid | 3,4,7-$^{13}$C3-isocitroylformic acid | 1,2,3,4,7-$^{13}$C5-isocitroylformic acid |
| 3,4-$^{13}$C2-isocitroylformic acid | 3,5,6-$^{13}$C3-isocitroylformic acid | 1,2,3,5,6-$^{13}$C5-isocitroylformic acid |
| 3,5-$^{13}$C2-isocitroylformic acid | 3,5,7-$^{13}$C3-isocitroylformic acid | 1,2,3,5,7-$^{13}$C5-isocitroylformic acid |
| 3,6-$^{13}$C2-isocitroylformic acid | 3,6,7-$^{13}$C3-isocitroylformic acid | 1,2,3,6,7-$^{13}$C5-isocitroylformic acid |
| 3,7-$^{13}$C2-isocitroylformic acid | 4,5,6-$^{13}$C3-isocitroylformic acid | 1,3,4,5,6-$^{13}$C5-isocitroylformic acid |
| 4,5-$^{13}$C2-isocitroylformic acid | 4,5,7-$^{13}$C3-isocitroylformic acid | 1,3,4,5,7-$^{13}$C5-isocitroylformic acid |
| 4,6-$^{13}$C2-isocitroylformic acid | 4,6,7-$^{13}$C3-isocitroylformic acid | 1,3,4,6,7-$^{13}$C5-isocitroylformic acid |
| 4,7-$^{13}$C2-isocitroylformic acid | 5,6,7-$^{13}$C3-isocitroylformic acid | 1,4,5,6,7-$^{13}$C5-isocitroylformic acid |
| 5,6-$^{13}$C2-isocitroylformic acid | | |
| 5,7-$^{13}$C2-isocitroylformic acid | | |
| 6,7-$^{13}$C2-isocitroylformic acid | 1,2,3,4,5,6,7-$^{13}$C7-isocitroylformic acid | 1,2,3,4,5,6-$^{13}$C6-isocitroylformic acid |
| | | 1,2,3,4,5,7-$^{13}$C6-isocitroylformic acid |
| | | 1,3,4,5,6,7-$^{13}$C6-isocitroylformic acid |
| 2-$^{13}$C1-isocitric acid | 1,2,3-$^{13}$C3-isocitric acid | 1,2,3,4-$^{13}$C4-isocitric acid |
| 3-$^{13}$C1-isocitric acid | 1,2,4-$^{13}$C3-isocitric acid | 1,2,3,5-$^{13}$C4-isocitric acid |
| | 1,2,5-$^{13}$C3-isocitric acid | 1,2,3,6-$^{13}$C4-isocitric acid |
| | 1,2,6-$^{13}$C3-isocitric acid | 1,2,4,5-$^{13}$C4-isocitric acid |
| 1,2-$^{13}$C2-isocitric acid | 1,3,4-$^{13}$C3-isocitric acid | 1,2,4,6-$^{13}$C4-isocitric acid |
| 1,3-$^{13}$C2-isocitric acid | 1,3,5-$^{13}$C3-isocitric acid | 1,2,5,6-$^{13}$C4-isocitric acid |
| 1,4-$^{13}$C2-isocitric acid | 1,3,6-$^{13}$C3-isocitric acid | 1,3,4,5-$^{13}$C4-isocitric acid |
| 1,5-$^{13}$C2-isocitric acid | 1,4,6-$^{13}$C3-isocitric acid | 1,3,4,6-$^{13}$C4-isocitric acid |
| 1,6-$^{13}$C2-isocitric acid | 1,5,6-$^{13}$C3-isocitric acid | 1,4,5,6-$^{13}$C4-isocitric acid |
| 2,3-$^{13}$C2-isocitric acid | 2,3,4-$^{13}$C3-isocitric acid | |
| 2,4-$^{13}$C2-isocitric acid | 2,3,5-$^{13}$C3-isocitric acid | 1,2,3,4,5-$^{13}$C5-isocitric acid |
| 2,5-$^{13}$C2-isocitric acid | 2,3,6-$^{13}$C3-isocitric acid | 1,2,3,4,6-$^{13}$C5-isocitric acid |
| 2,6-$^{13}$C2-isocitric acid | 3,4,5-$^{13}$C3-isocitric acid | 1,2,3,5,6-$^{13}$C5-isocitric acid |
| 3,4-$^{13}$C2-isocitric acid | 3,4,6-$^{13}$C3-isocitric acid | 1,3,4,5,6-$^{13}$C5-isocitric acid |
| 3,5-$^{13}$C2-isocitric acid | 3,5,6-$^{13}$C3-isocitric acid | |
| 3,6-$^{13}$C2-isocitric acid | 4,5,6-$^{13}$C3-isocitric acid | |
| 4,5-$^{13}$C2-isocitric acid | | 1,2,3,4,5,6-$^{13}$C6-isocitric acid |
| 4,6-$^{13}$C2-isocitric acid | | |
| 5,6-$^{13}$C2-isocitric acid | | |
| | 4,6-$^{13}$C2-tricarballylic acid | |
| 1-$^{13}$C1-tricarballylic acid | 5,6-$^{13}$C2-tricarballylic acid | 1,2,3,4-$^{13}$C4-tricarballylic acid |
| 2-$^{13}$C1-tricarballylic acid | | 1,2,3,5-$^{13}$C4-tricarballylic acid |
| 3-$^{13}$C1-tricarballylic acid | | 1,2,3,6-$^{13}$C4-tricarballylic acid |
| 4-$^{13}$C1-tricarballylic acid | 1,2,3-$^{13}$C3-tricarballylic acid | 1,2,4,5-$^{13}$C4-tricarballylic acid |
| 5-$^{13}$C1-tricarballylic acid | 1,2,4-$^{13}$C3-tricarballylic acid | 1,2,4,6-$^{13}$C4-tricarballylic acid |
| 6-$^{13}$C1-tricarballylic acid | 1,2,5-$^{13}$C3-tricarballylic acid | 1,2,5,6-$^{13}$C4-tricarballylic acid |
| | 1,2,6-$^{13}$C3-tricarballylic acid | 1,3,4,5-$^{13}$C4-tricarballylic acid |
| | 1,3,4-$^{13}$C3-tricarballylic acid | 1,3,4,6-$^{13}$C4-tricarballylic acid |
| 1,2-$^{13}$C2-tricarballylic acid | 1,3,5-$^{13}$C3-tricarballylic acid | 1,4,5,6-$^{13}$C4-tricarballylic acid |
| 1,3-$^{13}$C2-tricarballylic acid | 1,3,6-$^{13}$C3-tricarballylic acid | |
| 1,4-$^{13}$C2-tricarballylic acid | 1,4,5-$^{13}$C3-tricarballylic acid | |
| 1,5-$^{13}$C2-tricarballylic acid | 1,4,6-$^{13}$C3-tricarballylic acid | 1,2,3,4,5-$^{13}$C5-tricarballylic acid |
| 1,6-$^{13}$C2-tricarballylic acid | 1,5,6-$^{13}$C3-tricarballylic acid | 1,2,3,4,6-$^{13}$C5-tricarballylic acid |
| 2,3-$^{13}$C2-tricarballylic acid | 2,3,4-$^{13}$C3-tricarballylic acid | 1,2,3,5,6-$^{13}$C5-tricarballylic acid |
| 2,4-$^{13}$C2-tricarballylic acid | 2,3,5-$^{13}$C3-tricarballylic acid | 1,3,4,5,6-$^{13}$C5-tricarballylic acid |
| 2,5-$^{13}$C2-tricarballylic acid | 2,3,6-$^{13}$C3-tricarballylic acid | |
| 2,6-$^{13}$C2-tricarballylic acid | 3,4,5-$^{13}$C3-tricarballylic acid | |
| 3,4-$^{13}$C2-tricarballylic acid | 3,4,6-$^{13}$C3-tricarballylic acid | 1,2,3,4,5,6-$^{13}$C6-tricarballylic acid |
| 3,5-$^{13}$C2-tricarballylic acid | 3,5,6-$^{13}$C3-tricarballylic acid | |
| 3,6-$^{13}$C2-tricarballylic acid | 4,5,6-$^{13}$C3-tricarballylic acid | and |
| 4,5-$^{13}$C2-tricarballylic acid. | | |

In another embodiment, provided herein is a compound selected from the group consisting of:

TABLE C

| | | |
|---|---|---|
| 1-$^{13}$C1-oxopentenedioic acid | 1,2-$^{13}$C2-oxopentenedioic acid | 1,2,3-$^{13}$C3-oxopentenedioic acid |
| 2-$^{13}$C1-oxopentenedioic acid | 1,3-$^{13}$C2-oxopentenedioic acid | 1,2,4-$^{13}$C3-oxopentenedioic acid |
| 3-$^{13}$C1-oxopentenedioic acid | 1,4-$^{13}$C2-oxopentenedioic acid | 1,2,5-$^{13}$C3-oxopentenedioic acid |

TABLE C-continued

| | | |
|---|---|---|
| 4-$^{13}$C1-oxopentenedioic acid | 1,5-$^{13}$C2-oxopentenedioic acid | 1,3,4-$^{13}$C3-oxopentenedioic acid |
| 5-$^{13}$C1-oxopentenedioic acid | 2,3-$^{13}$C2-oxopentenedioic acid | 1,3,5-$^{13}$C3-oxopentenedioic acid |
| | 2,4-$^{13}$C2-oxopentenedioic acid | 1,4,5-$^{13}$C3-oxopentenedioic acid |
| | 2,5-$^{13}$C2-oxopentenedioic acid | 2,3,4-$^{13}$C3-oxopentenedioic acid |
| 1,2,3,4-$^{13}$C4-oxopentenedioic acid | 3,4-$^{13}$C2-oxopentenedioic acid | 2,4,5-$^{13}$C3-oxopentenedioic acid |
| 1,2,3,5-$^{13}$C4-oxopentenedioic acid | 3,5-$^{13}$C2-oxopentenedioic acid | 3,4,5-$^{13}$C3-oxopentenedioic acid |
| 1,3,4,5-$^{13}$C4-oxopentenedioic acid | 4,5-$^{13}$C2-oxopentenedioic acid | |
| 2,3,4,5-$^{13}$C4-oxopentenedioic acid | | 1,2,3,4,5-$^{13}$C5-oxopentenedioic acid |
| 2-$^{13}$C1-fumaric acid | 1,3-$^{13}$C2-fumaric acid | 1,2,3-$^{13}$C3-fumaric acid |
| 3-$^{13}$C1-fumaric acid | 2,4-$^{13}$C2-fumaric acid | 1,2,4-$^{13}$C3-fumaric acid |
| 4-$^{13}$C1-fumaric acid | 3,4-$^{13}$C2-fumaric acid | 1,3,4-$^{13}$C3-fumaric acid |
| | | 2,3,4-$^{13}$C3-fumaric acid |
| 1,2,3,4,5,6,7-$^{12}$C7-trans-aconitoyl formic acid | 1,2,3-$^{13}$C3-trans-aconitoyl formic acid | 1,2,3,4-$^{13}$C4-trans-aconitoyl formic acid |
| | 1,2,4-$^{13}$C3-trans-aconitoyl formic acid | 1,2,3,5-$^{13}$C4-trans-aconitoyl formic acid |
| 1-$^{13}$C1-trans-aconitoyl formic acid | 1,2,5-$^{13}$C3-trans-aconitoyl formic acid | 1,2,3,6-$^{13}$C4-trans-aconitoyl formic acid |
| 2-$^{13}$C1-trans-aconitoyl formic acid | 1,2,6-$^{13}$C3-trans-aconitoyl formic acid | 1,2,3,7-$^{13}$C4-trans-aconitoyl formic acid |
| 3-$^{13}$C1-trans-aconitoyl formic acid | 1,2,7-$^{13}$C3-trans-aconitoyl formic acid | 1,2,4,5-$^{13}$C4-trans-aconitoyl formic acid |
| 4-$^{13}$C1-trans-aconitoyl formic acid | 1,3,4-$^{13}$C3-trans-aconitoyl formic acid | 1,2,4,6-$^{13}$C4-trans-aconitoyl formic acid |
| 5-$^{13}$C1-trans-aconitoyl formic acid | 1,3,5-$^{13}$C3-trans-aconitoyl formic acid | 1,2,4,7-$^{13}$C4-trans-aconitoyl formic acid |
| 6-$^{13}$C1-trans-aconitoyl formic acid | 1,3,6-$^{13}$C3-trans-aconitoyl formic acid | 1,2,5,6-$^{13}$C4-trans-aconitoyl formic acid |
| 7-$^{13}$C1-trans-aconitoyl formic acid | 1,3,7-$^{13}$C3-trans-aconitoyl formic acid | 1,2,5,7-$^{13}$C4-trans-aconitoyl formic acid |
| | 1,4,5-$^{13}$C3-trans-aconitoyl formic acid | 1,2,6,7-$^{13}$C4-trans-aconitoyl formic acid |
| | 1,4,6-$^{13}$C3-trans-aconitoyl formic acid | 1,3,4,5-$^{13}$C4-trans-aconitoyl formic acid |
| 1,2-$^{13}$C2-trans-aconitoyl formic acid | 1,4,7-$^{13}$C3-trans-aconitoyl formic acid | 1,3,4,6-$^{13}$C4-trans-aconitoyl formic acid |
| 1,3-$^{13}$C2-trans-aconitoyl formic acid | 1,5,6-$^{13}$C3-trans-aconitoyl formic acid | 1,3,6,7-$^{13}$C4-trans-aconitoyl formic acid |
| 1,4-$^{13}$C2-trans-aconitoyl formic acid | 1,5,7-$^{13}$C3-trans-aconitoyl formic acid | 1,4,5,6-$^{13}$C4-trans-aconitoyl formic acid |
| 1,5-$^{13}$C2-trans-aconitoyl formic acid | 1,6,7-$^{13}$C3-trans-aconitoyl formic acid | 1,4,5,7-$^{13}$C4-trans-aconitoyl formic acid |
| 1,6-$^{13}$C2-trans-aconitoyl formic acid | 2,3,4-$^{13}$C3-trans-aconitoyl formic acid | 1,4,6,7-$^{13}$C4-trans-aconitoyl formic acid |
| 1,7-$^{13}$C2-trans-aconitoyl formic acid | 2,3,5-$^{13}$C3-trans-aconitoyl formic acid | 1,5,6,7-$^{13}$C4-trans-aconitoyl formic acid |
| 2,3-$^{13}$C2-trans-aconitoyl formic acid | 2,3,6-$^{13}$C3-trans-aconitoyl formic acid | |
| 2,4-$^{13}$C2-trans-aconitoyl formic acid | 2,3,7-$^{13}$C3-trans-aconitoyl formic acid | 1,2,3,4,5-$^{13}$C5-trans-aconitoyl formic acid |
| 2,5-$^{13}$C2-trans-aconitoyl formic acid | 3,4,5-$^{13}$C3-trans-aconitoyl formic acid | 1,2,3,4,6-$^{13}$C5-trans-aconitoyl formic acid |
| 2,6-$^{13}$C2-trans-aconitoyl formic acid | 3,4,6-$^{13}$C3-trans-aconitoyl formic acid | 1,2,3,4,7-$^{13}$C5-trans-aconitoyl formic acid |
| 2,7-$^{13}$C2-trans-aconitoyl formic acid | 3,4,7-$^{13}$C3-trans-aconitoyl formic acid | 1,2,3,5,6-$^{13}$C5-trans-aconitoyl formic acid |
| 3,4-$^{13}$C2-trans-aconitoyl formic acid | 3,5,6-$^{13}$C3-trans-aconitoyl formic acid | 1,2,3,5,7-$^{13}$C5-trans-aconitoyl formic acid |
| 3,5-$^{13}$C2-trans-aconitoyl formic acid | 3,5,7-$^{13}$C3-trans-aconitoyl formic acid | 1,2,3,6,7-$^{13}$C5-trans-aconitoyl formic acid |
| 3,6-$^{13}$C2-trans-aconitoyl formic acid | 3,6,7-$^{13}$C3-trans-aconitoyl formic acid | 1,3,4,5,6-$^{13}$C5-trans-aconitoyl formic acid |
| 3,7-$^{13}$C2-trans-aconitoyl formic acid | 4,5,6-$^{13}$C3-trans-aconitoyl formic acid | 1,3,4,5,7-$^{13}$C5-trans-aconitoyl formic acid |
| 4,5-$^{13}$C2-trans-aconitoyl formic acid | 4,5,7-$^{13}$C3-trans-aconitoyl formic acid | 1,3,4,6,7-$^{13}$C5-trans-aconitoyl formic acid |
| 4,6-$^{13}$C2-trans-aconitoyl formic acid | 4,6,7-$^{13}$C3-trans-aconitoyl formic acid | 1,4,5,6,7-$^{13}$C5-trans-aconitoyl formic acid |
| 4,7-$^{13}$C2-trans-aconitoyl formic acid | 5,6,7-$^{13}$C3-trans-aconitoyl formic acid | |
| 5,6-$^{13}$C2-trans-aconitoyl formic acid | | |
| 5,7-$^{13}$C2-trans-aconitoyl formic acid | | 1,2,3,4,5,6-$^{13}$C6-trans-aconitoyl formic acid |

TABLE C-continued

| | | |
|---|---|---|
| 6,7-$^{13}$C2-trans-aconitoyl formic acid | 1,2,3,4,5,6,7-$^{13}$C7-trans-aconitoyl formic acid | 1,2,3,4,5,7-$^{13}$C6-trans-aconitoyl formic acid |
| | | 1,3,4,5,6,7-$^{13}$C6-trans-aconitoyl formic acid |
| 1,2,3,4,5,6,7-$^{12}$C7-cis-aconitoyl formic acid | 1,2,3-$^{13}$C3-cis-aconitoyl formic acid | 1,2,3,4-$^{13}$C4-cis-aconitoyl formic acid |
| | 1,2,4-$^{13}$C3-cis-aconitoyl formic acid | 1,2,3,5-$^{13}$C4-cis-aconitoyl formic acid |
| 1-$^{13}$C1-cis-aconitoyl formic acid | 1,2,5-$^{13}$C3-cis-aconitoyl formic acid | 1,2,3,6-$^{13}$C4-cis-aconitoyl formic acid |
| 2-$^{13}$C1-cis-aconitoyl formic acid | 1,2,6-$^{13}$C3-cis-aconitoyl formic acid | 1,2,3,7-$^{13}$C4-cis-aconitoyl formic acid |
| 3-$^{13}$C1-cis-aconitoyl formic acid | 1,2,7-$^{13}$C3-cis-aconitoyl formic acid | 1,2,4,5-$^{13}$C4-cis-aconitoyl formic acid |
| 4-$^{13}$C1-cis-aconitoyl formic acid | 1,3,4-$^{13}$C3-cis-aconitoyl formic acid | 1,2,4,6-$^{13}$C4-cis-aconitoyl formic acid |
| 5-$^{13}$C1-cis-aconitoyl formic acid | 1,3,5-$^{13}$C3-cis-aconitoyl formic acid | 1,2,4,7-$^{13}$C4-cis-aconitoyl formic acid |
| 6-$^{13}$C1-cis-aconitoyl formic acid | 1,3,6-$^{13}$C3-cis-aconitoyl formic acid | 1,2,5,6-$^{13}$C4-cis-aconitoyl formic acid |
| 7-$^{13}$C1-cis-aconitoyl formic acid | 1,3,7-$^{13}$C3-cis-aconitoyl formic acid | 1,2,5,7-$^{13}$C4-cis-aconitoyl formic acid |
| | 1,4,5-$^{13}$C3-cis-aconitoyl formic acid | 1,2,6,7-$^{13}$C4-cis-aconitoyl formic acid |
| | 1,4,6-$^{13}$C3-cis-aconitoyl formic acid | 1,3,4,5-$^{13}$C4-cis-aconitoyl formic acid |
| 1,2-$^{13}$C2-cis-aconitoyl formic acid | 1,4,7-$^{13}$C3-cis-aconitoyl formic acid | 1,3,4,6-$^{13}$C4-cis-aconitoyl formic acid |
| 1,3-$^{13}$C2-cis-aconitoyl formic acid | 1,5,6-$^{13}$C3-cis-aconitoyl formic acid | 1,3,6,7-$^{13}$C4-cis-aconitoyl formic acid |
| 1,4-$^{13}$C2-cis-aconitoyl formic acid | 1,5,7-$^{13}$C3-cis-aconitoyl formic acid | 1,4,5,6-$^{13}$C4-cis-aconitoyl formic acid |
| 1,5-$^{13}$C2-cis-aconitoyl formic acid | 1,6,7-$^{13}$C3-cis-aconitoyl formic acid | 1,4,5,7-$^{13}$C4-cis-aconitoyl formic acid |
| 1,6-$^{13}$C2-cis-aconitoyl formic acid | 2,3,4-$^{13}$C3-cis-aconitoyl formic acid | 1,4,6,7-$^{13}$C4-cis-aconitoyl formic acid |
| 1,7-$^{13}$C2-cis-aconitoyl formic acid | 2,3,5-$^{13}$C3-cis-aconitoyl formic acid | 1,5,6,7-$^{13}$C4-cis-aconitoyl formic acid |
| 2,3-$^{13}$C2-cis-aconitoyl formic acid | 2,3,6-$^{13}$C3-cis-aconitoyl formic acid | |
| 2,4-$^{13}$C2-cis-aconitoyl formic acid | 2,3,7-$^{13}$C3-cis-aconitoyl formic acid | 1,2,3,4,5-$^{13}$C5-cis-aconitoyl formic acid |
| 2,5-$^{13}$C2-cis-aconitoyl formic acid | 3,4,5-$^{13}$C3-cis-aconitoyl formic acid | 1,2,3,4,6-$^{13}$C5-cis-aconitoyl formic acid |
| 2,6-$^{13}$C2-cis-aconitoyl formic acid | 3,4,6-$^{13}$C3-cis-aconitoyl formic acid | 1,2,3,4,7-$^{13}$C5-cis-aconitoyl formic acid |
| 2,7-$^{13}$C2-cis-aconitoyl formic acid | 3,4,7-$^{13}$C3-cis-aconitoyl formic acid | 1,2,3,5,6-$^{13}$C5-cis-aconitoyl formic acid |
| 3,4-$^{13}$C2-cis-aconitoyl formic acid | 3,5,6-$^{13}$C3-cis-aconitoyl formic acid | 1,2,3,5,7-$^{13}$C5-cis-aconitoyl formic acid |
| 3,5-$^{13}$C2-cis-aconitoyl formic acid | 3,5,7-$^{13}$C3-cis-aconitoyl formic acid | 1,2,3,6,7-$^{13}$C5-cis-aconitoyl formic acid |
| 3,6-$^{13}$C2-cis-aconitoyl formic acid | 3,6,7-$^{13}$C3-cis-aconitoyl formic acid | 1,3,4,5,6-$^{13}$C5-cis-aconitoyl formic acid |
| 3,7-$^{13}$C2-cis-aconitoyl formic acid | 4,5,6-$^{13}$C3-cis-aconitoyl formic acid | 1,3,4,5,7-$^{13}$C5-cis-aconitoyl formic acid |
| 4,5-$^{13}$C2-cis-aconitoyl formic acid | 4,5,7-$^{13}$C3-cis-aconitoyl formic acid | 1,3,4,6,7-$^{13}$C5-cis-aconitoyl formic acid |
| 4,6-$^{13}$C2-cis-aconitoyl formic acid | 4,6,7-$^{13}$C3-cis-aconitoyl formic acid | 1,4,5,6,7-$^{13}$C5-cis-aconitoyl formic acid |
| 4,7-$^{13}$C2-cis-aconitoyl formic acid | 5,6,7-$^{13}$C3-cis-aconitoyl formic acid | |
| 5,6-$^{13}$C2-cis-aconitoyl formic acid | | |
| 5,7-$^{13}$C2-cis-aconitoyl formic acid | | 1,2,3,4,5,6-$^{13}$C6-cis-aconitoyl formic acid |
| 6,7-$^{13}$C2-cis-aconitoyl formic acid | 1,2,3,4,5,6,7-$^{13}$C7-cis-aconitoyl formic acid | 1,2,3,4,5,7-$^{13}$C6-cis-aconitoyl formic acid |
| | | 1,3,4,5,6,7-$^{13}$C6-cis-aconitoyl formic acid |
| | 4,6-$^{13}$C2-cis-aconitic acid | |
| 1-$^{13}$C1-cis-aconitic acid | 5,6-$^{13}$C2-cis-aconitic acid | 1,2,3,4-$^{13}$C4-cis-aconitic acid |
| 2-$^{13}$C1-cis-aconitic acid | | 1,2,3,5-$^{13}$C4-cis-aconitic acid |
| 3-$^{13}$C1-cis-aconitic acid | | 1,2,3,6-$^{13}$C4-cis-aconitic acid |
| 4-$^{13}$C1-cis-aconitic acid | 1,2,3-$^{13}$C3-cis-aconitic acid | 1,2,4,5-$^{13}$C4-cis-aconitic acid |
| 5-$^{13}$C1-cis-aconitic acid | 1,2,4-$^{13}$C3-cis-aconitic acid | 1,2,4,6-$^{13}$C4-cis-aconitic acid |
| 6-$^{13}$C1-cis-aconitic acid | 1,2,5-$^{13}$C3-cis-aconitic acid | 1,2,5,6-$^{13}$C4-cis-aconitic acid |
| | 1,2,6-$^{13}$C3-cis-aconitic acid | 1,3,4,5-$^{13}$C4-cis-aconitic acid |
| | 1,3,4-$^{13}$C3-cis-aconitic acid | 1,3,4,6-$^{13}$C4-cis-aconitic acid |

TABLE C-continued

| | | |
|---|---|---|
| 1,2-$^{13}$C2-cis-aconitic acid | 1,3,5-$^{13}$C3-cis-aconitic acid | 1,4,5,6-$^{13}$C4-cis-aconitic acid |
| 1,3-$^{13}$C2-cis-aconitic acid | 1,3,6-$^{13}$C3-cis-aconitic acid | |
| 1,4-$^{13}$C2-cis-aconitic acid | 1,4,5-$^{13}$C3-cis-aconitic acid | |
| 1,5-$^{13}$C2-cis-aconitic acid | 1,4,6-$^{13}$C3-cis-aconitic acid | 1,2,3,4,5-$^{13}$C5-cis-aconitic acid |
| 1,6-$^{13}$C2-cis-aconitic acid | 1,5,6-$^{13}$C3-cis-aconitic acid | 1,2,3,4,6-$^{13}$C5-cis-aconitic acid |
| 2,3-$^{13}$C2-cis-aconitic acid | 2,3,4-$^{13}$C3-cis-aconitic acid | 1,2,3,5,6-$^{13}$C5-cis-aconitic acid |
| 2,4-$^{13}$C2-cis-aconitic acid | 2,3,5-$^{13}$C3-cis-aconitic acid | 1,3,4,5,6-$^{13}$C5-cis-aconitic acid |
| 2,5-$^{13}$C2-cis-aconitic acid | 2,3,6-$^{13}$C3-cis-aconitic acid | |
| 2,6-$^{13}$C2-cis-aconitic acid | 3,4,5-$^{13}$C3-cis-aconitic acid | |
| 3,4-$^{13}$C2-cis-aconitic acid | 3,4,6-$^{13}$C3-cis-aconitic acid | 1,2,3,4,5,6-$^{13}$C6-cis-aconitic acid |
| 3,5-$^{13}$C2-cis-aconitic acid | 3,5,6-$^{13}$C3-cis-aconitic acid | |
| 3,6-$^{13}$C2-cis-aconitic acid | 4,5,6-$^{13}$C3-cis-aconitic acid | |
| 4,5-$^{13}$C2-cis-aconitic acid | | |
| | 4,6-$^{13}$C2-trans-aconitic acid | |
| 1-$^{13}$C1-trans-aconitic acid | 5,6-$^{13}$C2-trans-aconitic acid | 1,2,3,4-$^{13}$C4-trans-aconitic acid |
| 2-$^{13}$C1-trans-aconitic acid | | 1,2,3,5-$^{13}$C4-trans-aconitic acid |
| 3-$^{13}$C1-trans-aconitic acid | | 1,2,3,6-$^{13}$C4-trans-aconitic acid |
| 4-$^{13}$C1-trans-aconitic acid | 1,2,3-$^{13}$C3-trans-aconitic acid | 1,2,4,5-$^{13}$C4-trans-aconitic acid |
| 5-$^{13}$C1-trans-aconitic acid | 1,2,4-$^{13}$C3-trans-aconitic acid | 1,2,4,6-$^{13}$C4-trans-aconitic acid |
| 6-$^{13}$C1-trans-aconitic acid | 1,2,5-$^{13}$C3-trans-aconitic acid | 1,2,5,6-$^{13}$C4-trans-aconitic acid |
| | 1,2,6-$^{13}$C3-trans-aconitic acid | 1,3,4,5-$^{13}$C4-trans-aconitic acid |
| | 1,3,4-$^{13}$C3-trans-aconitic acid | 1,3,4,6-$^{13}$C4-trans-aconitic acid |
| 1,2-$^{13}$C2-trans-aconitic acid | 1,3,5-$^{13}$C3-trans-aconitic acid | 1,4,5,6-$^{13}$C4-trans-aconitic acid |
| 1,3-$^{13}$C2-trans-aconitic acid | 1,3,6-$^{13}$C3-trans-aconitic acid | |
| 1,4-$^{13}$C2-trans-aconitic acid | 1,4,5-$^{13}$C3-trans-aconitic acid | |
| 1,5-$^{13}$C2-trans-aconitic acid | 1,4,6-$^{13}$C3-trans-aconitic acid | 1,2,3,4,5-$^{13}$C5-trans-aconitic acid |
| 1,6-$^{13}$C2-trans-aconitic acid | 1,5,6-$^{13}$C3-trans-aconitic acid | 1,2,3,4,6-$^{13}$C5-trans-aconitic acid |
| 2,3-$^{13}$C2-trans-aconitic acid | 2,3,4-$^{13}$C3-trans-aconitic acid | 1,2,3,5,6-$^{13}$C5-trans-aconitic acid |
| 2,4-$^{13}$C2-trans-aconitic acid | 2,3,5-$^{13}$C3-trans-aconitic acid | 1,3,4,5,6-$^{13}$C5-trans-aconitic acid |
| 2,5-$^{13}$C2-trans-aconitic acid | 2,3,6-$^{13}$C3-trans-aconitic acid | |
| 2,6-$^{13}$C2-trans-aconitic acid | 3,4,5-$^{13}$C3-trans-aconitic acid | |
| 3,4-$^{13}$C2-trans-aconitic acid | 3,4,6-$^{13}$C3-trans-aconitic acid | 1,2,3,4,5,6-$^{13}$C6-trans-aconitic acid |
| 3,5-$^{13}$C2-trans-aconitic acid | 3,5,6-$^{13}$C3-trans-aconitic acid | |
| 3,6-$^{13}$C2-trans-aconitic acid | 4,5,6-$^{13}$C3-trans-aconitic acid | and |
| 4,5-$^{13}$C2-trans-aconitic acid. | | |

In a further embodiment, provided herein is a compound selected from the group consisting of compounds in Table B and Table C above.

Kits

Provided herein are kits that include a compound of the disclosure, or a pharmaceutically acceptable salt, tautomer, stereoisomer, mixture of stereoisomers, prodrug, or deuterated analog thereof, and suitable packaging. In one embodiment, a kit further includes instructions for use. In one aspect, a kit includes a compound of the disclosure, or a pharmaceutically acceptable salt, tautomer, stereoisomer, mixture of stereoisomers, prodrug, or deuterated analog thereof, and a label and/or instructions for use of the compounds in the diagnostic assays described herein.

Provided herein is a diagnostic kit for metabolic flux analysis comprising one or more organic acids prepared by any method or process described herein. Also provided is the use of one or more organic acids prepared by any method or process described herein, or any composition described herein, for the preparation of a diagnostic kit for metabolic flux analysis.

Provided herein are also articles of manufacture that include a compound described herein or a pharmaceutically acceptable salt, tautomer, stereoisomer, mixture of stereoisomers, prodrug, or deuterated analog thereof in a suitable container. The container may be a vial, jar, ampoule, pre-loaded syringe, and/or a pouch.

Synthesis of the Compounds

The compounds may be prepared using the methods disclosed herein and routine modifications thereof, which will be apparent given the disclosure herein and methods well known in the art. Conventional and well-known synthetic methods may be used in addition to the teachings herein. The synthesis of typical compounds described herein may be accomplished as described in the following examples. If available, reagents may be purchased commercially, e.g., from Sigma Aldrich or other chemical suppliers.

General Synthesis

Typical embodiments of compounds described herein may be synthesized using the general reaction schemes described below. It will be apparent given the description herein that the general schemes may be altered by substitution of the starting materials with other materials having similar structures to result in products that are correspondingly different. Descriptions of syntheses follow to provide numerous examples of how the starting materials may vary to provide corresponding products. Given a desired product for which the substituent groups are defined, the necessary starting materials generally may be determined by inspection. Starting materials are typically obtained from commercial sources or synthesized using published methods. For synthesizing compounds which are embodiments described in the present disclosure, inspection of the structure of the compound to be synthesized will provide the identity of each substituent group. The identity of the final product will generally render apparent the identity of the necessary starting materials by a simple process of inspection, given the examples herein. In general, compounds described herein are typically stable and isolatable at room temperature and pressure.

FIG. 1 shows several possible routes for the synthesis of biological metabolites (e.g., metabolites that occur in the TCA cycle). Starting from pyruvic acid, a reaction with glyoxylic acid provides 4-hydroxy ketoglutaric acid which can be decarboxylated to α-hydroxy malic acid by treatment with hydrogen peroxide or any other suitable oxidant. The 4-hydroxy ketoglutaric acid can be dehydrated and further reduced to provide α-ketoglutaric acid which can be converted to succinic acid in the presence of an oxidant. The dehydrated 4-hydroxy ketoglutaric acid, i.e., oxopentenedioic acid can be decarboxylated to fumaric acid in the presence of an oxidant. The α-ketoglutaric acid can be subjected to additional reactions shown in FIG. 1 to obtain additional metabolites shown in FIG. 1. The reactions in FIG. 1 would typically be enzyme catalyzed reactions in a biological system which would lead to formation of various organic acids (biological metabolites). By contrast, the methods described herein are non-enzymatic protocols for obtaining the organic acids (biological metabolites) of FIG. 1.

In a typical procedure, depending on the desired products, pyruvic acid is contacted with about 1-5 equivalents of glyoxylic acid in the presence of a buffer. The reaction pH is adjusted to a pH ranging from about 4 to about 13, or from about 5 to about 12, or from about 6 to about 11. The reaction is stirred at a temperature ranging from −10° C. to about room temperature (about 20° C.-25° C.) or heated at a suitable temperature ranging from about 25° C. to about 200° C., or from about 25° C. to about 100° C., or from about 35° C. to about 90° C., or from about 45° C. to about 80° C. The reaction mixture is maintained for a time ranging from minutes, to hours, to days or weeks or months, and the progress of the reaction is monitored using any suitable technique known to one of skill in the art (e.g., by NMR spectroscopy). The reaction provides an aldol addition compound (e.g., 4-hydroxy ketoglutaric acid of FIG. 1), or an aldol condensation compound (i.e., an enone compound, e.g., oxopentanedioic acid of FIG. 1). Depending on the equivalents of glyoxylic acid used, the α,β-unsaturated bond in the aldol condensation compound may be reduced when the excess glyoxylic acid acts as a reductant to obtain a saturated di-acid (e.g., α-ketoglutaric acid of FIG. 1).

Then, in the same reaction pot, the reaction mixture comprising the aldol addition compound, or the aldol condensation compound, or the reduced aldol condensation compound, is treated with an oxidant (e.g., hydrogen peroxide) to obtain an oxidatively decarboxylated compound.

In alternate embodiments, the aldol addition compound, the aldol condensation compound, or the reduced aldol condensation compound, is subjected to a reductive amination or a trans amination to obtain an amino acid product. In more embodiments, the keto group of any α-keto acid product is subjected to a reduction to obtain an α-hydroxy acid. Thus it will be apparent to one of skill in the art that different reaction sequences can produce different product acids starting from α-keto acids and all such reaction sequences are contemplated within the scope of embodiments presented herein. In specific embodiments, the methods described herein are conducted in the absence of iron (e.g., the reactions described herein do not comprise $Fe^{2+}$ ions, or any other form of iron).

Embodiment 1

In Scheme 1, an embodiment of a process is described where a non-enzymatic aldol addition of an α-ketoacid (for example glyoxylate) or aldehyde (for example formaldehyde) occurs via combination with an α-ketoacid nucleophile (for example pyruvate), followed by a dehydration (2), an enone reduction (3), and an oxidative decarboxylation (4) to produce organic acids.

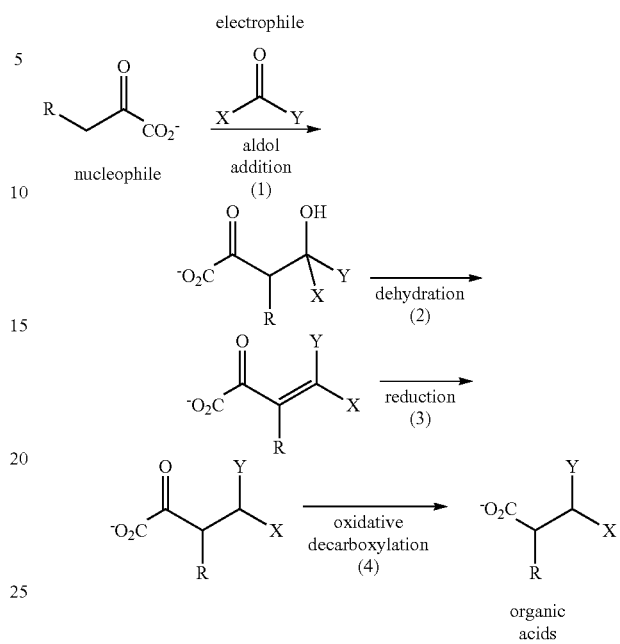

Embodiment 2

In Scheme 2, a further embodiment is described containing a similar process to Scheme 1 where step (3) can be skipped to allow collection of unsaturated organic acids.

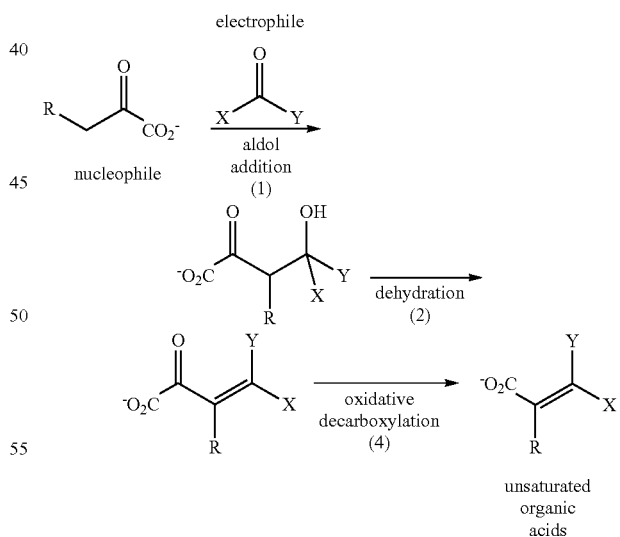

Embodiment 3

In Scheme 3, a further embodiment is described containing a similar process to Scheme 1 wherein steps (2) and (3) can be skipped to allow collection of β-hydroxy organic acids

Scheme 3

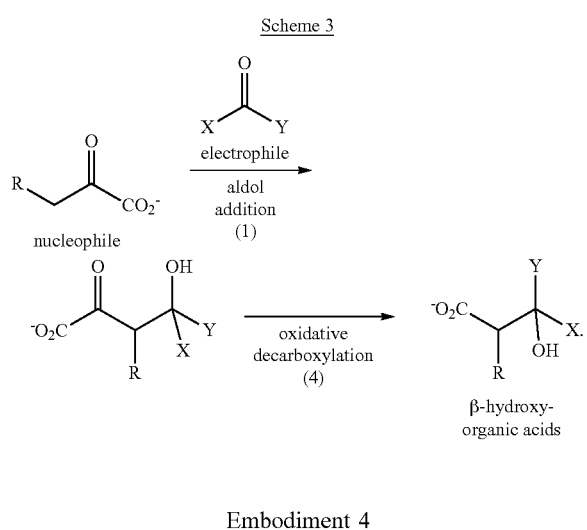

Embodiment 4

In Scheme 4, a further embodiment is described containing a process similar to Scheme 1, where steps may be repeated during the reaction series:

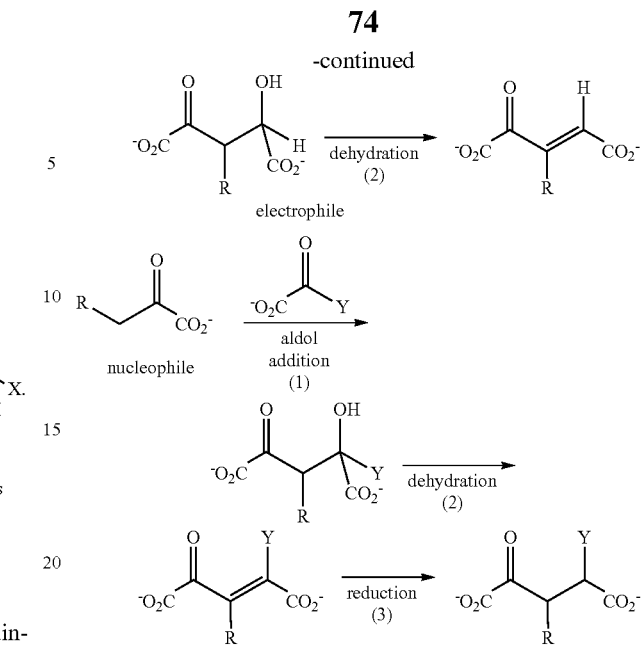

Scheme 4

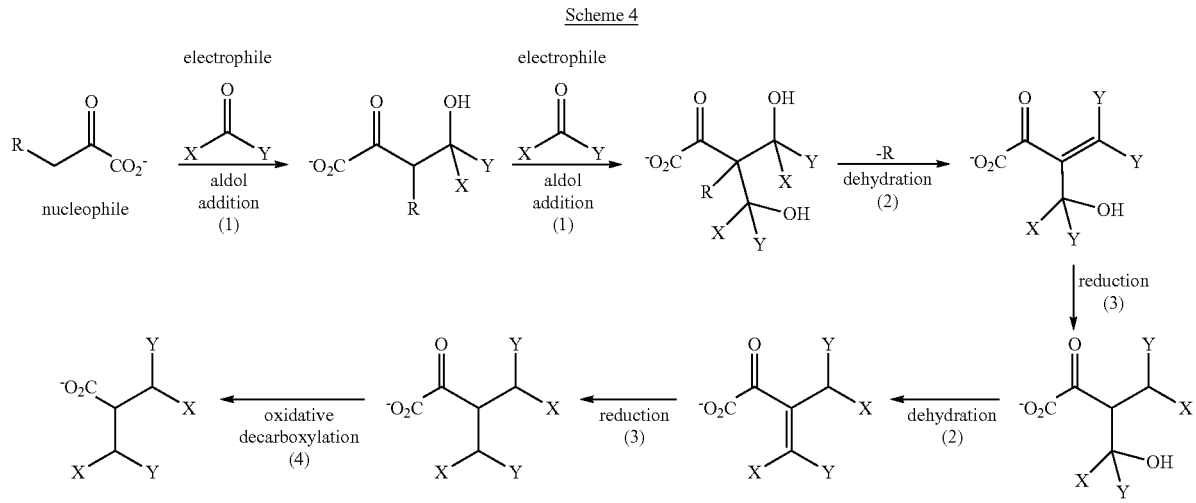

Embodiment 5

In Scheme 5, a further embodiment is described containing processes similar to Schemes 1, 2, 3, and 4 where the oxidative decarboxylation (4) step can be skipped to allow collection of α-ketoacids at any point:

Scheme 5

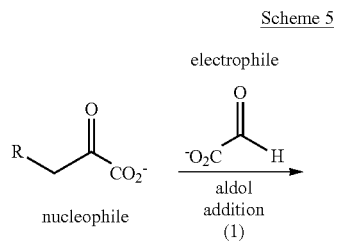

In a further embodiment, the reaction sequences described herein produce the following products. The numbering for non-limiting step sequences refer to numbering in Schemes 1-5 above.

| Non-limiting example organic acid products | Nucleophile | Electrophile | Non-limiting Step Sequences |
| --- | --- | --- | --- |
| α-ketoglutarate | pyruvate | glyoxylate | 1,2,3 |
| succinate | pyruvate | glyoxylate | 1,2,3,4 |
| isocitrate | pyruvate | glyoxylate | 1,2,3,1,4 |
| isocitrate | α-ketoglutarate | glyoxylate | 1,4 |
| malate | pyruvate | glyoxylate | 1,4 |
| fumarate | pyruvate | glyoxylate | 1,2,4 |
| aconitate | pyruvate | glyoxylate | 1,2,3,1,2,4 |
| aconitate | α-ketoglutarate | glyoxylate | 1,2,4 |

-continued

| Non-limiting example organic acid products | Nucleophile | Electrophile | Non-limiting Step Sequences |
|---|---|---|---|
| tricarballylate | pyruvate | glyoxylate | 1,2,3,1,2,3,4 |
| tricarballylate | α-ketoglutarate | glyoxylate | 1,2,3,4 |
| 4-hydroxyaconitate | pyruvate | glyoxylate | 1,1,2,4 |

Embodiment 6

In Scheme 6, a further embodiment is described containing a process similar to Scheme 1, wherein, in place of oxidative decarboxylation (4), a hydride reduction ($^1$H, $^2$H or $^3$H) (5) of the keto group can be carried out to generate α-hydroxy-organic acids, α-hydroxy-unsaturated-organic acids, and α,γ-dihydroxy-organic acids:

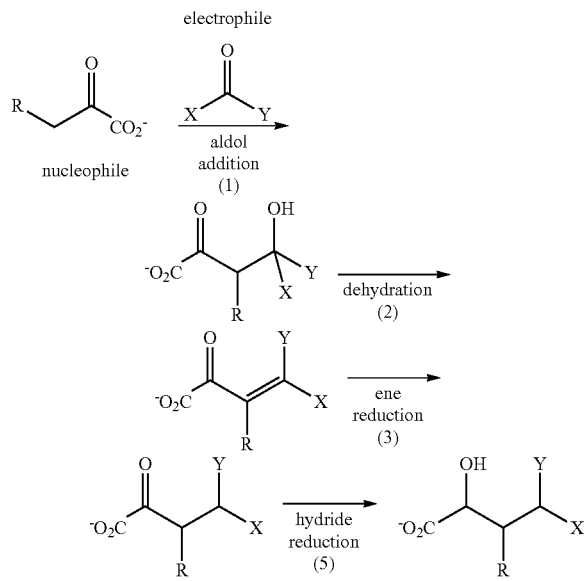

Scheme 6

Embodiment 7

In a further embodiment, the reaction sequences described herein produce a range of products. The numbering for non-limiting step sequences refer to numbering in Schemes 1-6 above. Embodiment 7 below describes a similar process to certain of the above exemplary processes, where the keto reduction can occur in the following order of steps to produce α-hydroxy organic acids. The numbering for step sequences below refers to numbering in Schemes 1-6 above.

Embodiment 7 Sequences (8.1) Reaction sequences may be carried out as follows: (1), (5)

(8.2) Reaction sequences may be carried out as follows: (1), (2), (5)

(8.3) Reaction sequences may be carried out as follows: (1), (2), (3), (5)

(8.4) Reaction sequences may be carried out as follows: (1), (2), (3), (1), (5)

(8.5) Reaction sequences may be carried out as follows: (1), (2), (3), (1), (2), (5)

(8.6) Reaction sequences may be carried out as follows: (1), (2), (3), (1), (2), (3), (5)

In a sub-embodiment, the reaction sequences may produce the following example products: The numbering for non-limiting step sequences refer to numbering in Schemes 1-6 above.

| Non-limiting example organic acid products | Nucleophile | Electrophile | Non-limiting Step Sequences |
|---|---|---|---|
| α-hydroxyglutarate | pyruvate | glyoxylate | 1,2,3,5 |
| α-hydroxyglutaconate | pyruvate | glyoxylate | 1,2,5 |
| 2,4-dihydroxyglutarate | pyruvate | glyoxylate | 1,5 |
| 3-carboxylmethyl-2,4-dihydroxyglutarate | pyruvate | glyoxylate | 1,2,3,1,5 |
| 3-carboxylmethyl-2,4-dihydroxyglutarate | α-ketoglutarate | glyoxylate | 1,5 |
| 3-carboxymethyl-2-hydroxyglutaconate | pyruvate | glyoxylate | 1,2,3,1,2,5 |
| 3-carboxymethyl-2-hydroxyglutaconate | α-ketoglutarate | glyoxylate | 1,2,5 |
| 3-carboxymethyl-2-hydroxyglutarate | pyruvate | glyoxylate | 1,2,3,1,2,3,5 |
| 3-carboxymethyl-2-hydroxyglutarate | α-ketoglutarate | glyoxylate | 1,2,3,5 |
| 3-(2'-hydroxy-carboxymethyl)-4-hydroxyglutaconate | pyruvate | glyoxylate | 1,1,2,5 |
| 2,4-dihydroxybutanoate | pyruvate | formaldehyde | 1,5 |

Embodiment 8

In Scheme 8, a further embodiment is described containing a similar process to that described in Scheme 1, where in place of oxidative decarboxylation (4), reductive amination or transamination (6) of the keto group can be carried out:

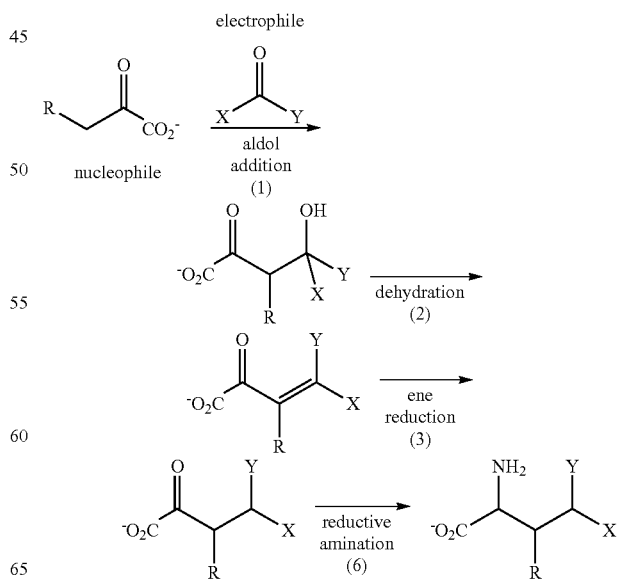

Scheme 8

Embodiment 9

In Embodiment 9, a further embodiment is described containing a similar process to that described in Embodiment 7, where the reductive amination can occur via the following order of steps to generate amino acid derivatives. The numbering for step sequences refers to numbering in Schemes 1-5 and 8 above.

Embodiment 9 Sequences (8.1) Reaction sequences may be carried out as follows: (1), (6)
(8.2) Reaction sequences may be carried out as follows: (1), (2), (6)
(8.3) Reaction sequences may be carried out as follows: (1), (2), (3), (6)
(8.4) Reaction sequences may be carried out as follows: (1), (2), (3), (1), (6)
(8.5) Reaction sequences may be carried out as follows: (1), (2), (3), (1), (2), (6)
(8.6) Reaction sequences may be carried out as follows: (1), (2), (3), (1), (2), (3), (6).

In a sub-embodiment, the reaction sequences described herein may produce the following example products. The numbering for non-limiting step sequences refer to numbering in Schemes 1-5 and 8 above.

| Non-limiting example organic acid products | Nucleophile | Electrophile | Non-limiting Step Sequences |
|---|---|---|---|
| glutamate | pyruvate | glyoxylate | 1,2,3,6 |
| γ-hydroxyglutamate | pyruvate | glyoxylate | 1,2,6 |
| β-dehydroglutamate | pyruvate | glyoxylate | 1,2,3,6 |
| β-carboxymethyl-γ-hydroxyglutamate | pyruvate | glyoxylate | 1,2,3,1,6 |
| β-carboxymethyl-γ-hydroxyglutamate | α-ketoglutarate | glyoxylate | 1,6 |
| β-carboxymethyl-β-dehydroglutamate | pyruvate | glyoxylate | 1,2,3,1,2,6 |
| β-carboxymethyl-β-dehydroglutamate | α-ketoglutarate | glyoxylate | 1,2,6 |
| homoserine | pyruvate | formaldehyde | 1,2,6 |

Embodiment 10

In Scheme 10, a further embodiment is described containing a process similar to Scheme 1, where after oxidative decarboxylation (4), subsequent hydration (7) of compounds containing a double bond may be carried out:

Scheme 10

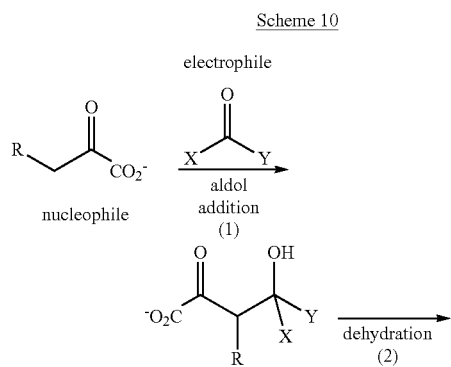

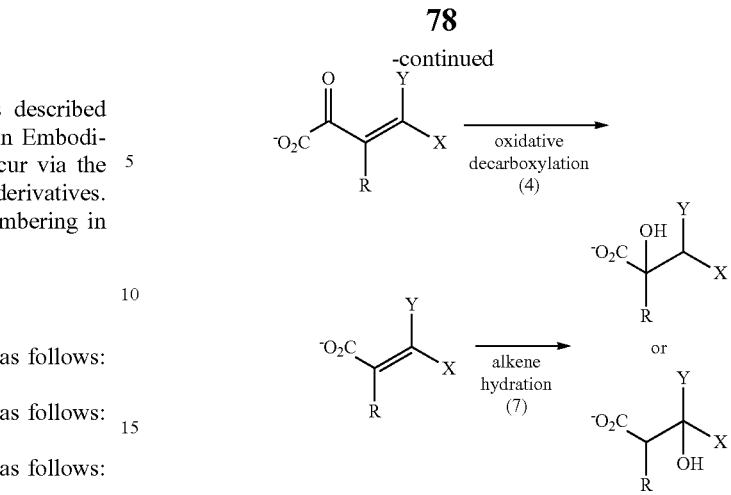

Embodiment 11 is a further embodiment comprising a process similar to certain of the Schemes 1-6, 8 and 10 above, and Embodiments 7 and 9 above, wherein, when dissolved in $D_2O$ (deuterated water), i.e., where the reaction solvent comprises deuterated water, protons on the carbon located alpha to the keto acid functional group (—C(O)$CO_2$—) will readily exchange with a deuterium.

Embodiment 12 is a further embodiment where the process as described herein allows the selective reduction of an enone conjugated to a keto group using glyoxylic acid as the reductant.

Embodiment 13

In Scheme 13 is described a further embodiment where the molecule aconitoyl formate, shown below, is capable of adding an electrophile on the carbon located beta (β) to the carbonyl, where "x" can be selected from any of the species set forth below:

Scheme 13

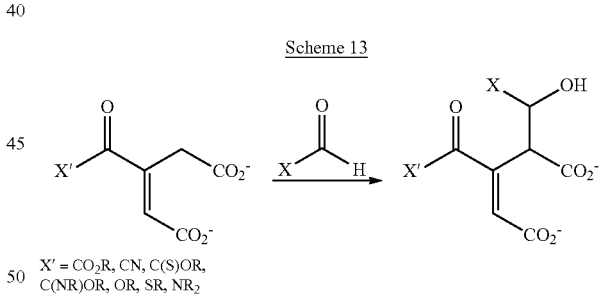

X' = $CO_2R$, CN, C(S)OR, C(NR)OR, OR, SR, $NR_2$ where R is as defined herein for Formula (A).

Embodiment 14 is a further embodiment where a process is compatible with the replacement of carboxylic acids of any synthetic target with an α-keto acid in order to enable higher yielding reactions under milder conditions. Additionally, the target carboxylic acid can be generated at the end of the synthesis by treatment of the α-keto acid with an oxidant, for example dilute aqueous hydrogen peroxide (or other oxidant).

Embodiment 15 is a further embodiment wherein a process similar to those described in Schemes 1-6, 8, 10, and Embodiments 7 and 9 above, is capable of producing compounds not currently available by methods of the prior art, or isolatable in nature, which may enable novel methods and outcomes in metabolic flux analyses.

EXAMPLES

The following examples are included to demonstrate specific embodiments of the disclosure. It should be appreciated by those of skill in the art that the techniques disclosed in the examples which follow represent techniques to function well in the practice of the disclosure, and thus can be considered to constitute specific modes for its practice. However, those of skill in the art should, in light of the present disclosure, appreciate that many changes can be made in the specific embodiments which are disclosed and still obtain a like or similar result without departing from the spirit and scope of the disclosure.

List of Abbreviations and Acronyms

| Abbreviation | Meaning |
| --- | --- |
| ° C. | Degree Celsius |
| aq. | Aqueous |
| g | Grams |
| hrs | Hours |
| M | Molar |
| mg | Milligram |
| MHz | Megahertz |
| ml/mL | Milliliter |
| mM | Millimolar |
| mmol | Millimole |
| nL | Nanoliter |
| nm | Nanometer |
| μL/μl | Microliter |
| μM | Micromolar |
| TCA | Tricarboxylic acid |

Materials:

All reactions were run under an atmosphere of $N_2$ unless otherwise noted. All reagents were used as purchased from their chemical manufacturer: sodium pyruvate (≥99%, ReagentPlus, Sigma-Aldrich), α-ketoglutaric acid disodium salt dihydrate (≥98%, Aldrich Chemistry), oxaloacetic acid (≥97%, Sigma-Aldrich), 50 wt % in $H_2O$ glyoxylic acid solution (Sigma-Aldrich), aluminum potassium sulfate dodecahydrate (BioReagent, Sigma Life Science), DL-4-hydroxy-2-ketoglutaric acid lithium salt (≥90%, Sigma Life Science), and 30 wt % in $H_2O$ hydrogen peroxide solution (contains inhibitor, assayed 29.0 to 32.0%, Sigma-Aldrich 216763). $^1$H-NMR spectra were collected using a Varian 400-MR 400 MHz high-field superconducting NMR spectrometer with chemical shifts (δ) reported in ppm. $^{13}$C-NMR spectra were recorded at 298K using a Bruker AV-600 (151 MHz for $^{13}$C) equipped with a 5 mm DCH cryoprobe. NMR samples were prepared by adding 100 μL of the crude reaction mixture to 600 μL of $D_2O$ containing a t-butanol internal standard. HPLC chromatograms were collected using a Waters Alliance e2695 Separations Module coupled to a Waters 2998 Photodiode Array Detector. HPLC samples were prepared by adding 300 μL of the crude reaction mixture to 1.55 mL of 0.1% formic acid in water. Samples were eluted with an isocratic mobile phase of 0.1% formic acid in water at 0.75 mL/min for 20 min on a Synergi 4u Polar-RP 80A (250×4.6 mm) column and visualized at by UV absorbance at 210 nm.

Example 1

Preparation of 2-$^{13}$C-α-ketoglutarate 891 mg of 2-$^{13}$C-pyruvic acid (10.0 mmol, 200 mM) was dissolved in 46.0 mL of a 0.50 M aq. pH 7 sodium phosphate buffer in a 100-mL flask with a stirbar. Then, 3.31 mL (2.22 g) of 50 wt % glyoxylic acid in $H_2O$ (3 equiv.) was added. The reaction pH was adjusted to 6.7 by adding 4.0 M aq. NaOH dropwise, and the mixture was then stirred at 60° C. for 21 h. The product can be purified by reverse phase (C18) flash chromatography.

Example 2

Preparation of 1-$^{13}$C-succinate 486 mg of 2-$^{13}$C-α-ketoglutarate (disodium salt, 2.14 mmol, 200 mM) was suspended in 10.0 mL of deionized water in a vial. Then, 656 uL of 30 wt % aqueous hydrogen peroxide (3 equiv.) was added, and the reaction mixture was stirred at room temperature for 0.5 hrs. Water and excess hydrogen peroxide were removed by evaporation under reduced pressure. The product can be purified by reverse phase (C18) flash chromatography.

Example 3

Preparation of 1-$^{13}$C-trans-aconitic acid 681 mg of 2-$^{13}$C-α-ketoglutarate (disodium salt, 3.00 mmol, 1000 mM) was suspended in 3.00 mL of deionized water in a 10-mL vial. Then, 513 mg of sodium glyoxylate monohydrate (1.5 equiv.) was added. The reaction pH was adjusted to 12.7 by adding 4.0 M aq. NaOH dropwise, and the mixture was then stirred at 40° C. for 1 h. 0.919 mL of 30 wt % of hydrogen peroxide (3 equiv.) was added, and the reaction was stirred at room temperature for 30 minutes. After acidification to pH 1.5 with conc. sulfuric acid, the product was purified by reverse phase (C18) flash chromatography with a mobile phase containing water, acetonitrile and 0.1% trifluoroacetic acid.

Example 4

Preparation of $^{15}$N-glutamate 139 mg of $^{15}$N-glycine (1.83 mmol, 365 mM) was dissolved in 5.0 mL of deionized water in a 20-mL vial with a stirbar. 495 mg of disodium α-ketoglutarate (1.2 equiv.) and 87 mg of aluminum potassium sulfate dodecahydrate (0.1 equiv.) were added. The reaction pH was adjusted to 5.0 by adding 10% aq. HCl dropwise, and then the mixture was stirred at 80° C. for 4 h. The product can be purified by reverse phase (C18) flash chromatography.

Example 5

Preparation of 1-$^{13}$C-tricarballylic acid 681 mg of 2-$^{13}$C-α-ketoglutarate (disodium salt, 3.00 mmol, 1000 mM) was suspended in 3.00 mL of deionized water in a 10-mL vial. Then, 1368 mg of sodium glyoxylate monohydrate (4 equiv.) was added. The reaction pH was adjusted to 12.7 by adding 4.0 M aq. NaOH dropwise, and the mixture was then stirred at 60° C. for 12 hrs. 0.919 mL of 30 wt % of hydrogen peroxide (3 equiv.) was added, and the reaction was stirred at room temperature for 0.5 hrs. After acidification to pH 1.5 with conc. sulfuric acid, the product was purified by reverse phase (C18) flash chromatography with a mobile phase containing water, acetonitrile and 0.1% trifluoroacetic acid.

Figure 2:
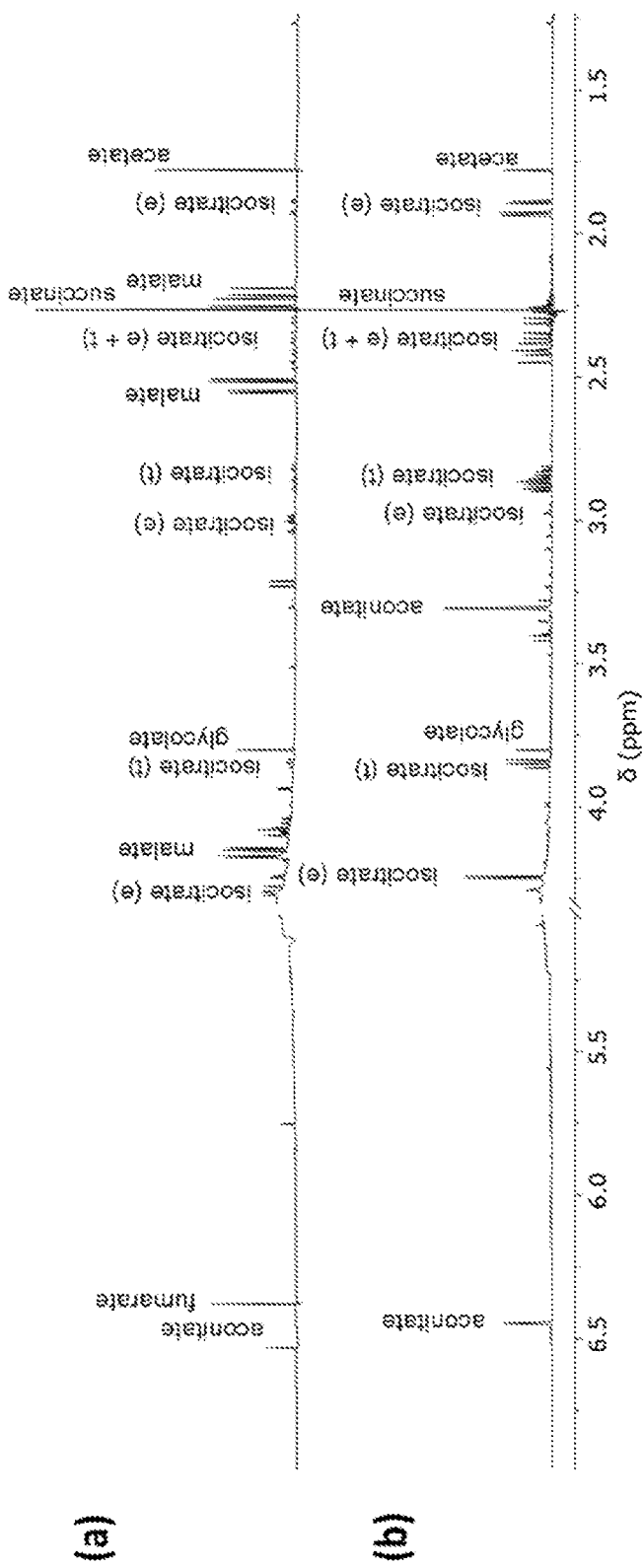
FIG. 2 shows NMR data for a sequence of reactions using the protocols described herein. (a)$^1$H NMR (in $D_2O$) for reaction of pyruvate and excess of glyoxylate (b)$^1$H NMR (in $D_2O$) for a reaction of α-ketoglutarate and 1 equivalent of glyoxylate.

FIG. 2 shows NMR data for a sequence of reactions using the protocols described herein. (a) $^1$H NMR (in D$_2$O) of a 100 µl aliquot from a reaction of 200 mM pyruvate and 3 equiv. of glyoxylate in a pH 7 phosphate buffer at 50° C. for 21 h, followed by the addition of 5.0 equiv. of H$_2$O$_2$ and stirring for 0.5 h at rt. (b)$^1$H NMR (in D$_2$O) of a 100 µl aliquot from a reaction of 200 mM α-ketoglutarate and 1 equiv. of glyoxylate in a pH 7 phosphate buffer at 50° C. for 21 h, followed by the addition of 5.0 equiv. of H$_2$O$_2$ and stirring for 0.5 h at rt. The $^1$H NMR data shows the formation of various organic acids from the reaction between pyruvate and glyoxylate. The products can be purified by reverse phase (C18) flash chromatography.

Biological Assays

This example describes testing for metabolic flux analysis. The analysis involves tracing stable non-natural isotopes of biological intermediates—prepared as described herein—as they are processed in vivo and/or in vitro. Tissue or fluid samples are analyzed by mass spectrometry and/or nuclear magnetic resonance spectroscopy to determine the number and/or location of isotopically labeled atoms (e.g., $^{13}$C, $^{15}$N). Techniques for metabolic flux analysis are known in the art. For example the compounds described herein may be used for metabolic flux analysis according to protocols described by Klein, S. and Heinzle, E. *WIREs Syst Biol Med* (2012) 4:261-272, by Langziel et al., *BMC Biology*, (2019) 17:51, and/or by Faubert, B. et al., *Cell*, (2017) 171:358-371. The compounds provided by the methods described herein serve as standards/markers for metabolic flux analysis.

The isotope distribution pattern in the tissue or fluid samples is used to determine the relative activities of biological pathways, particularly of the tricarboxylic acid (TCA) cycle and glycolysis. Atypical isotope distribution patterns, compared to control samples, are indicative of atypical metabolisms, thereby indicating specific pathologies (such as, for example, pathologies indicative of cancer).

Unless otherwise defined, all technical and scientific terms used herein have the same meaning as commonly understood by one of ordinary skill in the art to which this invention belongs.

The inventions illustratively described herein may suitably be practiced in the absence of any element or elements, limitation or limitations, not specifically disclosed herein. Thus, for example, the terms "comprising", "including," "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed.

Thus, it should be understood that although the present invention has been specifically disclosed by preferred embodiments and optional features, modification, improvement and variation of the inventions embodied therein herein disclosed may be resorted to by those skilled in the art, and that such modifications, improvements and variations are considered to be within the scope of this invention. The materials, methods, and examples provided here are representative of preferred embodiments, are exemplary, and are not intended as limitations on the scope of the invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

In addition, where features or aspects of the invention are described in terms of Markush groups, those skilled in the art will recognize that the invention is also thereby described in terms of any individual member or subgroup of members of the Markush group.

All publications, patent applications, patents, and other references mentioned herein are expressly incorporated by reference in their entirety, to the same extent as if each were incorporated by reference individually. In case of conflict, the present specification, including definitions, will control.

It is to be understood that while the disclosure has been described in conjunction with the above embodiments, that the foregoing description and examples are intended to illustrate and not limit the scope of the disclosure. Other aspects, advantages and modifications within the scope of the disclosure will be apparent to those skilled in the art to which the disclosure pertains.

The invention claimed is:

1. A method for reducing an α,β-unsaturated bond in an aldol condensation compound, the method comprising
    (1) contacting an aldol nucleophile with an aldehydic electrophile to provide an aldol addition compound;
    (2) dehydrating the aldol addition compound to provide an aldol condensation compound having an α,β-unsaturated bond; and
    (3) reducing the α,β-unsaturated bond in the aldol condensation compound by contacting the aldol condensation compound with the aldehydic electrophile;
    wherein the aldol nucleophile is of Formula (A):

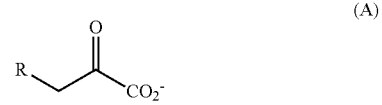

(A)

wherein
    R is hydrogen, C$_{1-12}$alkyl, C$_{2-10}$heteroalkyl, C$_{6-20}$aryl, C$_{3-12}$heteroaryl, C$_{3-10}$cycloalkyl, C$_{2-10}$ heterocyclyl, C$_{1-12}$alkyl-C$_{6-20}$aryl, C$_{1-12}$alkyl-C$_{3-12}$heteroaryl, C$_{1-12}$alkyl-C$_{3-10}$cycloalkyl, or C$_{1-12}$alkyl-C$_{2-10}$heterocyclyl, wherein alkyl, heteroalkyl, aryl, heteroaryl, cycloalkyl, and heterocyclyl are independently optionally substituted with one or more substituents selected from the group consisting of alkyl, alkenyl, alkynyl, alkoxy, acyl, amino, amido, amidino, aryl, azido, carbamoyl, carboxyl, carboxyl ester, cyano, guanidino, halo, haloalkyl, haloalkoxy, heteroalkyl, heteroaryl, heterocyclyl, hydroxy, hydrazino, imino, oxo, nitro, alkylsulfinyl, sulfonic acid, alkylsulfonyl, thiocyanate, thiol, thione, or combinations thereof; and
    wherein the aldehydic electrophile is of Formula (B):

(B)

wherein
X is H, COOH or C(=O)OCH₂CH₃; and
Y is H.

2. The method of claim 1, wherein the aldehydic electrophile is a reactant in step (1) and a reductant in step (3).

3. A method for preparing an organic acid, the method comprising
(1) contacting an α-keto acid with an aldehydic electrophile to provide an aldol addition compound;
(2) dehydrating the aldol addition compound to provide an aldol condensation compound having an α,β-unsaturated bond;
(3) reducing the α,β-unsaturated bond in the aldol condensation compound by contacting the aldol condensation compound with the aldehydic electrophile; and
(4) oxidatively decarboxylating the reduced aldol condensation compound to provide the organic acid;
or
(5) reducing the keto group in the reduced aldol condensation compound to provide the organic acid;
or
(6) subjecting the reduced aldol condensation compound to reductive amination or transamination to provide the organic acid;
wherein the alpha keto acid is of Formula (A):

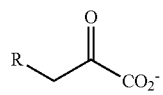

(A)

wherein
R is hydrogen, $C_{1-12}$alkyl, $C_{2-10}$heteroalkyl, $C_{6-20}$aryl, $C_{3-12}$heteroaryl, $C_{3-10}$cycloalkyl, $C_{2-10}$ heterocyclyl, $C_{1-12}$alkyl-$C_{6-20}$aryl, $C_{1-12}$alkyl-$C_{3-12}$heteroaryl, $C_{1-12}$ alkyl-$C_{3-10}$cycloalkyl, or $C_{1-12}$ alkyl-$C_{2-10}$heterocyclyl, wherein alkyl, heteroalkyl, aryl, heteroaryl, cycloalkyl, and heterocyclyl are independently optionally substituted with one or more substituents selected from the group consisting of alkyl, alkenyl, alkynyl, alkoxy, acyl, amino, amido, amidino, aryl, azido, carbamoyl, carboxyl, carboxyl ester, cyano, guanidino, halo, haloalkyl, haloalkoxy, heteroalkyl, heteroaryl, heterocyclyl, hydroxy, hydrazino, imino, oxo, nitro, alkylsulfinyl, sulfonic acid, alkylsulfonyl, thiocyanate, thiol, thione, or combinations thereof; and
wherein the aldehydic electrophile is of Formula (B):

(B)

wherein
X is H, COOH or C(=O)OCH₂CH₃; and
Y is H.

4. The method of claim 3, wherein the aldehydic electrophile is a reactant in step (1) and a reductant in step (3).

5. The method of claim 3 for the conversion of a-keto acids to organic acids thereof, the method comprising
(1) contacting an alpha keto acid of Formula (A) with an aldehydic electrophile of Formula (B)

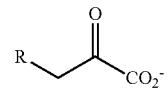

(A)

(B)

to provide an aldol addition compound of Formula (C)

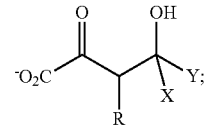

(C)

(2) dehydrating the compound of Formula (C) to provide an aldol condensation compound of Formula (D)

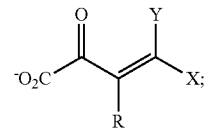

(D)

(3) reducing the compound of Formula (D) to provide a compound of Formula (E)

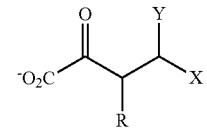

(E)

by contacting the compound of Formula (D) with the aldehydic electrophile; and
(4) oxidatively decarboxylating the compound of Formula (E) to provide an organic acid of Formula (F)

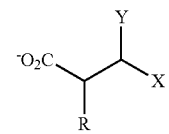

(F)

wherein
R is hydrogen, $C_{1-12}$alkyl, $C_{2-10}$heteroalkyl, $C_{6-20}$aryl, $C_{3-12}$heteroaryl, $C_{3-10}$cycloalkyl, $C_{2-10}$ heterocyclyl, $C_{1-12}$alkyl-$C_{6-20}$aryl, $C_{1-12}$alkyl-$C_{3-12}$heteroaryl, $C_{1-12}$ alkyl-$C_{3-10}$cycloalkyl, or $C_{1-12}$ alkyl-$C_{2-10}$heterocyclyl, wherein alkyl, heteroalkyl, aryl, heteroaryl, cycloalkyl, and heterocyclyl are independently optionally substituted with one or more substituents selected from the group consisting of alkyl, alkenyl, alkynyl, alkoxy, acyl, amino, amido, amidino, aryl, azido, carbamoyl, carboxyl, carboxyl ester, cyano, guanidino, halo, haloalkyl, haloalkoxy, heteroalkyl, heteroaryl, heterocyclyl, hydroxy, hydrazine, imino, oxo, nitro, alkylsulfinyl, sulfonic acid, alkylsulfonyl, thiocyanate, thiol, thione, and combinations thereof;

X is selected from the group consisting of H, COOH, and C(=O)OCH$_2$CH$_3$; and

Y is H.

6. The method of claim 3 for the conversion of α-keto acids to organic acids thereof, the method comprising (1) contacting an alpha keto acid of Formula (A) with an aldehydic electrophile of Formula (B)

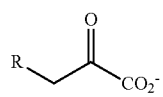

(A)

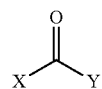

(B)

to provide an aldol addition compound of Formula (C)

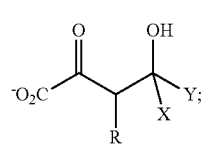

(C)

(2) dehydrating the compound of Formula (C) to provide an aldol condensation compound of Formula (D)

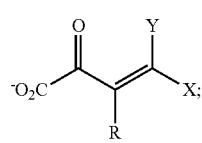

(D)

(3) reducing the compound of Formula (D) to obtain a compound of Formula (E)

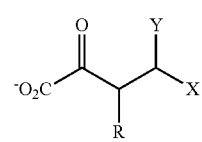

(E)

by contacting the compound of Formula (D) with the aldehydic electrophile; and (6) subjecting the compound of Formula (E) to reductive amination or transamination to provide an organic acid of Formula (G)

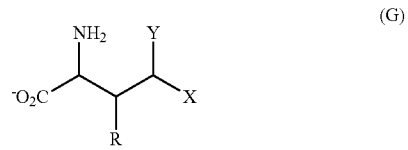

(G)

wherein

R is hydrogen, C$_{1-12}$alkyl, C$_{2-10}$heteroalkyl, C$_{6-20}$aryl, C$_{3-12}$heteroaryl, C$_{3-10}$cycloalkyl, C$_{2-10}$ heterocyclyl, C$_{1-12}$alkyl-C$_{6-20}$aryl, C$_{1-12}$alkyl-C$_{3-12}$heteroaryl, C$_{1-12}$ alkyl-C$_{3-10}$cycloalkyl, or C$_{1-12}$ alkyl-C$_{2-10}$heterocyclyl, wherein alkyl, heteroalkyl, aryl, heteroaryl, cycloalkyl, and heterocyclyl are independently optionally substituted with one or more substituents selected from the group consisting of alkyl, alkenyl, alkynyl, alkoxy, acyl, amino, amido, amidino, aryl, azido, carbamoyl, carboxyl, carboxyl ester, cyano, guanidino, halo, haloalkyl, haloalkoxy, heteroalkyl, heteroaryl, heterocyclyl, hydroxy, hydrazino, imino, oxo, nitro, alkylsulfinyl, sulfonic acid, alkylsulfonyl, thiocyanate, thiol, thione, or combinations thereof;

X is selected from the group consisting of H, COOH, and C(=O)OCH$_2$CH$_3$; and

Y is H.

7. The method of claim 3 for the conversion of a-keto acids to organic acids thereof, the method comprising (1) contacting an alpha keto acid of Formula (A) with an aldehydic electrophile of Formula (B)

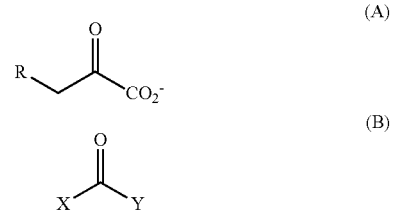

(A)

(B)

to provide an aldol addition compound of Formula (C)

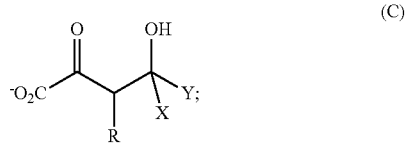

(C)

(2) dehydrating the compound of Formula (C) to provide an aldol condensation compound of Formula (D)

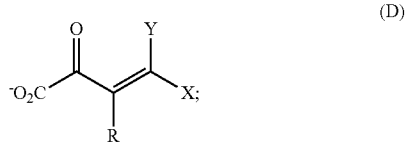

(D)

(3) reducing the compound of Formula (D) to provide a compound of Formula (E)

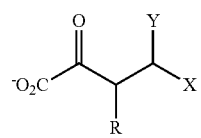
(E)

by contacting the compound of Formula (D) with the aldehydic electrophile; and (5) further reducing the compound of Formula (E) to provide an organic acid of Formula (H)

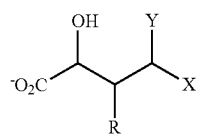
(H)

wherein

R is hydrogen, $C_{1-12}$alkyl, $C_{2-10}$heteroalkyl, $C_{6-20}$aryl, $C_{3-12}$heteroaryl, $C_{3-10}$cycloalkyl, $C_{2-10}$ heterocyclyl, $C_{1-12}$alkyl-$C_{6-20}$aryl, $C_{1-12}$alkyl-$C_{3-12}$heteroaryl, $C_{1-12}$alky-$C_{3-10}$cycloalkyl, or $C_{1-12}$ alkyl-$C_{2-10}$heterocyclyl, wherein alkyl, heteroalkyl, aryl, heteroaryl, cycloalkyl, and heterocyclyl are independently optionally substituted with one or more substituents selected from the group consisting of alkyl, alkenyl, alkynyl, alkoxy, acyl, amino, amido, amidino, and, azido, carbamoyl, carboxyl, carboxyl ester, cyano, guanidino, halo, haloalkyl, haloalkoxy, heteroalkyl, heteroaryl, heterocyclyl, hydroxy, hydrazine, imino, oxo, nitro, alkylsulfinyl, sulfonic acid, alkylsulfonyl, thiocyanate, thiol, thione, or combinations thereof;

X is selected from the group consisting of H, COOH, and C(=O)OCH$_2$CH$_3$; and

Y is H.

8. The method of claim 7, wherein step (5) is conducted in the presence of a metal hydride.

9. A method for conversion of a-keto acids to organic acids thereof, the method comprising (1) contacting an alpha keto acid of Formula (A) with an aldehydic electrophile of Formula (B)

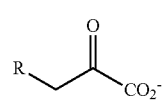
(A)

(B)

to provide an aldol addition compound of Formula (C)

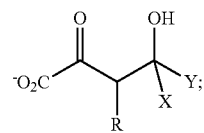
(C)

(1-1) contacting compound (C) with compound (B) to provide a compound of Formula (J)

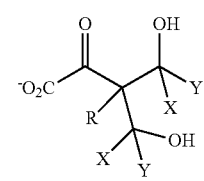
(J)

(2) dehydrating the compound of Formula (J) to provide a compound of Formula (K)

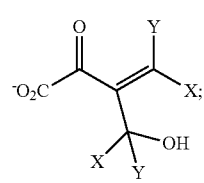
(K)

(3) reducing the compound of Formula (K) to provide a compound of Formula (L)

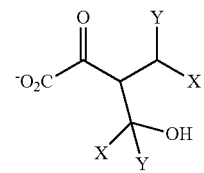
(L)

by contacting the compound of Formula (K) with the aldehydic electrophile;

(2-1) dehydrating the compound of Formula (L) to provide a compound of Formula (M)

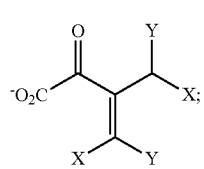
(M)

(3-1) reducing the compound of Formula (M) to obtain a compound of Formula (N)

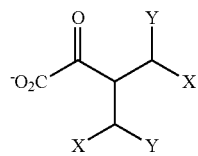

(N)

by contacting the compound of Formula (M) with the aldehydic electrophile; and (4) oxidatively decarboxylating the compound of Formula (N) to provide an organic acid of Formula (O)

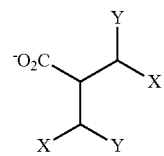

(O)

wherein

R is hydrogen, $C_{1-12}$alkyl, $C_{2-10}$heteroalkyl, $C_{6-20}$aryl, $C_{3-12}$heteroaryl, $C_{3-10}$cycloalkyl, $C_{2-10}$ heterocyclyl, $C_{1-12}$alkyl-$C_{6-20}$aryl, $C_{1-12}$alkyl-$C_{3-12}$heteroaryl, $C_{1-12}$alkyl-$C_{3-10}$cycloalkyl, or $C_{1-12}$ alkyl-$C_{2-10}$heterocyclyl, wherein alkyl, heteroalkyl, aryl, heteroaryl, cycloalkyl, and heterocyclyl are independently optionally substituted with one or more substituents selected from the group consisting of alkyl, alkenyl, alkynyl, alkoxy, acyl, amino, amido, amidino, aryl, azido, carbamoyl, carboxyl, carboxyl ester, cyano, guanidino, halo, haloalkyl, haloalkoxy, heteroalkyl, heteroaryl, heterocyclyl, hydroxy, hydrazino, imino, oxo, nitro, alkylsulfinyl, sulfonic acid, alkylsulfonyl, thiocyanate, thiol, thione, or combinations thereof;

X is selected from the group consisting of H, COOH, and $C(=O)OCH_2CH_3$; and

Y is H.

10. The method of claim 1, wherein the aldehydic electrophile is formaldehyde.

11. The method of claim 3, wherein the oxidative decarboxylation is conducted in the presence of a peracid.

12. The method of claim 3, wherein the oxidative decarboxylation is conducted in the presence of hydrogen peroxide.

13. The method of claim 3, wherein the reductive amination is conducted in the presence of aluminum sulfate.

14. The method of claim 3, wherein the reductive amination is conducted in the presence of an amine comprising a radioisotope of nitrogen.

15. The method of claim 1, wherein the method is an enzyme-free method.

16. The method of claim 1, comprising a reaction solvent selected from water, a polar organic solvent, or combination thereof.

17. The method of claim 16, wherein the solvent is water.

18. The method of claim 17, wherein the solvent is water and further, the method is conducted at a pH that is a substantially neutral pH.

19. The method of claim 16, wherein the solvent is deuterated water.

20. The method of claim 1, wherein the aldehydic electrophile comprises one or two radioisotopes of carbon.

21. The method of claim 1, wherein the aldehydic electrophile is $^{13}C2$ labeled glyoxylic acid.

22. The method of claim 3, wherein the organic acid is labeled with one or more radioisotopes of carbon, nitrogen, hydrogen or oxygen, or a combination thereof.

23. The method of claim 5, wherein R is $C_{1-12}$alkyl.

24. A method of preparing isotoplogue metabolites by reducing an α,β-unsaturated bond in an aldol condensation compound, the method comprising (1) contacting an aldol nucleophile with an aldehydic electrophile to provide an aldol addition compound;

(2) dehydrating the aldol addition compound to provide an aldol condensation compound having an α,β-unsaturated bond; and (3) reducing the α,β-unsaturated bond in the aldol condensation compound by contacting the aldol condensation compound with the aldehydic electrophile;

wherein the aldol nucleophile is of Formula (A):

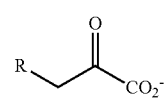

(A)

wherein

R is hydrogen, $C_{1-12}$alkyl, $C_{2-10}$heteroalkyl, $C_{6-20}$aryl, $C_{3-12}$heteroaryl, $C_{3-10}$cycloalkyl, $C_{2-10}$ heterocyclyl, $C_{1-12}$alkyl-$C_{6-20}$aryl, $C_{1-12}$alkyl-$C_{3-12}$heteroaryl, $C_{1-12}$alkyl-$C_{3-10}$cycloalkyl, or $C_{1-12}$ alkyl-$C_{2-10}$heterocyclyl, wherein alkyl, heteroalkyl, aryl, heteroaryl, cycloalkyl, and heterocyclyl are independently optionally substituted with one or more substituents selected from the group consisting of alkyl, alkenyl, alkynyl, alkoxy, acyl, amino, amido, amidino, aryl, azido, carbamoyl, carboxyl, carboxyl ester, cyano, guanidino, halo, haloalkyl, haloalkoxy, heteroalkyl, heteroaryl, heterocyclyl, hydroxy, hydrazino, imino, oxo, nitro, alkylsulfinyl, sulfonic acid, alkylsulfonyl, thiocyanate, thiol, thione, or combinations thereof; and wherein the aldehydic electrophile is of Formula (B):

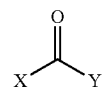

(B)

wherein

X is H, COOH or $C(=O)OCH_2CH_3$; and

Y is H.

25. The method of claim 24, wherein the isotopologue metabolites are markers for metabolic flux analysis.

* * * * *